(12) United States Patent
Hartigan et al.

(10) Patent No.: US 10,576,161 B2
(45) Date of Patent: Mar. 3, 2020

(54) COMPOSITIONS AND METHODS FOR THE DEPLETION OF CD137+ CELLS

(71) Applicant: Magenta Therapeutics, Inc., Cambridge, MA (US)

(72) Inventors: Adam Hartigan, Brookline, MA (US); Anthony Boitano, Newton, MA (US); Michael Cooke, Brookline, MA (US); Megan D. Hoban, Medford, MA (US); Rahul Palchaudhuri, Somerville, MA (US)

(73) Assignee: Magenta Therapeutics, Inc., Cambridge, MA (US)

( * ) Notice: Subject to any disclaimer, the term of this patent is extended or adjusted under 35 U.S.C. 154(b) by 0 days.

(21) Appl. No.: 15/875,793

(22) Filed: Jan. 19, 2018

(65) Prior Publication Data

US 2018/0289832 A1 Oct. 11, 2018

Related U.S. Application Data

(60) Provisional application No. 62/448,741, filed on Jan. 20, 2017, provisional application No. 62/595,977, filed on Dec. 7, 2017.

(51) Int. Cl.
| | | |
|---|---|---|
| *A61K 47/68* | (2017.01) | |
| *C07K 16/28* | (2006.01) | |
| *A61K 39/395* | (2006.01) | |
| *A61P 37/06* | (2006.01) | |
| *A61K 38/08* | (2019.01) | |
| *A61K 39/00* | (2006.01) | |

(52) U.S. Cl.
CPC .......... *A61K 47/6831* (2017.08); *A61K 38/08* (2013.01); *A61K 39/395* (2013.01); *A61K 47/6803* (2017.08); *A61K 47/6849* (2017.08); *A61P 37/06* (2018.01); *C07K 16/2878* (2013.01); *A61K 2039/505* (2013.01); *A61K 2039/545* (2013.01); *A61K 2039/572* (2013.01); *C07K 2317/24* (2013.01); *C07K 2317/33* (2013.01); *C07K 2317/565* (2013.01); *C07K 2317/732* (2013.01); *C07K 2317/76* (2013.01); *C07K 2317/92* (2013.01)

(58) Field of Classification Search
CPC .......... A61K 47/6831; A61K 2039/505; A61K 2039/572; A61K 39/395; A61K 47/6849; A61K 38/08; A61K 2039/545; A61P 37/06; C07K 2317/565; C07K 16/2878; C07K 2317/92; C07K 2317/76; C07K 2317/33; C07K 2317/24; C07K 2317/732
See application file for complete search history.

(56) References Cited

U.S. PATENT DOCUMENTS

| | | |
|---|---|---|
| 5,273,738 A | 12/1993 | Matthews et al. |
| 5,378,688 A | 1/1995 | Nett et al. |
| 5,451,575 A | 9/1995 | Kosuge et al. |
| 5,489,516 A | 2/1996 | Broudy et al. |
| 5,548,065 A | 8/1996 | Lemischka |
| 5,635,388 A | 6/1997 | Bennett et al. |
| 5,674,704 A | 10/1997 | Goodwin et al. |
| 5,777,084 A | 7/1998 | Buhring |
| 5,786,457 A | 7/1998 | Nett et al. |
| 5,808,002 A | 9/1998 | Buhring |
| 5,874,240 A | 2/1999 | Ni et al. |
| 5,906,938 A | 5/1999 | Broudy et al. |
| 5,919,911 A | 7/1999 | Broudy et al. |
| 5,922,847 A | 7/1999 | Broudy et al. |
| 5,928,893 A | 7/1999 | Kang et al. |
| 6,074,650 A | 6/2000 | Jung et al. |
| 6,099,838 A | 8/2000 | Lazarovits et al. |
| 6,156,882 A | 12/2000 | Buhring et al. |
| 6,210,669 B1 | 4/2001 | Aruffo et al. |
| 6,214,345 B1 | 4/2001 | Firestone et al. |
| 6,303,121 B1 | 10/2001 | Kwon |
| 6,339,062 B1 | 1/2002 | Williams et al. |
| 6,355,476 B1 | 3/2002 | Kwon et al. |
| 6,355,779 B1 | 3/2002 | Goodwin et al. |
| 6,362,325 B1 | 3/2002 | Kwon |
| 6,458,934 B1 | 10/2002 | Hong et al. |
| 6,569,997 B1 | 5/2003 | Kwon |
| 6,759,509 B1 | 7/2004 | King et al. |
| 6,887,673 B2 | 5/2005 | Kunkel et al. |
| 6,905,685 B2 | 6/2005 | Kwon |

(Continued)

FOREIGN PATENT DOCUMENTS

| | | |
|---|---|---|
| DE | 10219866 A1 | 11/2003 |
| EP | 766745 B1 | 10/2002 |

(Continued)

OTHER PUBLICATIONS

Strop et al., Chemistry & Biology 20: 161-167 (Year: 2013).*
Palchaudhuri et al., "Non-genotoxic conditioning for hematopoietic stem cell transplantation using a hematopoietic-cell-specific internalizing immunotoxin," Nat Biotechnol. 34(7):738-45 (22 pages) (2016).
Alexander, et al. "Depletion of autoreactive immunologic memory followed by autologous hematopoietic stem cell transplantation in patients with refractory SLE induces long-term remission through de novo generation of a juvenile and tolerant immune system," Blood, 29, vol. 113, No. 1 (2009).
Blanc, Antoine "Synthesis on Solid Phase of a Bicyclic Octapeptide Amatoxin," M.S. Thesis, The University of British Columbia, Aug. 2009.

(Continued)

*Primary Examiner* — Phuong Huynh
(74) *Attorney, Agent, or Firm* — Womble Bond Dickinson, LLP; Cristin H. Cowles, Esq.; Briana M. Erickson, Esq.

(57) ABSTRACT

The invention provides methods of preventing and treating graft-versus-host-disease and autoimmune diseases, such as those arising from transplant therapy, by selective depletion of hematopoietic cells through the use of antibody-drug conjugates and ligand-drug conjugates that specifically bind CD137. The compositions and methods described herein can be used to treat a variety of pathologies, including stem cell disorders and other blood conditions.

24 Claims, 7 Drawing Sheets

Specification includes a Sequence Listing.

(56) References Cited

U.S. PATENT DOCUMENTS

| | | |
|---|---|---|
| 6,974,863 B2 | 12/2005 | Kwon |
| 7,138,500 B1 | 11/2006 | Goodwin et al. |
| 7,160,987 B2 | 1/2007 | Lazarovits et al. |
| 7,183,385 B2 | 2/2007 | Comb et al. |
| 7,211,259 B1 | 5/2007 | Goodwin et al. |
| 7,214,493 B2 | 5/2007 | Kunkel et al. |
| 7,265,212 B2 | 9/2007 | Babcook et al. |
| 7,288,638 B2 | 10/2007 | Jure-Kunkel et al. |
| 7,659,384 B2 | 2/2010 | Jure-Kunkel et al. |
| 7,754,681 B2 | 7/2010 | Feng |
| 7,825,222 B2 | 11/2010 | Aversa et al. |
| 7,829,088 B2 | 11/2010 | Kwon |
| 7,915,391 B2 | 3/2011 | Ng et al. |
| 7,947,839 B2 | 5/2011 | Gazzard et al. |
| 8,026,353 B2 | 9/2011 | Kwon |
| 8,071,099 B2 | 12/2011 | Li et al. |
| 8,137,667 B2 | 3/2012 | Jure-Kunkel et al. |
| 8,226,945 B2 | 7/2012 | Ebens, Jr. et al. |
| 8,436,150 B2 | 5/2013 | Ng et al. |
| 8,455,622 B2 | 6/2013 | McDonagh et al. |
| 8,791,249 B2 | 7/2014 | Ng et al. |
| 8,821,867 B2 | 9/2014 | Ahrens et al. |
| 9,023,996 B2 | 5/2015 | Grosse-Hovest et al. |
| 9,085,630 B2 | 7/2015 | Crowley et al. |
| 9,109,227 B2 | 8/2015 | Valmier |
| 9,242,013 B2 | 1/2016 | Howard et al. |
| 9,388,187 B2 | 7/2016 | Howard |
| 9,468,678 B2 | 10/2016 | Ahrens et al. |
| 9,498,540 B2 | 11/2016 | Barsanti et al. |
| 9,504,756 B2 | 11/2016 | Lyon et al. |
| 9,540,443 B2 | 1/2017 | Hadari et al. |
| 9,669,107 B2 | 6/2017 | Kim et al. |
| 9,676,702 B2 | 6/2017 | Lutz et al. |
| 9,803,002 B2 | 10/2017 | Brown et al. |
| 9,938,323 B2 | 4/2018 | Grunewald et al. |
| 9,951,141 B2 | 4/2018 | Nittoli et al. |
| 10,071,170 B2 | 9/2018 | Kim et al. |
| 10,111,966 B2 | 10/2018 | Nixon et al. |
| 10,183,997 B2 | 1/2019 | Kim et al. |
| 2002/0018775 A1 | 2/2002 | Broudy et al. |
| 2003/0093819 A1 | 5/2003 | D'Andrea et al. |
| 2003/0096976 A1 | 5/2003 | Hong et al. |
| 2003/0223989 A1 | 12/2003 | Pluenneke |
| 2003/0232369 A1 | 12/2003 | Bushnell et al. |
| 2006/0014197 A1 | 1/2006 | Landick |
| 2006/0121030 A1 | 6/2006 | Schwarz et al. |
| 2006/0182744 A1 | 8/2006 | Strome et al. |
| 2008/0003224 A1 | 1/2008 | Fong et al. |
| 2008/0305113 A1 | 12/2008 | Kwon et al. |
| 2009/0054358 A1 | 2/2009 | Small et al. |
| 2009/0220529 A1 | 9/2009 | Trouet et al. |
| 2010/0093008 A1 | 4/2010 | Goss et al. |
| 2010/0226927 A1 | 9/2010 | Weissman et al. |
| 2010/0267019 A1 | 10/2010 | Hallen et al. |
| 2011/0177104 A1 | 7/2011 | Kwon et al. |
| 2012/0058047 A9 | 3/2012 | Strome et al. |
| 2012/0076722 A1 | 3/2012 | Strome et al. |
| 2012/0269774 A1 | 10/2012 | Ichim et al. |
| 2012/0288506 A1 | 11/2012 | Amatulli et al. |
| 2013/0149301 A1 | 6/2013 | Meade |
| 2013/0288373 A1 | 10/2013 | Verstraete et al. |
| 2014/0234320 A1 | 8/2014 | Croft et al. |
| 2014/0271688 A1 | 9/2014 | Abrams et al. |
| 2014/0294865 A1 | 10/2014 | Simon et al. |
| 2014/0314795 A1 | 10/2014 | Riddell et al. |
| 2014/0363437 A1 | 12/2014 | Reisner et al. |
| 2014/0369974 A1 | 12/2014 | Reisner et al. |
| 2014/0377284 A1 | 12/2014 | Simons et al. |
| 2015/0018408 A1 | 1/2015 | Lukacs et al. |
| 2015/0129000 A1 | 5/2015 | Jang et al. |
| 2015/0218220 A1 | 8/2015 | Mendelsohn et al. |
| 2015/0320880 A1 | 11/2015 | Abrams et al. |
| 2016/0002298 A1 | 1/2016 | Muller et al. |
| 2016/0008485 A1 | 1/2016 | Marquette et al. |
| 2016/0031902 A1 | 2/2016 | Fishkin |
| 2016/0120947 A1 | 5/2016 | Scadden et al. |
| 2016/0136298 A1 | 5/2016 | Grawunder et al. |
| 2016/0145335 A1 | 5/2016 | Damschroder et al. |
| 2016/0151515 A1 | 6/2016 | Joubert et al. |
| 2016/0152722 A1 | 6/2016 | Sharp et al. |
| 2016/0152733 A1 | 6/2016 | Thie et al. |
| 2016/0220687 A1 | 8/2016 | Alhamdan |
| 2016/0264680 A1 | 9/2016 | Poul et al. |
| 2016/0272716 A1 | 9/2016 | Lowe et al. |
| 2016/0311924 A1 | 10/2016 | Hadari et al. |
| 2016/0367699 A1 | 12/2016 | Jackson et al. |
| 2017/0021033 A1 | 1/2017 | Geierstanger et al. |
| 2017/0035905 A1 | 2/2017 | Abrams et al. |
| 2017/0112891 A1 | 4/2017 | Dragovich et al. |
| 2017/0158778 A1 | 6/2017 | Hadari et al. |
| 2017/0298137 A1 | 10/2017 | Jeffrey et al. |
| 2017/0340750 A1 | 11/2017 | Zhu et al. |
| 2018/0043033 A1 | 2/2018 | Anderl et al. |
| 2018/0194849 A1 | 7/2018 | Sahin et al. |
| 2018/0237495 A1 | 8/2018 | Gieffers et al. |
| 2018/0251565 A1 | 9/2018 | Harding et al. |
| 2018/0346519 A1 | 12/2018 | Werner-Simon et al. |
| 2019/0076548 A1* | 3/2019 | Hartigan ............ A61K 47/6831 |
| 2019/0100593 A1 | 4/2019 | Scadden et al. |

FOREIGN PATENT DOCUMENTS

| | | |
|---|---|---|
| EP | 1661584 A1 | 5/2006 |
| EP | 1859811 A1 | 11/2007 |
| EP | 719329 B1 | 1/2010 |
| EP | 3365448 A1 | 8/2018 |
| KR | 2004/0083918 A | 10/2004 |
| WO | WO-9315751 A1 | 8/1993 |
| WO | WO-9425621 A1 | 11/1994 |
| WO | WO-9513093 A1 | 5/1995 |
| WO | 96/29348 A1 | 9/1996 |
| WO | WO-9846264 A1 | 10/1998 |
| WO | WO-0061775 A1 | 10/2000 |
| WO | WO-00/66091 A1 | 11/2000 |
| WO | WO-0066090 A1 | 11/2000 |
| WO | WO-0066182 A1 | 11/2000 |
| WO | WO-0232955 A1 | 4/2002 |
| WO | WO-02088354 A1 | 11/2002 |
| WO | WO-2004045647 A1 | 6/2004 |
| WO | WO-2008/036374 A2 | 3/2008 |
| WO | WO-2009002993 A1 | 12/2008 |
| WO | WO-2010115629 A2 | 10/2010 |
| WO | WO-2010115630 A1 | 10/2010 |
| WO | WO-2012/047354 A2 | 4/2012 |
| WO | WO-2012041504 A1 | 4/2012 |
| WO | WO-2012047317 A2 | 4/2012 |
| WO | WO-2012/119787 A1 | 9/2012 |
| WO | WO-2013093919 A2 | 6/2013 |
| WO | WO-2013/173391 A1 | 11/2013 |
| WO | WO-2013/173392 A1 | 11/2013 |
| WO | WO-2013/173393 A1 | 11/2013 |
| WO | WO-2013/192546 A1 | 12/2013 |
| WO | WO-2014/009025 A1 | 1/2014 |
| WO | WO-2014/043403 A1 | 3/2014 |
| WO | WO-2014/044872 A1 | 3/2014 |
| WO | WO-2014/049366 A1 | 4/2014 |
| WO | WO-2014/062697 A2 | 4/2014 |
| WO | WO-2014/135282 A1 | 9/2014 |
| WO | WO-2014208987 A1 | 12/2014 |
| WO | WO-2015005431 A1 | 1/2015 |
| WO | WO-2016/001485 A1 | 1/2016 |
| WO | 2016/016442 A1 | 2/2016 |
| WO | WO-2016/033201 A1 | 3/2016 |
| WO | WO-2016/036334 A1 | 3/2016 |
| WO | 2016/054315 A1 | 4/2016 |
| WO | 2016/064749 A2 | 4/2016 |
| WO | WO-2016/059622 A2 | 4/2016 |
| WO | WO-2016/071856 A1 | 5/2016 |
| WO | WO-2016/077505 A2 | 5/2016 |
| WO | WO-2016/131769 A2 | 8/2016 |
| WO | WO-2016/141185 A1 | 9/2016 |
| WO | WO-2016/142049 A1 | 9/2016 |
| WO | WO-2016/145014 A1 | 9/2016 |
| WO | WO-2016/164502 A1 | 10/2016 |

(56) References Cited

FOREIGN PATENT DOCUMENTS

| | | | |
|---|---|---|---|
| WO | WO-2016/164745 A1 | 10/2016 | |
| WO | WO-2016/168471 A1 | 10/2016 | |
| WO | WO-2016/185403 A1 | 11/2016 | |
| WO | WO-2016/191186 A1 | 12/2016 | |
| WO | WO-2016/205738 A2 | 12/2016 | |
| WO | WO-2017/004127 A1 | 1/2017 | |
| WO | WO-2017/011803 A1 | 1/2017 | |
| WO | WO-2017/023753 A1 | 2/2017 | |
| WO | 2017/046658 A1 | 3/2017 | |
| WO | 2017/149077 A1 | 9/2017 | |
| WO | 2017/191579 A1 | 11/2017 | |
| WO | 2018/115466 A1 | 6/2018 | |
| WO | 2019/030171 A1 | 2/2019 | |

OTHER PUBLICATIONS

Edwards et al.; The Remarkable Flexibility of the Human Antibody Repertoire; Isolation of Over One Thousand Different Antibodies to a Single Protein, BLyS; Science Direct; pp. 103-118 (2003).

International Search Report and the Written Opinion of corresponding International Application No. PCT/US2017/038151; completed on Nov. 1, 2017; dated Nov. 20, 2017.

Lee et al. (2002) European J of Immunogenetics 29(5):449-452.

Lloyd et al. Modelling the Human Immune Response: Performance of a I 0 human antbody repertoire against a broad panel of therapeutically relevant antigens; Protein Engineering, Design and Selection; vol. 22, No. 3, pp. 159-168; 2009.

May et al., "Synthesis, Characterisation, and In Vitro Evaluation of Pro2-lle3-S-Deoxo-Amaninamide and Pro2-D-allo-lle3-S-Deoxo-Amaninamide: Implications for Structure-Activity Relationships in Amanitin Conformation and Toxicity," Chemistry: A European Journal, 2008, 14, 3410-3417.

Zanotti et al., "Structure-Toxicity Relationships in the Amatoxin Series," Int. J. Peptide Protein Res., 34, 1989, 222-228.

Zanotti et al., "Synthesis of Analogues of Amaninamide, an Amatoxin from the White Amanita Virosa Mushroom," Int. J. Peptide Protein Res., 30, 1987, 450-459.

Zhao et al., "Synthesis of a Cytotoxic Amanitin for Biorthogonal Conjugation," ChemBioChem. 2015, 16, 1420-1425.

CD137 antibody—Clone JG1.6A Biorad—Catalog No. MCA2653 <https://www.bio-rad-antibodies.com/monoclonal/human-cd137-antibody-jg1-6a-mca2653.html?f=purified>.

PE anti-human CD137 (4-1BB) Antibody, Clone 4B4-1, BioLegend—Catalog Number: 309803 <https://www.biolegend.com/en-us/products/pe-anti-human-cd137-4-1bb-antibody-1510>.

* cited by examiner

SEQUENCE LISTING

```
<160> NUMBER OF SEQ ID NOS: 38

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ser Thr Tyr Trp Ile Ser
1               5

<210> SEQ ID NO 2
<211> LENGTH: 17
<212> TYPE: PRT
<213> ORGANISM: Artificial Sequence
<220> FEATURE:
<223> OTHER INFORMATION: Description of Artificial Sequence: Synthetic
```

```
                           peptide

<400> SEQUENCE: 2

Lys Ile Tyr Pro Gly Asp Ser Tyr Thr Asn Tyr Ser Pro Ser Phe Gln
1               5                   10                  15

Gly

<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Arg Gly Tyr Gly Ile Phe Asp Tyr
1               5

<210> SEQ ID NO 4
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Ser Gly Asp Asn Ile Gly Asp Gln Tyr Ala His
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gln Asp Lys Asn Arg Pro Ser
1               5

<210> SEQ ID NO 6
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ala Thr Tyr Thr Gly Phe Gly Ser Leu Ala Val
1               5                   10

<210> SEQ ID NO 7
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ser Thr Tyr Thr Phe Val Gly Phe Thr Thr Val
1               5                   10
```

```
<210> SEQ ID NO 8
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Asn Ser Tyr Ala Ile Ser
1               5

<210> SEQ ID NO 9
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gly Ile Ile Pro Gly Phe Gly Thr Ala Asn Tyr Ala Gln Lys Phe Gln
1               5                   10                  15

Gly

<210> SEQ ID NO 10
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Arg Lys Asn Glu Glu Asp Gly Gly Phe Asp His
1               5                   10

<210> SEQ ID NO 11
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Ser Gly Asp Asn Leu Gly Asp Tyr Tyr Ala Ser
1               5                   10

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Asp Asp Ser Asn Arg Pro Ser
1               5

<210> SEQ ID NO 13
<211> LENGTH: 10
<212> TYPE: PRT
<213> ORGANISM: Artificial Sequence
<220> FEATURE:
<223> OTHER INFORMATION: Description of Artificial Sequence: Synthetic
```

```
peptide

<400> SEQUENCE: 13

Gln Thr Trp Asp Gly Thr Leu His Phe Val
1               5                   10

<210> SEQ ID NO 14
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ser Asp Tyr Tyr Met His
1               5

<210> SEQ ID NO 15
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Val Ile Ser Gly Ser Gly Ser Asn Thr Tyr Tyr Ala Asp Ser Val Lys
1               5                   10                  15

Gly

<210> SEQ ID NO 16
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Arg Leu Tyr Ala Gln Phe Glu Gly Asp Phe
1               5                   10

<210> SEQ ID NO 17
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Ser Gly Asp Asn Ile Gly Ser Lys Tyr Val Ser
1               5                   10

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Ser Asp Ser Glu Arg Pro Ser
1               5
```

```
<210> SEQ ID NO 19
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gln Ser Trp Asp Gly Ser Ile Ser Arg Val
1               5                   10

<210> SEQ ID NO 20
<211> LENGTH: 255
<212> TYPE: PRT
<213> ORGANISM: Homo sapiens

<400> SEQUENCE: 20

Met Gly Asn Ser Cys Tyr Asn Ile Val Ala Thr Leu Leu Leu Val Leu
1               5                   10                  15

Asn Phe Glu Arg Thr Arg Ser Leu Gln Asp Pro Cys Ser Asn Cys Pro
                20                  25                  30

Ala Gly Thr Phe Cys Asp Asn Asn Arg Asn Gln Ile Cys Ser Pro Cys
            35                  40                  45

Pro Pro Asn Ser Phe Ser Ser Ala Gly Gly Gln Arg Thr Cys Asp Ile
50                  55                  60

Cys Arg Gln Cys Lys Gly Val Phe Arg Thr Arg Lys Glu Cys Ser Ser
65                  70                  75                  80

Thr Ser Asn Ala Glu Cys Asp Cys Thr Pro Gly Phe His Cys Leu Gly
                85                  90                  95

Ala Gly Cys Ser Met Cys Glu Gln Asp Cys Lys Gln Gly Gln Glu Leu
                100                 105                 110

Thr Lys Lys Gly Cys Lys Asp Cys Cys Phe Gly Thr Phe Asn Asp Gln
            115                 120                 125

Lys Arg Gly Ile Cys Arg Pro Trp Thr Asn Cys Ser Leu Asp Gly Lys
130                 135                 140

Ser Val Leu Val Asn Gly Thr Lys Glu Arg Asp Val Val Cys Gly Pro
145                 150                 155                 160

Ser Pro Ala Asp Leu Ser Pro Gly Ala Ser Ser Val Thr Pro Pro Ala
                165                 170                 175

Pro Ala Arg Glu Pro Gly His Ser Pro Gln Ile Ile Ser Phe Phe Leu
            180                 185                 190

Ala Leu Thr Ser Thr Ala Leu Leu Phe Leu Leu Phe Phe Leu Thr Leu
        195                 200                 205

Arg Phe Ser Val Val Lys Arg Gly Arg Lys Lys Leu Leu Tyr Ile Phe
210                 215                 220

Lys Gln Pro Phe Met Arg Pro Val Gln Thr Thr Gln Glu Glu Asp Gly
225                 230                 235                 240

Cys Ser Cys Arg Phe Pro Glu Glu Glu Glu Gly Gly Cys Glu Leu
                245                 250                 255

<210> SEQ ID NO 21
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide
```

-continued

```
<400> SEQUENCE: 21

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Ala Met Ser Trp Val Arg Gln Ala Pro Gly Lys Gly Leu Glu Trp Val
        35                  40                  45

Ala Val Ile Ser Glu Asn Gly Ser Asp Thr Tyr Tyr Ala Asp Ser Val
    50                  55                  60

Lys Gly Arg Phe Thr Ile Ser Arg Asp Asp Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Gly Ala Val Ser Tyr Phe Asp Val Trp Gly Gln
            100                 105                 110

Gly Thr Leu Val Thr Val Ser Ser
        115                 120

<210> SEQ ID NO 22
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Leu Pro Tyr
                85                  90                  95

Thr Phe Gly Gln Gly Thr Lys Val Glu Ile Lys Arg Thr
            100                 105

<210> SEQ ID NO 23
<211> LENGTH: 453
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Gln Val Gln Leu Gln Gln Pro Gly Ala Glu Leu Val Arg Pro Gly Ala
1               5                   10                  15

Ser Val Lys Leu Ser Cys Lys Ala Ser Gly Tyr Thr Phe Thr Ser Tyr
            20                  25                  30

Trp Ile Asn Trp Val Lys Gln Arg Pro Gly Gln Gly Leu Glu Trp Ile
        35                  40                  45

Gly Asn Ile Tyr Pro Ser Asp Ser Tyr Thr Asn Tyr Asn Gln Lys Phe
```

```
            50                  55                  60
Lys Asp Lys Ala Thr Leu Thr Val Asp Lys Ser Ser Asn Thr Val Tyr
 65                  70                  75                  80

Met Gln Leu Asn Ser Pro Thr Ser Glu Asp Ser Ala Val Tyr Tyr Cys
                     85                  90                  95

Thr Arg Asn Gly Val Glu Gly Tyr Pro His Tyr Tyr Ala Met Glu Tyr
                    100                 105                 110

Trp Gly Gln Gly Thr Ser Val Thr Val Ser Ser Ala Ser Thr Lys Gly
                    115                 120                 125

Pro Ser Val Phe Pro Leu Ala Pro Ser Ser Lys Ser Thr Ser Gly Gly
                    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                    165                 170                 175

Pro Ala Val Leu Gln Ser Ser Gly Leu Tyr Ser Leu Ser Ser Val Val
                    180                 185                 190

Thr Val Pro Ser Ser Ser Leu Gly Thr Gln Thr Tyr Ile Cys Asn Val
                    195                 200                 205

Asn His Lys Pro Ser Asn Thr Lys Val Asp Lys Lys Val Glu Pro Lys
210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                    245                 250                 255

Leu Met Ile Ser Arg Thr Pro Glu Val Thr Cys Val Val Val Asp Val
                    260                 265                 270

Ser His Glu Asp Pro Glu Val Lys Phe Asn Trp Tyr Val Asp Gly Val
                    275                 280                 285

Glu Val His Asn Ala Lys Thr Lys Pro Arg Glu Glu Gln Tyr Asn Ser
                    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                    325                 330                 335

Pro Ile Glu Lys Thr Ile Ser Lys Ala Lys Gly Gln Pro Arg Glu Pro
                    340                 345                 350

Gln Val Tyr Thr Leu Pro Pro Ser Arg Asp Glu Leu Thr Lys Asn Gln
                    355                 360                 365

Val Ser Leu Thr Cys Leu Val Lys Gly Phe Tyr Pro Ser Asp Ile Ala
                    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                    405                 410                 415

Thr Val Asp Lys Ser Arg Trp Gln Gln Gly Asn Val Phe Ser Cys Ser
                    420                 425                 430

Val Met His Glu Ala Leu His Asn His Tyr Thr Gln Lys Ser Leu Ser
                    435                 440                 445

Leu Ser Pro Gly Lys
            450

<210> SEQ ID NO 24
```

```
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Asp Ile Gln Met Thr Gln Thr Thr Ser Ala Leu Ser Ala Ser Leu Gly
1               5                   10                  15

Asp Arg Val Thr Ile Gly Cys Arg Ala Ser Gln Asp Leu Ser Asn His
            20                  25                  30

Leu Tyr Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Thr Ile Arg Asn Leu Glu Gln
65                  70                  75                  80

Glu Asp Val Ala Thr Tyr Phe Cys Gln Gln Gly Tyr Thr Leu Pro Tyr
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 25
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Ser Tyr Trp Ile Asn
1               5

<210> SEQ ID NO 26
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Asn Ile Tyr Pro Ser Asp Ser Tyr Thr Asn Tyr Asn Gln Lys Phe Lys
1               5                   10                  15
```

Asp

<210> SEQ ID NO 27
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Asn Gly Val Glu Gly Tyr Pro His Tyr Tyr Ala Met Glu Tyr
1               5                   10

<210> SEQ ID NO 28
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Gln Val Gln Leu Gln Gln Pro Gly Ala Glu Leu Val Arg Pro Gly Ala
1               5                   10                  15

Ser Val Lys Leu Ser Cys Lys Ala Ser Gly Tyr Thr Phe Thr Ser Tyr
            20                  25                  30

Trp Ile Asn Trp Val Lys Gln Arg Pro Gly Gln Gly Leu Glu Trp Ile
        35                  40                  45

Gly Asn Ile Tyr Pro Ser Asp Ser Tyr Thr Asn Tyr Asn Gln Lys Phe
    50                  55                  60

Lys Asp Lys Ala Thr Leu Thr Val Asp Lys Ser Ser Asn Thr Val Tyr
65                  70                  75                  80

Met Gln Leu Asn Ser Pro Thr Ser Glu Asp Ser Ala Val Tyr Tyr Cys
                85                  90                  95

Thr Arg Asn Gly Val Glu Gly Tyr Pro His Tyr Tyr Ala Met Glu Tyr
            100                 105                 110

Trp Gly Gln Gly Thr Ser Val Thr Val Ser Ser
        115                 120

<210> SEQ ID NO 29
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Arg Ala Ser Gln Asp Leu Ser Asn His Leu Tyr
1               5                   10

<210> SEQ ID NO 30
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Tyr Thr Ser Arg Leu His Ser
1               5

```
<210> SEQ ID NO 31
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Gln Gln Gly Tyr Thr Leu Pro Tyr Thr
1               5

<210> SEQ ID NO 32
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Asp Ile Gln Met Thr Gln Thr Thr Ser Ala Leu Ser Ala Ser Leu Gly
1               5                   10                  15

Asp Arg Val Thr Ile Gly Cys Arg Ala Ser Gln Asp Leu Ser Asn His
            20                  25                  30

Leu Tyr Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Thr Ile Arg Asn Leu Glu Gln
65                  70                  75                  80

Glu Asp Val Ala Thr Tyr Phe Cys Gln Gln Gly Tyr Thr Leu Pro Tyr
                85                  90                  95

Thr Phe Gly Gly Gly Thr Lys Leu Glu Ile Lys
            100                 105

<210> SEQ ID NO 33
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Ser Gly Tyr Thr Phe Thr Ser Tyr Trp
1               5

<210> SEQ ID NO 34
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Asn Ile Tyr Pro Ser Asp Ser Tyr Thr
1               5

<210> SEQ ID NO 35
<211> LENGTH: 15
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 35

Thr Arg Asn Gly Val Glu Gly Tyr Pro His Tyr Tyr Ala Met Glu
1               5                   10                  15

<210> SEQ ID NO 36
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Ser Gln Asp Leu Ser Asn His
1               5

<210> SEQ ID NO 37
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Tyr Tyr Thr Ser
1

<210> SEQ ID NO 38
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Cys Gln Gln Gly Tyr Thr Leu Pro Tyr
1               5
```

COMPOSITIONS AND METHODS FOR THE DEPLETION OF CD137+ CELLS

RELATED APPLICATIONS

This application claims priority to U.S. Provisional Application No. 62/448,741, filed on Jan. 20, 2017, and U.S. Provisional Application No. 62/595,977, filed on Dec. 7, 2017. The contents of the aforementioned applications are incorporated by reference herein in their entirety.

SEQUENCE LISTING

The instant application contains a Sequence Listing which has been submitted electronically in ASCII format and is hereby incorporated by reference in its entirety. Said ASCII copy, created on Jan. 19, 2018, is named M1030341030US_SL.txt and is 20,422 bytes in size.

FIELD OF THE INVENTION

The present invention relates to the field of transplant therapy and provides methods for the treatment of autoimmune diseases and graft-versus-host disease (GVHD) by administration of antibodies, antibody-drug conjugates, and ligand-drug conjugates capable of binding an antigen expressed by hematopoietic cells.

BACKGROUND OF THE INVENTION

While hematopoietic stem cells have significant therapeutic potential, a limitation that has hindered their use in the clinic has been the development of graft-versus-host disease (GVHD) some days or weeks after the cell transplant. While significant advances have been made with regard to the treatment of GVHD following transplantation, there is still a need in the art for improved methods, particularly with respect to reducing mortality rates from GVHD. Conventional treatment of GVHD requires systemic immunosuppressive therapy with potent drugs such as corticosteroids and cyclosporine. Agents such as mycophenolate mofetil, rapamycin (sirolimus), imatinib, and rituximab are used in patients with steroid-refractory GVHD. However, these treatments have limited efficacy and often cause severe adverse effects. Only 50% of patients with GVHD are able to discontinue immunosuppressive treatment within 5 years after diagnosis, and 10% require continued treatment beyond 5 years. The remaining 40% die or develop recurrent malignancy before GVHD resolves. Five year survival rates of patients with high risk GVHD (platelet counts <100,000/microliter or progressive onset from GVHD) is only 40-50%. Thus, the development of innovative strategies to prevent and treat GVHD represents an important unmet clinical need.

Like, GVHD, autoimmune diseases such as multiple sclerosis, rheumatoid arthritis, intestinal bowel disease, psoriasis, lupus, and Type 1 diabetes are characterized by an abnormal immune response directed against normal self tissues. Autoimmune diseases are characterized by production of autoreactive T cells and antibodies reactive with host tissues (autoantibodies). Traditional therapies for autoimmune disease include immunosuppressive agents that globally dampen immune responses. The benefits of such agents are often tempered by susceptibility to opportunistic infections, long-term risk of malignancy, toxicity and other unfavorable side effects. Thus, there is a need to develop a strategy to more specifically target the cellular mediators of both GVHD and autoimmune diseases.

SUMMARY OF THE INVENTION

The present invention provides methods for preventing and treating acute and chronic forms of graft-versus-host disease (GVHD) and autoimmune diseases in a patient such as a human patient, receiving hematopoietic stem cell transplant therapy so as to reduce the morbidity and mortality associated with GVHD and autoimmune diseases. The invention additionally features methods of treating a variety of hematopoietic conditions, such as sickle cell anemia, thalassemia, Fanconi anemia, Wiskott-Aldrich syndrome, adenosine deaminase deficiency-severe combined immunodeficiency, metachromatic leukodystrophy, Diamond-Blackfan anemia and Schwachman-Diamond syndrome, human immunodeficiency virus infection, and acquired immune deficiency syndrome, among others. The invention features methods of treating a patient with antibodies, antibody-drug conjugates, ligands, and ligand-drug conjugates capable of binding proteins expressed by hematopoietic cells, such as CD137, so as to deplete a population of hematopoietic cells, such as T cells, within the patient. This selective depletion of T cells in turn improves overall and relapse-free patient survival while significantly decreasing GVHD and autoimmune diseases.

In a first aspect, the invention features a method of treating GVHD in a human patient in need thereof by administering to the patient an effective amount of an antibody, or antigen-binding fragment thereof, or an antibody drug conjugate (ADC), capable of binding CD137, wherein the antibody or antigen-binding fragment thereof is conjugated to a cytotoxin via a linker.

In a second aspect, the invention provides a method of depleting a population of CD137+ cells in a human patient suffering from or at risk for GVHD by administering to the patient an effective amount of an antibody, or antigen-binding fragment thereof, or an antibody drug conjugate (ADC), capable of binding CD137, wherein the antibody or antigen-binding fragment thereof is conjugated to a cytotoxin via a linker.

In a third aspect, the invention features a method of treating an autoimmune disease in a human patient in need thereof by administering to the patient an effective amount of an antibody, or antigen-binding fragment thereof, or antibody drug conjugate (ADC), capable of binding CD137, wherein the antibody or antigen-binding fragment thereof is conjugated to a cytotoxin via a linker.

In a fourth aspect, the invention provides a method of depleting a population of CD137+ cells in a human patient suffering from or at risk for an autoimmune disease by administering to the patient an effective amount of an antibody, or antigen-binding fragment thereof, or an antibody drug conjugate (ADC), capable of binding CD137, wherein the antibody or antigen-binding fragment thereof is conjugated to a cytotoxin via a linker.

In some embodiments, the antibody, or antigen-binding fragment thereof is selected from the group consisting of a monoclonal antibody or antigen-binding fragment thereof, a polyclonal antibody or antigen-binding fragment thereof, a humanized antibody or antigen-binding fragment thereof, a bispecific antibody or antigen-binding fragment thereof, a dual-variable immunoglobulin domain, a single-chain Fv molecule (scFv), a diabody, a triabody, a nanobody, an antibody-like protein scaffold, a Fv fragment, a Fab fragment, a F(ab')$_2$ molecule, and a tandem di-scFv.

In some embodiments, the antibody, or antigen-binding fragment thereof binds human CD137 extracellular domain at an epitope located within amino acid residues 115-156 of SEQ ID NO: 20. SEQ ID NO: 20 corresponds to the extracellular domain of CD137 and has the following amino acid sequence:

(SEQ ID NO: 20)
MGNSCYNIVATLLLVLNFERTRSLQDPCSNCPAGTFCDNNRNQICSPCPP

NSFSSAGGQRTCDICRQCKGVFRTRKECSSTSNAECDCTPGFHCLGAGCS

MCEQDCKQGQELTKKGCKDCCFGTFTDQKRGICRPWTNCSLDGKSVLVNG

TKERDVVCGPSPADLSPGASSVTPPAPAREPGHSPQIISFFLALTSTALL

FLLFFLTLRFSVVKRGRKKLLYIFKQPFMRPVQTTQEEDGCSCRFPEEEE

GGCEL

In some embodiments, the antibody has an isotype selected from the group consisting of IgG, IgA, IgM, IgD, and IgE.

In some embodiments, the Fc domain is a human IgG1 isotype Fc domain. In some embodiments, the Fc domain is a human IgG2 isotype Fc domain. In some embodiments, the Fc domain is a human IgG3 isotype Fc domain. In some embodiments, the Fc domain is a human IgG4 isotype Fc domain.

In another aspect, the invention features a method of treating GVHD in a human patient in need thereof, the method comprising administering to the patient an effective amount of a soluble CD137 ligand.

In another aspect, the invention features a method of depleting a population of CD137 positive cells in a human patient suffering from or at risk for GVHD, the method comprising administering to the patient an effective amount of a soluble CD137 ligand.

In another aspect, the invention features a method of treating an autoimmune disease in a human patient in need thereof, by administering to the patient an effective amount of a soluble CD137 ligand.

In another aspect, the invention features a method of depleting a population of CD137 positive cells in a human patient suffering from or at risk for an autoimmune disease, by administering to the patient an effective amount of a soluble CD137 ligand.

In some embodiments, the antibody or antigen-binding fragment thereof is conjugated to a cytotoxin, such as a microtubule-binding agent. In some embodiments, the antibody or antigen-binding fragment thereof, or soluble CD137 ligand is conjugated to a microtubule-binding agent by way of a linker. In yet other embodiments, the antibody or antigen-binding fragment thereof is conjugated to a cytotoxin, wherein the cytotoxin is a microtubule-binding agent.

In some embodiments, the microtubule-binding agent is a maytansine.

In some embodiments, the microtubule-binding agent is a maytansinoid.

In some embodiments, the microtubule-binding agent is a maytansine or a maytansinoid.

In some embodiments, the maytansinoid is selected from the group consisting of DM1, DM3, and DM4, and maytansinol.

In some embodiments, the maytansinoid is a maytansinol analog.

In some embodiments, the antibody, antigen-binding fragment thereof, ADC, or soluble CD137 ligand is delivered into the patient prior to the patient receiving a transplant comprising hematopoietic stem cells.

In some embodiments, the antibody, antigen-binding fragment thereof, ADC, or soluble CD137 ligand conjugated to a cytotoxin, such as a microtubule binding agent, is delivered into the patient about 3 days (for example, from 1 hour to 7 days (e.g., 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, 2 days, 3 days, 4 days, 5 days, 6 days, or 7 days) prior to administration of the hematopoietic stem cells into the patient.

In some embodiments, the antibody, antigen-binding fragment thereof, ADC, or soluble CD137 ligand is delivered into the patient concomitant with the patient receiving a transplant that includes hematopoietic stem cells.

In some embodiments, the antibody, antigen-binding fragment thereof, ADC, or soluble CD137 ligand is delivered into the patient after the patient receives a transplant comprising hematopoietic stem cells.

In some embodiments, the antigen-binding fragment thereof, ADC, or soluble CD137 ligand (e.g., conjugated to a cytotoxin, such as a microtubule binding agent) is delivered into the patient, for example, about 1 hour to 10 days (e.g., 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, 2 days, 3 days, 4 days, 5 days, 6 days, 7 days, 8 days, 9 days, or 10 days) or more after the administration of the exogenous hematopoietic stem cell transplant. For example, the antibody, antigen-binding fragment thereof, drug-antibody conjugate, or drug-ligand conjugate may be administered about 3 to 4 days after the transplant.

In some embodiments, the transplant is allogeneic. In some embodiments, the transplant is autologous.

In some embodiments, the transplant is a bone marrow transplant, a peripheral blood transplant, or a cord blood transplant.

In some embodiments, the transplant includes hematopoietic cells (e.g., hematopoietic stem cells).

In some embodiments, the hematopoietic stem cells or progeny thereof maintain hematopoietic stem cell functional potential after two or more days following transplantation of hematopoietic stem cells into the patient.

In some embodiments, the hematopoietic stem cells or progeny thereof maintain hematopoietic stem cell functional potential after two or more days (for example, from about 2 to about 5 days, from about 2 to about 7 days, from about 2 to about 20 days, from about 2 to about 30 days, such as 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, or more) following transplantation of the hematopoietic stem cells into the patient.

In some embodiments, the hematopoietic stem cells or progeny thereof are capable of localizing to hematopoietic tissue, such as the bone marrow, and/or reestablishing hematopoiesis following transplantation of the hematopoietic stem cells into the patient.

In some embodiments, upon transplantation into the patient, the hematopoietic stem cells give rise to recovery of a population of cells selected from the group consisting of megakaryocytes, thrombocytes, platelets, erythrocytes, mast cells, myeoblasts, basophils, neutrophils, eosinophils, microglia, granulocytes, monocytes, osteoclasts, antigen-presenting cells, macrophages, dendritic cells, natural killer cells, T cells and B cells.

In some embodiments, the transplant comprises leukocytes.

In some embodiments, upon transplantation into the patient, the hematopoietic cells are selected from the group consisting of T cells, B cells, dendritic cells, natural killer (NK) cells, macrophages, cancer cells, neutrophils, basophils, and eosinophils.

In some embodiments, the invention provides a method of depleting a population of CD137+ cells in a human patient suffering from or at risk for GVHD by administering to the patient an effective amount of an antibody, or antigen-binding fragment, ADC, or soluble CD137 ligand capable of binding CD137 and is conjugated to a cytotoxin such as a microtubule-binding agent, wherein the hematopoietic cells comprising CD137+ cells are selected from the group consisting of T cells, B cells, dendritic cells, natural killer (NK) cells, macrophages, cancer cells, neutrophils, basophils, and eosinophils.

In some embodiments, CD137+ cells selected from the group consisting of T cells, B cells, dendritic cells, natural killer (NK) cells, macrophages, cancer cells, neutrophils, basophils, and eosinophils demonstrate reactivity against an antigen of the patient.

In some embodiments, the antibody, antigen-binding fragment thereof, ADC, or soluble CD137 ligand is internalized by a CD137+ cell following administration to the patient. For instance, the antibody, antigen-binding fragment thereof, ADC, or soluble CD137 ligand may be internalized by a CD137+ T cell by receptor mediated endocytosis (e.g., upon binding to cell-surface CD137). In some embodiments, a cytotoxin covalently bound to the antibody, antigen-binding fragment thereof, or ADC, may be released intracellularly by chemical cleavage (for instance, by enzymatic or non-specific cleavage of a linker described herein). The cytotoxin may then access its intracellular target (such as the mitotic spindle apparatus, nuclear DNA, ribosomal RNA, or topoisomerases, among others) so as to promote the death of a CD137+ T cell.

In some embodiments, the antibody, antigen-binding fragment thereof, ADC, or soluble CD137 ligand is capable of promoting mitotic arrest and suppressing proliferation (for instance, by suppressing microtubule dynamic instability) of the CD137+ T cell.

In some embodiments, the antibody, antigen-binding fragment thereof, ADC, or soluble CD137 ligand may promote the death of a cell by recruiting one or more complement proteins, natural killer (NK) cells, macrophages, neutrophils, and/or eosinophils upon administration to the patient.

In some embodiments, the antibody, antigen-binding fragment thereof, ADC, or soluble CD137 ligand may promote the death of a CD137+ T cell by recruiting one or more complement proteins, natural killer (NK) cells, macrophages, neutrophils, and/or eosinophils upon administration to the patient.

In some embodiments, the antibody or antigen-binding fragment thereof or soluble CD137 ligand is used to treat a T- or B cell-driven autoimmune disease.

In some embodiments, the autoimmune disease is multiple sclerosis, rheumatoid arthritis, intestinal bowel disease, psoriasis, lupus, or Type 1 diabetes.

In some embodiments, the method is used to treat one or more disorders or cancers in a patient, such as a patient that has received a transplant comprising hematopoietic stem cells. For instance, the patient may be one that is suffering from a stem cell disorder. In some embodiments, the patient is suffering from a hemoglobinopathy disorder, such as sickle cell anemia, thalassemia, Fanconi anemia, and Wiskott-Aldrich syndrome. The patient may be suffering from an immunodeficiency disorder, such as a congenital immunodeficiency disorder or an acquired immunodeficiency disorder (e.g., human immunodeficiency virus or acquired immune deficiency syndrome). In some embodiments, the patient is suffering from a metabolic disorder, such as glycogen storage diseases, mucopolysaccharidoses, Gaucher's Disease, Hurlers Disease, sphingolipidoses, and metachromatic leukodystrophy. In some embodiments, the patient is suffering from cancer, such as leukemia, lymphoma, multiple myeloma and myelodysplastic syndrome, and neuroblastoma. In some embodiments, the patient is suffering from a disorder selected from the group consisting of adenosine deaminase deficiency and severe combined immunodeficiency, hyper immunoglobulin M syndrome, Chediak-Higashi disease, hereditary lymphohistiocytosis, osteopetrosis, osteogenesis imperfecta, storage diseases, thalassemia major, systemic sclerosis, systemic lupus erythematosus, multiple sclerosis, and juvenile rheumatoid arthritis.

In a further aspect, the invention features a method of treating graft versus host disease (GVHD) in a human patient in need thereof, by administering an anti-CD137 antibody drug conjugate (ADC) to the human patient such that GVHD is treated, wherein the ADC comprises an anti-CD137 antibody linked to a cytotoxin which is a microtubule-binding agent or an RNA polymerase inhibitor. In one embodiment, the method comprises administering the ADC to the patient prior to the patient receiving a transplant comprising hematopoietic stem cells. In another embodiment, the method comprising administering the ADC to the patient about three days prior to the patient receiving a transplant comprising hematopoietic stem cells. In another embodiment, the method comprises administering the ADC to the patient concomitant with the patient receiving a transplant comprising hematopoietic stem cells. In a further embodiment, the method comprises administering the ADC to the patient after the patient receives a transplant comprising hematopoietic stem cells. In yet another embodiment, the method comprises administering the ADC to the patient about 1 hour to 10 days after the patient receives a transplant comprising hematopoietic stem cells. In a further embodiment, the method comprises administering the ADC to the patient about 3 to 4 days after the patient receives a transplant comprising hematopoietic stem cells. In other embodiments, the transplant is allogeneic.

In yet another aspect, the invention features a method of depleting a population of CD137 positive cells in a human subject having GVHD or at risk of developing GVHD, by administering an anti-CD137 ADC to the human patient such that GVHD the population of CD137 cells is depleted, wherein the ADC comprises an anti-CD137 antibody linked to a cytotoxin which is a microtubule-binding agent or an RNA polymerase inhibitor. In one embodiment, the method comprises administering the ADC to the patient prior to the patient receiving a transplant comprising hematopoietic stem cells. In another embodiment, the method comprises administering the ADC to the patient about three days prior to the patient receiving a transplant comprising hematopoietic stem cells. In another embodiment, the method comprises administering the ADC to the patient concomitant with the patient receiving a transplant comprising hematopoietic stem cells. In a further embodiment, the method comprises administering the ADC to the patient after the patient receives a transplant comprising hematopoietic stem cells. In yet another embodiment, the method comprises administering the ADC to the patient about 1 hour to 10 days after the patient receives a transplant comprising hematopoietic stem cells. In a further embodiment, the method comprises administering the ADC to the patient about 3 to 4 days after the patient receives a transplant comprising hematopoietic stem cells. In other embodiments, the transplant is allogeneic. In other embodiments, the microtubule-binding agent is a maytansinoid. In other embodiments, the RNA polymerase inhibitor is an amatoxin. In certain embodiments, the amatoxin is represented by formula (IVA)

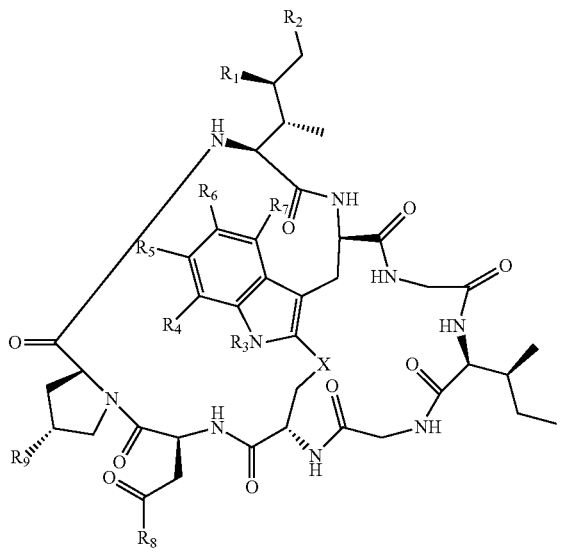

(IVA)

wherein $R_1$ is H, OH, $OR_A$, or $OR_C$;
$R_2$ is H, OH, $OR_B$, or $OR_C$;
$R_A$ and $R_B$, together with the oxygen atoms to which they are bound, combine to form an optionally substituted 5-membered heterocycloalkyl group;
$R_3$ is H, $R_C$, or $R_D$;
$R_4$, $R_5$, $R_6$, and $R_7$ are each independently H, OH, $OR_C$, $OR_D$, $R_C$, or $R_D$;
$R_8$ is OH, $NH_2$, $OR_C$, $OR_D$, $NHR_C$, or $NR_CR_D$;
$R_9$ is H, OH, $OR_C$, or $OR_D$;
X is —S—, —S(O)—, or —SO$_2$—;
$R_C$ is -L-Z;
$R_D$ is optionally substituted $C_1$-$C_6$ alkyl, optionally substituted $C_1$-$C_6$ heteroalkyl, optionally substituted $C_2$-$C_6$ alkenyl, optionally substituted $C_2$-$C_6$ heteroalkenyl, optionally substituted $C_2$-$C_6$ alkynyl, optionally substituted $C_2$-$C_6$ heteroalkynyl, optionally substituted cycloalkyl, optionally substituted heterocycloalkyl, optionally substituted aryl, or optionally substituted heteroaryl;
L is optionally substituted $C_1$-$C_6$ alkylene, optionally substituted $C_1$-$C_6$ heteroalkylene, optionally substituted $C_2$-$C_6$ alkenylene, optionally substituted $C_2$-$C_6$ heteroalkenylene, optionally substituted $C_2$-$C_6$ alkynylene, optionally substituted $C_2$-$C_6$ heteroalkynylene, optionally substituted cycloalkylene, optionally substituted heterocycloalkylene, optionally substituted arylene, or optionally substituted heteroarylene; and
Z is a chemical moiety formed from a coupling reaction between a reactive substituent present on L and a reactive substituent present within the antibody or antigen-binding fragment thereof,
wherein Am comprises exactly one $R_C$ substituent. In yet other embodiments, the amatoxin is represented by formula (IVB)

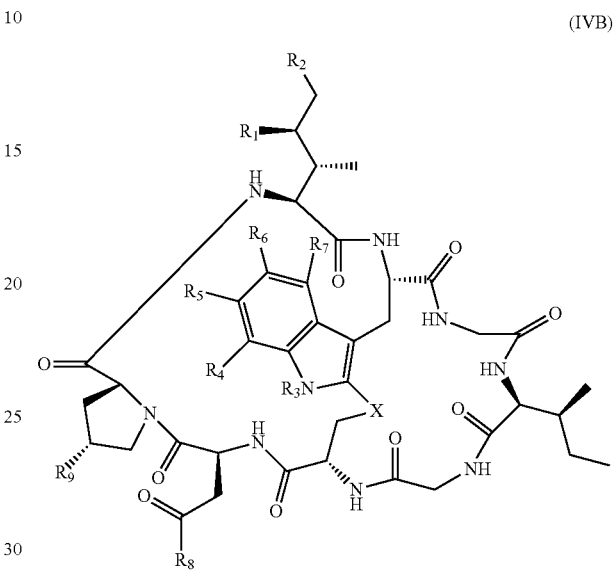

(IVB)

wherein $R_1$ is H, OH, $OR_A$, or $OR_C$;
$R_2$ is H, OH, $OR_B$, or $OR_C$;
$R_A$ and $R_B$, together with the oxygen atoms to which they are bound, combine to form an optionally substituted 5-membered heterocycloalkyl group;
$R_3$ is H, $R_C$, or $R_D$;
$R_4$, $R_5$, $R_6$, and $R_7$ are each independently H, OH, $OR_C$, $OR_D$, $R_C$, or $R_D$;
$R_8$ is OH, $NH_2$, $OR_C$, $OR_D$, $NHR_C$, or $NR_CR_D$;
$R_9$ is H, OH, $OR_C$, or $OR_D$;
X is —S—, —S(O)—, or —SO$_2$—;
$R_C$ is -L-Z;
$R_D$ is optionally substituted $C_1$-$C_6$ alkyl, optionally substituted $C_1$-$C_6$ heteroalkyl, optionally substituted $C_2$-$C_6$ alkenyl, optionally substituted $C_2$-$C_6$ heteroalkenyl, optionally substituted $C_2$-$C_6$ alkynyl, optionally substituted $C_2$-$C_6$ heteroalkynyl, optionally substituted cycloalkyl, optionally substituted heterocycloalkyl, optionally substituted aryl, or optionally substituted heteroaryl;
L is optionally substituted $C_1$-$C_6$ alkylene, optionally substituted $C_1$-$C_6$ heteroalkylene, optionally substituted $C_2$-$C_6$ alkenylene, optionally substituted $C_2$-$C_6$ heteroalkenylene, optionally substituted $C_2$-$C_6$ alkynylene, optionally substituted $C_2$-$C_6$ heteroalkynylene, optionally substituted cycloalkylene, optionally substituted heterocycloalkylene, optionally substituted arylene, or optionally substituted heteroarylene; and
Z is a chemical moiety formed from a coupling reaction between a reactive substituent present on L and a reactive substituent present within the antibody or antigen-binding fragment thereof,
wherein Am comprises exactly one $R_C$ substituent.
In other embodiments, the ADC comprises an anti-CD137 antibody conjugated to a cytotoxin which is an RNA polymerase inhibitor, e.g., an amanitin. In one embodiment, the amanitin is α-amanitin, β-amanitin, γ-amanitin, ε-amanitin, amanin, amaninamide, amanullin, amanullinic acid, or proamanullin.

In another aspect, the invention features a method of depleting allo-reactive T cells in a human patient who received an allogenic transplant, by administering an anti-CD137 ADC to the human patient such allo-reactive T cells are depleted, wherein the ADC comprises an anti-CD137 antibody linked to a cytotoxin. In certain embodiments, the transplant is a bone marrow transplant. In other embodiments, the transplant is a peripheral blood transplant. In yet other embodiments, the transplant is a cord blood transplant. In other embodiments, the transplant comprises hematopoietic cells. In certain embodiments, the hematopoietic stem cells or progeny thereof maintain hematopoietic stem cell functional potential after two or more days following transplantation of the hematopoietic stem cells into the patient. In other embodiments, the cytotoxin is an RNA polymerase inhibitor. In another embodiment, the RNA polymerase inhibitor is an amatoxin. In other embodiments, the anti-CD137 antibody comprises the CDRs of antibody BBK2 as defined by Kabat numbering. In another embodiment, the anti-CD137 antibody comprises the heavy and light chain variable regions of antibody BBK2 (as described in Lee, et al. *Eur J Immunogenet.* 2002 October; 29(5):449-52, incorporated herein by reference in its entirety). In other embodiments, the anti-CD137 antibody is chimeric BBK2. In other embodiments, the anti-CD137 antibody comprises a heavy chain sequence comprising SEQ ID NO: 23 and a light chain sequence comprising SEQ ID NO: 24. In yet other embodiments, the anti-CD137 antibody is an antagonist antibody.

In other embodiments, the anti-CD137 antibody is an IgG1 or an IgG4. In certain embodiments, the anti-CD137 antibody is an intact antibody.

In one embodiment, the microtubule-binding agent used in the methods and compositions described herein is a maytansinoid.

In other embodiments, the RNA polymerase inhibitor used in the methods and compositions described herein is an amatoxin. In certain embodiments, the amatoxin is represented by formula (IVA)

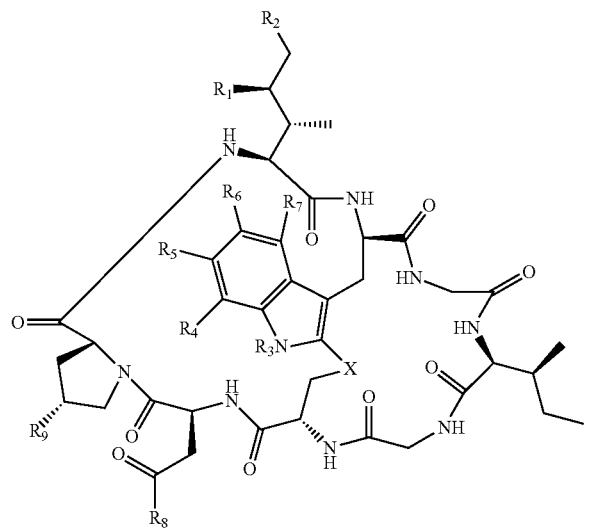

(IVA)

wherein $R_1$ is H, OH, $OR_A$, or $OR_C$;
$R_2$ is H, OH, $OR_B$, or $OR_C$;
$R_A$ and $R_B$, together with the oxygen atoms to which they are bound, combine to form an optionally substituted 5-membered heterocycloalkyl group;
$R_3$ is H, $R_C$, or $R_D$;
$R_4$, $R_5$, $R_6$, and $R_7$ are each independently H, OH, $OR_C$, $OR_D$, $R_C$, or $R_D$;
$R_8$ is OH, $NH_2$, $OR_C$, $OR_D$, $NHR_C$, or $NR_CR_D$;
$R_9$ is H, OH, $OR_C$, or $OR_D$;
X is —S—, —S(O)—, or —SO$_2$—;
$R_C$ is -L-Z;
$R_D$ is optionally substituted $C_1$-$C_6$ alkyl, optionally substituted $C_1$-$C_6$ heteroalkyl, optionally substituted $C_2$-$C_6$ alkenyl, optionally substituted $C_2$-$C_6$ heteroalkenyl, optionally substituted $C_2$-$C_6$ alkynyl, optionally substituted $C_2$-$C_6$ heteroalkynyl, optionally substituted cycloalkyl, optionally substituted heterocycloalkyl, optionally substituted aryl, or optionally substituted heteroaryl;
L is optionally substituted $C_1$-$C_6$ alkylene, optionally substituted $C_1$-$C_6$ heteroalkylene, optionally substituted $C_2$-$C_6$ alkenylene, optionally substituted $C_2$-$C_6$ heteroalkenylene, optionally substituted $C_2$-$C_6$ alkynylene, optionally substituted $C_2$-$C_6$ heteroalkynylene, optionally substituted cycloalkylene, optionally substituted heterocycloalkylene, optionally substituted arylene, or optionally substituted heteroarylene; and
Z is a chemical moiety formed from a coupling reaction between a reactive substituent present on L and a reactive substituent present within the antibody or antigen-binding fragment thereof,
wherein Am comprises exactly one $R_C$ substituent. In yet other embodiments, the amatoxin is represented by formula (IVB)

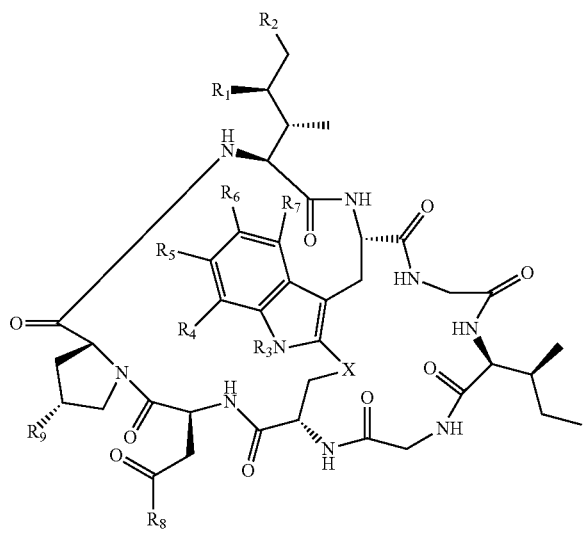

(IVB)

wherein $R_1$ is H, OH, $OR_A$, or $OR_C$;
$R_2$ is H, OH, $OR_B$, or $OR_C$;
$R_A$ and $R_B$, together with the oxygen atoms to which they are bound, combine to form an optionally substituted 5-membered heterocycloalkyl group;
$R_3$ is H, $R_C$, or $R_D$;

$R_4$, $R_5$, $R_6$, and $R_7$ are each independently H, OH, $OR_C$, $OR_D$, $R_C$, or $R_D$;

$R_8$ is OH, $NH_2$, $OR_C$, $OR_D$, $NHR_C$, or $NR_CR_D$;

$R_9$ is H, OH, $OR_C$, or $OR_D$;

X is —S—, —S(O)—, or —$SO_2$—;

$R_C$ is -L-Z;

$R_D$ is optionally substituted $C_1$-$C_6$ alkyl, optionally substituted $C_1$-$C_6$ heteroalkyl, optionally substituted $C_2$-$C_6$ alkenyl, optionally substituted $C_2$-$C_6$ heteroalkenyl, optionally substituted $C_2$-$C_6$ alkynyl, optionally substituted $C_2$-$C_6$ heteroalkynyl, optionally substituted cycloalkyl, optionally substituted heterocycloalkyl, optionally substituted aryl, or optionally substituted heteroaryl;

L is optionally substituted $C_1$-$C_6$ alkylene, optionally substituted $C_1$-$C_6$ heteroalkylene, optionally substituted $C_2$-$C_6$ alkenylene, optionally substituted $C_2$-$C_6$ heteroalkenylene, optionally substituted $C_2$-$C_6$ alkynylene, optionally substituted $C_2$-$C_6$ heteroalkynylene, optionally substituted cycloalkylene, optionally substituted heterocycloalkylene, optionally substituted arylene, or optionally substituted heteroarylene; and Z is a chemical moiety formed from a coupling reaction between a reactive substituent present on L and a reactive substituent present within the antibody or antigen-binding fragment thereof, wherein Am comprises exactly one $R_C$ substituent. In other embodiments, the RNA polymerase inhibitor is an amanitin. In yet other embodiments, the amanitin is α-amanitin, β-amanitin, γ-amanitin, ε-amanitin, amanin, amaninamide, amanullin, amanullinic acid, or proamanullin.

In one embodiment, featured is an antibody drug conjugate (ADC) comprising an anti-CD137 antibody conjugated to a cytotoxin via a linker. The cytotoxin can be, for example, an amanitin, e.g., α-amanitin, β-amanitin, γ-amanitin, ε-amanitin, amanin, amaninamide, amanullin, amanullinic acid, and proamanullin. In one embodiment, the cytotoxin is α-amanitin. In one embodiment, the cytotoxin is β-amanitin. In one embodiment, the cytotoxin is γ-amanitin. In one embodiment, the cytotoxin is ε-amanitin. In one embodiment, the cytotoxin is amanin. In one embodiment, the cytotoxin is amaninamide. In one embodiment, the cytotoxin is amanullin. In one embodiment, the cytotoxin is amanullinic acid. In one embodiment, the cytotoxin is proamanullin. In one embodiment, the anti-CD137 antibody binds to the ectodomain of human CD137. In one embodiment, the anti-CD137 antibody competes with antibody BBK2.

In some embodiments, the anti-CD137 antibody comprises the CDRs of antibody BBK2. In other embodiments, the anti-CD137 antibody comprises the heavy and light chain variable regions of antibody BBK2. In yet other embodiments, the anti-CD137 antibody is chimeric BBK2. In other embodiments, the anti-CD137 antibody comprises a heavy chain sequence comprising SEQ ID NO: 23 and a light chain sequence comprising SEQ ID NO: 24. In certain embodiments, the anti-CD137 antibody is an IgG1 or an IgG4.

In another aspect, the invention features an antibody, or an antigen binding portion thereof, that specifically binds human CD137, said antibody comprising a heavy chain comprising an amino acid sequence as set forth in SEQ ID NO: 23, and comprising a light chain comprising an amino acid sequence as set forth in SEQ ID NO: 24. In certain embodiments, the antibody, or an antigen binding portion thereof is an intact antibody.

In another aspect, the invention features antibody drug conjugate (ADC) comprising the anti-CD137 antibody, or antigen binding portion thereof, of the invention, wherein the antibody antigen binding portion thereof, is conjugated to a cytotoxin via a linker. In certain embodiments, the cytotoxin is a microtubule-binding agent or an RNA polymerase inhibitor. In other embodiments, the RNA polymerase inhibitor is an amatoxin. In yet other embodiments, the amatoxin is an amanitin. In other embodiments, the amanitin is α-amanitin, β-amanitin, γ-amanitin, ε-amanitin, amanin, amaninamide, amanullin, amanullinic acid, or proamanullin. The linker can be, for example, a dipeptide which is Val-Ala or Val-Cit. In some embodiments, the linker includes a para-aminobenzyl group (PAB). In some embodiments, the linker includes the moiety PAB-Cit-Val. In some embodiments, the linker includes the moiety PAB-Ala-Val. In some embodiments, the linker includes a —((C=O)($CH_2$)$_n$— unit, wherein n is an integer from 1-6. In some embodiments, the linker is -PAB-Cit-Val-((C=O)($CH_2$)$_n$—. In some embodiments, the linker is -PAB-Ala-Val-((C=O)($CH_2$)$_n$—.

In another aspect, the invention features a pharmaceutical composition comprising an ADC of the invention, and a pharmaceutically active carrier.

In another aspect, the invention features a method of treating graft failure or GVHD in a human patient in need thereof, said method comprising administering an effective amount of an ADC of the invention to the human patient, wherein the human patient previously received a transplant. In certain embodiments, the human patient received the transplant no more than 4 days prior to the administration of the ADC.

In another aspect, the invention features a method of treating a human patient at risk for graft failure or GVHD, whereby an effective amount of an ADC described herein is administered to the human patient at risk of having graft failure or GVHD, followed by administration of a transplant to the human patient. In some embodiments, the ADC is administered to the human patient as a single dose.

In another aspect, the invention features an ADC comprising an anti-CD137 antibody conjugated to a cytotoxin via a linker, where the antibody comprises a heavy chain variable region comprising a CDR1, a CDR2, and a CDR3 having an amino acid sequence as set forth in SEQ ID NOs: 25, 26, and 27, respectively, and comprising a light chain variable region comprising a CDR1, a CDR2, and a CDR3 having an amino acid sequence as set forth in SEQ ID NOs: 29, 30, and 31, respectively. In some embodiments, the antibody is a chimeric or a humanized antibody. In certain embodiments, the heavy chain variable region comprises an amino acid sequence as set forth in SEQ ID NO: 28 and the light chain variable region comprises an amino acid sequence as set forth in SEQ ID NO: 32. In other embodiments, the antibody is an IgG1 or an IgG4 isotype. In other embodiments, the cytotoxin is a microtubule-binding agent or an RNA polymerase inhibitor. In yet other embodiments, the RNA polymerase inhibitor is an amatoxin. In yet other embodiments, the amatoxin is an amanitin. In other embodiments, the amanitin is selected from the group consisting of α-amanitin, β-amanitin, γ-amanitin, ε-amanitin, amanin, amaninamide, amanullin, amanullinic acid, and proamanullin.

In another aspect, the invention features an antibody drug conjugate (ADC) comprising an anti-CD137 antibody conjugated to a cytotoxin via a linker, wherein the antibody comprises a heavy chain variable region comprising a CDR1, a CDR2, and a CDR3 having an amino acid sequence as set forth in SEQ ID NOs: 33, 34, and 35, respectively, and comprising a light chain variable region comprising a CDR1, a CDR2, and a CDR3 having an amino acid sequence as set forth in SEQ ID NOs: 36, 37, 28, respectively. In some embodiments, the antibody is a chimeric or a humanized antibody. In other embodiments, the antibody is an IgG1 or an IgG4 isotype. In other embodiments, the cytotoxin is a microtubule-binding agent or an RNA polymerase inhibitor. In yet other embodiments, the RNA polymerase inhibitor is an amatoxin. In yet other embodiments, the amatoxin is an amanitin. In other embodiments, the amanitin is α-amanitin, β-amanitin, γ-amanitin, ε-amanitin, amanin, amaninamide, amanullin, amanullinic acid, or proamanullin.

In another aspect, the invention features a composition comprising any of the ADCs described herein, and a pharmaceutically acceptable carrier.

In another aspect, the invention features a method of treating graft failure or GVHD in a human patient in need thereof, by administering an effective amount of an ADC as described herein to the human patient, wherein the human patient previously received a transplant. In some embodiments, the human patient received the transplant no more than 4 days prior to the administration of the ADC. In some embodiments, the ADC is administered to the human patient as a single dose.

In another aspect, the invention features a method of treating human patient at risk of having graft failure or GVHD, by administering an effective amount of an anti-CD137 ADC described herein to the human patient at risk of having graft failure or GVHD, and subsequently administering a transplant to the human subject. In some embodiments, the ADC is administered to the human patient as a single dose.

DEFINITIONS

Figure 1A:
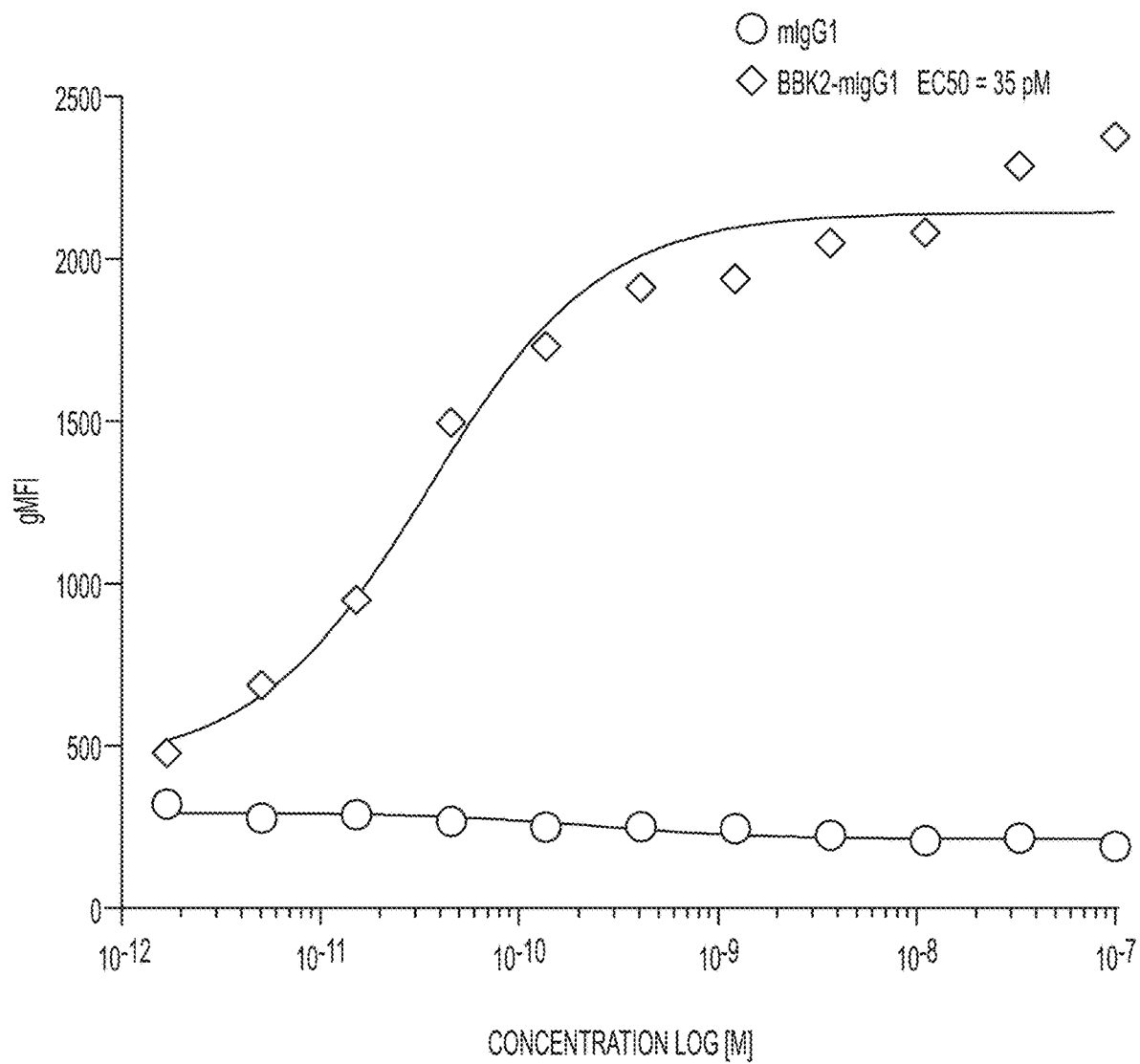
FIGS. 1A and 1B graphically depict results of an in vitro cell binding assay including a murine BBK2 (i.e., "BBK-mIgG1") and a negative control (i.e., "mIgG1") with Jurkat cells (i.e., a human T lymphocyte cell line) that over-express CD137.

As used herein, the term "about" refers to a value that is within 10% above or below the value being described. For example, the term "about 5 nM" indicates a range of from 4.5 nM to 5.5 nM.

As used herein, the term "allogeneic" refers to cells or tissues from individuals belonging to the same species but genetically different, and are therefore immunologically incompatible. Thus, the term "allogeneic cells" refers to cell types that are genetically distinct, yet belonging to the same species. Typically, the term "allogeneic" is used to define cells, such as stem cells, that are transplanted from a donor to a recipient of the same species.

As used herein, the term "amatoxin" refers to a member of the amatoxin family of peptides produced by *Amanita phalloides* mushrooms, or a variant or derivative thereof, such as a variant or derivative thereof capable of inhibiting RNA polymerase II activity. Amatoxins useful in conjunction with the compositions and methods described herein include α-amanitin, 3-amanitin, γ-amanitin, ε-amanitin, amanin, amaninamide, amanullin, amanullinic acid, and proamanullin, as well as derivatives thereof, such as a derivative described by any of formulas (IV), (IVA), and (V) described herein.

The term "antagonist" as used herein describes any molecule that inhibits or reduces the biological activity of a target molecule, e.g., CD137.

As used herein, the term "antibody" refers to an immunoglobulin molecule that specifically binds to, or is immunologically reactive with, a particular antigen, and includes polyclonal, monoclonal, genetically engineered, and otherwise modified forms of antibodies, including but not limited to chimeric antibodies, humanized antibodies, heteroconjugate antibodies (e.g., bi-, tri-, and tetra-specific antibodies, diabodies, triabodies, and tetrabodies), and antigen binding fragments of antibodies, including, for example, Fab', F(ab')$_2$, Fab, Fv, rIgG, and scFv fragments. Unless otherwise indicated, the term "monoclonal antibody" (mAb) is meant to include both intact molecules, as well as antibody fragments (including, for example, Fab and F(ab')$_2$ fragments) that are capable of specifically binding to a target protein. As used herein, the Fab and F(ab')$_2$ fragments refer to antibody fragments that lack the Fc fragment of an intact antibody. Examples of these antibody fragments are described herein.

Depending on the amino acid sequences of the constant domains of the heavy chains of antibodies, antibodies can be assigned to different classes. There are five major classes of immunoglobulins: IgA, IgD, IgE, IgG and IgM, and several of these may be further divided into subclasses (isotypes), e.g., IgG1, IgG2, IgG3, IgG4, IgA1, and IgA2. The heavy chain constant domains that correspond to the different classes of immunoglobulins are called alpha, delta, epsilon, gamma, and mu, respectively. The subunit structures and three-dimensional configurations of different classes of immunoglobulins are well known and described generally in, for example, Abbas et al. Cellular and Mol. Immunology, 4th ed. (2000). An antibody may be part of a larger fusion molecule, formed by covalent or non-covalent association of the antibody with one or more other proteins or peptides.

The term "antigen-binding fragment," as used herein, refers to one or more fragments of an antibody that retain the ability to specifically bind to a target antigen. The antigen-binding function of an antibody can be performed by fragments of a full-length antibody. The antibody fragments can be, for example, a Fab, F(ab')$_2$, scFv, diabody, a triabody, an affibody, a nanobody, an aptamer, or a domain antibody. Examples of binding fragments encompassed of the term "antigen-binding fragment" of an antibody include, but are not limited to: (i) a Fab fragment, a monovalent fragment consisting of the $V_L$, $V_H$, $C_L$, and $C_{H1}$ domains; (ii) a F(ab')$_2$ fragment, a bivalent fragment comprising two Fab fragments linked by a disulfide bridge at the hinge region; (iii) a Fd fragment consisting of the $V_H$ and $C_{H1}$ domains; (iv) a Fv fragment consisting of the $V_L$ and $V_H$ domains of a single arm of an antibody, (v) a dAb including $V_H$ and $V_L$ domains; (vi) a dAb fragment that consists of a $V_H$ domain (see, e.g., Ward et al., Nature 341:544-546, 1989); (vii) a dAb which consists of a $V_H$ or a $V_L$ domain; (viii) an isolated complementarity determining region (CDR); and (ix) a combination of two or more (e.g., two, three, four, five, or six) isolated CDRs which may optionally be joined by a synthetic linker. Furthermore, although the two domains of the Fv fragment, $V_L$ and $V_H$, are coded for by separate genes, they can be joined, using recombinant methods, by a linker that enables them to be made as a single protein chain in which the $V_L$ and $V_H$ regions pair to form monovalent molecules (known as single chain Fv (scFv). These antibody fragments can be obtained using conventional techniques known to those of skill in the art, and the fragments can be screened for utility in the same manner as intact antibodies. Antigen-binding fragments can be produced by recombinant DNA techniques, enzymatic or chemical cleavage of intact immunoglobulins, or, in certain cases, by chemical peptide synthesis procedures known in the art.

As used herein, the term "anti-CD137 antibody" refers to a protein or peptide-containing molecule that includes at least a portion of an immunoglobulin molecule, such as but not limited to at least one CDR of a heavy or light chain or a ligand binding portion thereof, a heavy chain or light chain variable region, a heavy chain or light chain constant region, a framework region, or any portion thereof, that is capable of specifically binding to CD137. Anti-CD137 antibodies also include antibody-like protein scaffolds, such as the tenth fibronectin type III domain ($^{10}$Fn3), which contains BC, DE, and FG structural loops similar in structure and solvent accessibility to antibody CDRs. The tertiary structure of the $^{10}$Fn3 domain resembles that of the variable region of the IgG heavy chain, and one of skill in the art can graft, for example, the CDRs of an anti-CD137 monoclonal antibody onto the fibronectin scaffold by replacing residues of the BC, DE, and FG loops of $^{10}$Fn3 with residues from the CDRH-1, CDRH-2, or CDRH-3 regions of an anti-CD137 monoclonal antibody. In one embodiment, an anti-CD137 antibody specifically binds to human CD137.

As used herein, the term "bispecific antibody" refers to, for example, a monoclonal, often a human or humanized antibody that is capable of binding at least two different antigens. For instance, one of the binding specificities can be directed towards a T cell surface antigen, such as CD137, the other can be for a different T cell surface antigen or another cell surface protein, such as a receptor or receptor subunit involved in a signal transduction pathway that prohibits or limits cell growth, among others.

As used herein, the term "chimeric" antibody refers to refers to antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (See, for example, U.S. Pat. No. 4,816,567 and Morrison et al., 1984, Proc. Natl. Acad. Sci. USA 81:6851-6855). In one embodiment, a chimeric antibody comprises murine heavy and light chain variable regions and human light and heavy chain constant regions.

As used herein, the terms "complementarity determining region" and "CDR" refer to a hypervariable region found both in the light chain and the heavy chain variable domains of an antibody. The more highly conserved portions of variable domains are referred to as framework regions (FRs). The amino acid positions that delineate a hypervariable region of an antibody can vary, depending on the context and the various definitions known in the art. Some positions within a variable domain may be viewed as hybrid hypervariable positions in that these positions can be deemed to be within a hypervariable region under one set of criteria while being deemed to be outside a hypervariable region under a different set of criteria. One or more of these positions can also be found in extended hypervariable regions. The antibodies described herein may contain modifications in these hybrid hypervariable positions. The variable domains of native heavy and light chains each comprise four framework regions that primarily adopt a 3-sheet configuration, connected by three CDRs, which form loops that connect, and in some cases form part of, the 1-sheet structure. The CDRs in each chain are held together in close proximity by the framework regions in the order FR1-CDR1-FR2-CDR2-FR3-CDR3-FR4 and, with the CDRs from the other antibody chains, contribute to the formation of the target binding site of antibodies (e.g., see Kabat et al., Sequences of Proteins of Immunological Interest, National Institute of Health, Bethesda, Md., 1987 or http://www.imgt.org/3Dstructure-DB/cgi/DomainGapAlign.cgi). Numbering of immunoglobulin amino acid residues, including CDRs, can be performed according to the immunoglobulin amino acid residue numbering system of Kabat et al.

As used herein, the term "conjugate" refers to a compound formed by the chemical bonding of a reactive functional group of one molecule, such as an antibody or antigen-binding fragment thereof, with an appropriately reactive functional group of another molecule, such as a cytotoxin described herein. Conjugates may include a linker between the two molecules bound to one another, e.g., between an antibody and a cytotoxin. Examples of linkers that can be used for the formation of a conjugate include peptide-containing linkers, such as those that contain naturally occurring or non-naturally occurring amino acids, such as D-amino acids. Linkers can be prepared using a variety of strategies described herein and known in the art. Depending on the reactive components therein, a linker may be cleaved, for example, by enzymatic hydrolysis, photolysis, hydrolysis under acidic conditions, hydrolysis under basic conditions, oxidation, disulfide reduction, nucleophilic cleavage, or organometallic cleavage (see, for example, Leriche et al., Bioorg. Med. Chem., 20:571-582, 2012). Notably, the term "conjugate" (when referring to a compound) is also referred to interchangeably herein as a "drug antibody conjugate" or an "antibody drug conjugate (ADC)".

As used herein, the term "coupling reaction" refers to a chemical reaction in which two or more substituents suitable for reaction with one another react so as to form a chemical moiety that joins (e.g., covalently) the molecular fragments bound to each substituent. Coupling reactions include those in which a reactive substituent bound to a fragment that is a cytotoxin, such as a cytotoxin known in the art or described herein, reacts with a suitably reactive substituent bound to a fragment that is an for CD137 known in the art or described herein. Examples of suitably reactive substituents include a nucleophile/electrophile pair (e.g., a thiol/haloalkyl pair, an amine/carbonyl pair, or a thiol/α,β-unsaturated carbonyl pair, among others), a diene/dienophile pair (e.g., an azide/alkyne pair, among others), and the like. Coupling reactions include, without limitation, thiol alkylation, hydroxyl alkylation, amine alkylation, amine condensation, amidation, esterification, disulfide formation, cycloaddition (e.g., [4+2] Diels-Alder cycloaddition, [3+2] Huisgen cycloaddition, among others), nucleophilic aromatic substitution, electrophilic aromatic substitution, and other reactive modalities known in the art or described herein.

As used herein, the term "donor" refers to a human or animal from which one or more cells are isolated prior to administration of the cells, or progeny thereof, into a recipient. The one or more cells may be, for example, a population of hematopoietic stem cells.

As used herein, the term "diabody" refers to a bivalent antibody containing two polypeptide chains, in which each polypeptide chain includes $V_H$ and $V_L$ domains joined by a linker that is too short (e.g., a linker composed of five amino acids) to allow for intramolecular association of $V_H$ and $V_L$ domains on the same peptide chain. This configuration forces each domain to pair with a complementary domain on another polypeptide chain so as to form a homodimeric structure. Accordingly, the term "triabody" refers to trivalent antibodies comprising three peptide chains, each of which contains one $V_H$ domain and one $V_L$ domain joined by a linker that is exceedingly short (e.g., a linker composed of 1-2 amino acids) to permit intramolecular association of $V_H$ and $V_L$ domains within the same peptide chain. In order to fold into their native structures, peptides configured in this way typically trimerize so as to position the $V_H$ and $V_L$ domains of neighboring peptide chains spatially proximal to one another (see, for example, Holliger et al., Proc. Natl. Acad. Sci. USA 90:6444-48, 1993).

As used herein, a "dual variable domain immunoglobulin" ("DVD-Ig") refers to an antibody that combines the target-binding variable domains of two monoclonal antibodies via linkers to create a tetravalent, dual-targeting single agent (see, for example, Gu et al., Meth. Enzymol., 502:25-41, 2012).

As used herein, the term "endogenous" describes a substance, such as a molecule, cell, tissue, or organ (e.g., a hematopoietic stem cell or a cell of hematopoietic lineage, such as a megakaryocyte, thrombocyte, platelet, erythrocyte, mast cell, myoblast, basophil, neutrophil, eosinophil, microglial cell, granulocyte, monocyte, osteoclast, antigen-presenting cell, macrophage, dendritic cell, natural killer cell, T cell, or B cell) that is found naturally in a particular organism, such as a human patient.

As used herein, the term "exogenous" describes a substance, such as a molecule, cell, tissue, or organ (e.g., a hematopoietic stem cell or a cell of hematopoietic lineage, such as a megakaryocyte, thrombocyte, platelet, erythrocyte, mast cell, myoblast, basophil, neutrophil, eosinophil, microglial cell, granulocyte, monocyte, osteoclast, antigen-presenting cell, macrophage, dendritic cell, natural killer cell, T cell, or B cell) that is not found naturally in a particular organism, such as a human patient. Exogenous substances include those that are provided from an external source to an organism or to cultured matter extracted therefrom.

As used herein, the term "framework region", "FR", or "FW region" includes amino acid residues that are adjacent to the CDRs within a variable region of an antibody, or antigen-binding fragment thereof. FW region residues may be present in, for example, human antibodies, humanized antibodies, monoclonal antibodies, antibody fragments, Fab fragments, single chain antibody fragments, scFv fragments, antibody domains, and bispecific antibodies, among others.

As used herein, the term "half-life" refers to the time it takes for the plasma concentration of the antibody drug in the body to be reduced by one half or 50%. This 50% reduction in serum concentration reflects the amount of drug circulating and not removed by the natural methods of antibody clearance.

As used herein, the term "hematopoietic stem cells" ("HSCs") refers to immature blood cells having the capacity to self-renew and to differentiate into mature blood cells comprising diverse lineages including but not limited to granulocytes (e.g., promyelocytes, neutrophils, eosinophils, basophils), erythrocytes (e.g., reticulocytes, erythrocytes), thrombocytes (e.g., megakaryoblasts, platelet producing megakaryocytes, platelets), monocytes (e.g., monocytes, macrophages), dendritic cells, microglia, osteoclasts, and lymphocytes (e.g., NK cells, B cells and T cells). Such cells may include $CD34^+$ cells. $CD34^+$ cells are immature cells that express the CD34 cell surface marker. In humans, CD34+ cells are believed to include a subpopulation of cells with the stem cell properties defined above, whereas in mice, HSCs are CD34−. In addition, HSCs also refer to long term repopulating HSCs (LT-HSC) and short term repopulating HSCs (ST-HSC). LT-HSCs and ST-HSCs are differentiated, based on functional potential and on cell surface marker expression. For example, human HSCs are CD34+, CD38−, CD45RA−, CD90+, CD49F+, and lin− (negative for mature lineage markers including CD2, CD3, CD4, CD7, CD8, CD10, CD11B, CD19, CD20, CD56, CD235A). In mice, bone marrow LT-HSCs are CD34−, SCA-1+, C-kit+, CD135−, Slamfl/CD150+, CD48−, and lin− (negative for mature lineage markers including Ter119, CD11b, Gr1, CD3, CD4, CD8, B220, IL7ra), whereas ST-HSCs are CD34+, SCA-1+, C-kit+, CD135−, Slamfl/CD150+, and lin− (negative for mature lineage markers including Ter119, CD11b, Gr1, CD3, CD4, CD8, B220, IL7ra). In addition, ST-HSCs are less quiescent and more proliferative than LT-HSCs under homeostatic conditions. However, LT-HSC have greater self-renewal potential (i.e., they survive throughout adulthood, and can be serially transplanted through successive recipients), whereas ST-HSCs have limited self-renewal (i.e., they survive for only a limited period of time, and do not possess serial transplantation potential). Any of these HSCs can be used in the methods described herein. ST-HSCs are particularly useful because they are highly proliferative and thus, can more quickly give rise to differentiated progeny.

As used herein, the term "hematopoietic stem cell functional potential" refers to the functional properties of hematopoietic stem cells which include 1) multi-potency (which refers to the ability to differentiate into multiple different blood lineages including, but not limited to, granulocytes (e.g., promyelocytes, neutrophils, eosinophils, basophils), erythrocytes (e.g., reticulocytes, erythrocytes), thrombocytes (e.g., megakaryoblasts, platelet producing megakaryocytes, platelets), monocytes (e.g., monocytes, macrophages), dendritic cells, microglia, osteoclasts, and lymphocytes (e.g., NK cells, T cells and B cells), 2) self-renewal (which refers to the ability of hematopoietic stem cells to give rise to daughter cells that have equivalent potential as the mother cell, and further that this ability can repeatedly occur throughout the lifetime of an individual without exhaustion), and 3) the ability of hematopoietic stem cells or progeny thereof to be reintroduced into a transplant recipient whereupon they home to the hematopoietic stem cell niche and re-establish productive and sustained hematopoiesis.

As used herein, the term "human antibody" refers to an antibody in which substantially every part of the protein (for example, all CDRs, framework regions, $C_L$, $C_H$ domains (e.g., $C_H1$, $C_{H2}$, $C_{H3}$), hinge, and $V_L$ and $V_H$ domains) is substantially non-immunogenic in humans, with only minor sequence changes or variations. A human antibody can be produced in a human cell (for example, by recombinant expression) or by a non-human animal or a prokaryotic or eukaryotic cell that is capable of expressing functionally rearranged human immunoglobulin (such as heavy chain and/or light chain) genes. When a human antibody is a single chain antibody, it can include a linker peptide that is not found in native human antibodies. For example, an Fv can contain a linker peptide, such as two to about eight glycine or other amino acid residues, which connects the variable region of the heavy chain and the variable region of the light chain. Such linker peptides are considered to be of human origin. Human antibodies can be made by a variety of methods known in the art including phage display methods using antibody libraries derived from human immunoglobulin sequences. Human antibodies can also be produced using transgenic mice that are incapable of expressing functional endogenous immunoglobulins, but which can express human immunoglobulin genes.

A "humanized" antibody refers to a non-human antibody that contains minimal sequences derived from non-human immunoglobulin. Thus, "humanized" forms of non-human (e.g., murine) antibodies are chimeric antibodies that contain minimal sequence derived from the non-human antibody. In general, a humanized antibody contains substantially all of at least one, and typically two, variable domains, in which all or substantially all of the CDR regions correspond to those of a non-human immunoglobulin. All or substantially all of the FW regions may also be those of a human immunoglobulin sequence. The humanized antibody can also comprise at least a portion of an immunoglobulin constant region (Fc), typically that of a human immunoglobulin consensus sequence. Methods of antibody humanization are known in the art.

In one embodiment, a humanized antibody is a human antibody (recipient antibody) in which residues from CDRs of the recipient are replaced by residues from CDRs of a non-human species (donor antibody) such as mouse, rat, rabbit, or nonhuman primate having the desired specificity, affinity, and/or capacity. In some instances, framework region (FR) residues of the human antibody are replaced by corresponding non-human residues. Furthermore, humanized antibodies may comprise residues that are not found in the recipient antibody or in the donor antibody. These modifications may be made to further refine antibody performance. In general, a humanized antibody will comprise substantially all of at least one, and typically two, variable domains, in which all or substantially all of the hypervariable loops correspond to those of a non-human antibody, and all or substantially all of the FRs are those of a human immunoglobulin sequence. The humanized antibody optionally will also comprise at least a portion of an antibody constant region (Fc), typically that of a human immunoglobulin. For further details, see Jones et al., Nature 321: 522-525 (1986); Riechmann et al., Nature 332:323-329 (1988); and Presta, Curr. Op. Struct. Biol. 2:593-596 (1992). See also the following review articles and references cited therein: Vaswani and Hamilton, Ann. Allergy, Asthma & Immunol. 1:105-115 (1998); Harris, Biochem. Soc. Transactions 23:1035-1038 (1995); Hurle and Gross, Curr. Op. Biotech. 5:428-433 (1994).

The terms "full length antibody" and "intact antibody" are used herein interchangeably to refer to an antibody in its substantially intact form, and not an antibody fragment as defined herein. Thus, for an IgG antibody, an intact antibody comprises two heavy chains each comprising a variable region, a constant region and an Fc region, and two light chains each comprising a variable region and a constant region. More specifically, an intact IgG comprises two light chains each comprising a light chain variable region (VL) and a light chain constant region (CL), and comprises two heavy chains each comprising a heavy chain variable region (VH) and three heavy chain constant regions (CH1, CH2, and CH3). CH2 and CH3 represent the Fc region of the heavy chain.

As used herein, the term "microtubule-binding agent" refers to a compound which acts by disrupting the microtubular network that is essential for mitotic and interphase cellular function. Examples of a microtubule-binding agent include, but are not limited to, maytasine, maytansinoids, and derivatives thereof, such as those described herein or known in the art, vinca alkaloids, such as vinblastine, vinblastine sulfate, vincristine, vincristine sulfate, vindesine, and vinorelbine, taxanes, such as docetaxel and paclitaxel, macrolides, such as discodermolides, cochicine, and epothilones, and derivatives thereof, such as epothilone B or a derivative thereof. Paclitaxel is marketed as TAXOL®; docetaxel as TAXOTERE®; vinblastine sulfate as VINBLASTIN R.P®; and vincristine sulfate as FARMISTIN®. Also included are the generic forms of paclitaxel as well as various dosage forms of paclitaxel. Generic forms of paclitaxel include, but are not limited to, betaxolol hydrochloride. Various dosage forms of paclitaxel include, but are not limited to albumin nanoparticle paclitaxel marketed as ABRAXANE®; ONXOL®, CYTOTAX®. Discodermolide can be obtained, e.g., as disclosed in U.S. Pat. No. 5,010, 099. Also included are epotholine derivatives which are disclosed in U.S. Pat. No. 6,194,181, WO9810121, WO9825929, WO9808849, WO9943653, WO9822461 and WO0031247, the disclosures of each of which are incorporated herein by reference.

As used herein, the term "monoclonal antibody" refers to an antibody that is derived from a single clone, including any eukaryotic, prokaryotic, or phage clone, and not the method by which it is produced.

As used herein, the term "patient at risk for GVHD" refers to a patient with one or more risk factors for developing GVHD. Risk factors include, but are not limited to, allogeneic donor transplant (e.g., transplantation of hematopoietic stem cells from a bone marrow transplant), including mismatched human leucocyte antigen (HLA) donor and sex mismatched donor, T cell replete stem cell transplant, donor and recipient age, presence of cytomegalovirus (CMV) or CMV antibodies in transplant donor or host, increased dose of total-body irradiation (TBI), conditioning regimen intensity, acute GVHD prophylaxis, lack of protective environments, splenectomy, immunoglobulin use, underlying disease, ABO compatibility, prior exposure to herpes viruses, donor blood transfusions, performance score, antibiotic gut decontamination, and post-allogeneic transplant blood transfusions.

As used herein, the term "patient at risk for an autoimmune disease" refers to a patient with one or more risk factors for developing an autoimmune disease. Risk factors include, but are not limited to, age (young to middle aged), sex (female), ethnicity (African American, American Indian, or Latino), family history of autoimmune diseases, exposure to environmental agents, previous infection, chronic inflammation, and donor transplantation (e.g., transplantation of hematopoietic stem cells from a bone marrow transplant). As used herein, the term "recipient" refers to a patient that receives a transplant, such as a transplant containing a population of hematopoietic stem cells. The transplanted cells administered to a recipient may be, e.g., autologous, syngeneic, or allogeneic cells.

As used herein, the term "sample" refers to a specimen (e.g., blood, blood component (e.g., serum or plasma), urine, saliva, amniotic fluid, cerebrospinal fluid, tissue (e.g., placental or dermal), pancreatic fluid, chorionic villus sample, and cells) taken from a subject.

As used herein, the term "scFv" refers to a single chain Fv antibody in which the variable domains of the heavy chain and the light chain from an antibody have been joined to form one chain. scFv fragments contain a single polypeptide chain that includes the variable region of an antibody light chain ($V_L$) (e.g., CDR-L1, CDR-L2, and/or CDR-L3) and the variable region of an antibody heavy chain ($V_H$) (e.g., CDR-H1, CDR-H2, and/or CDR-H3) separated by a linker. The linker that joins the $V_L$ and $V_H$ regions of a scFv fragment can be a peptide linker composed of proteinogenic amino acids. Alternative linkers can be used to so as to increase the resistance of the scFv fragment to proteolytic degradation (for example, linkers containing D-amino acids), in order to enhance the solubility of the scFv fragment (for example, hydrophilic linkers such as polyethylene glycol-containing linkers or polypeptides containing repeating glycine and serine residues), to improve the biophysical stability of the molecule (for example, a linker containing cysteine residues that form intramolecular or intermolecular disulfide bonds), or to attenuate the immunogenicity of the scFv fragment (for example, linkers containing glycosylation sites). It will also be understood by one of ordinary skill in the art that the variable regions of the scFv molecules described herein can be modified such that they vary in amino acid sequence from the antibody molecule from which they were derived. For example, nucleotide or amino acid substitutions leading to conservative substitutions or changes at amino acid residues can be made (e.g., in CDR and/or framework residues) so as to preserve or enhance the ability of the scFv to bind to the antigen recognized by the corresponding antibody.

The terms "specific binding" or "specifically binding", as used herein, refers to the ability of an antibody (or an ADC) to recognize and bind to a specific protein structure (epitope) rather than to proteins generally. If an antibody or ADC is specific for epitope "A", the presence of a molecule containing epitope A (or free, unlabeled A), in a reaction containing labeled "A" and the antibody, will reduce the amount of labeled A bound to the antibody or ADC. By way of example, an antibody "binds specifically" to a target if the antibody, when labeled, can be competed away from its target by the corresponding non-labeled antibody. In one embodiment, an antibody specifically binds to a target, e.g., CD137, if the antibody has a $K_D$ for the target of at least about $10^{-4}$ M, $10^{-5}$ M, $10^{-6}$ M, $10^{-7}$ M, $10^{-8}$ M, $10^{-9}$ M, $10^{-10}$ M, $10^{-11}$ M, $10^{-12}$ M, or less (less meaning a number that is less than $10^{-12}$, e.g. $10^{-13}$). In one embodiment, the term "specific binding to CD137" or "specifically binds to CD137," as used herein, refers to an antibody or an ADC that binds to CD137 and has a dissociation constant ($K_D$) of $1.0 \times 10^{0.7}$ M or less, as determined by surface plasmon resonance. In one embodiment, $K_D$ is determined according to standard bio-layer interferometery (BLI). It shall be understood, however, that the antibody or ADC may be capable of specifically binding to two or more antigens which are related in sequence. For example, in one embodiment, an antibody can specifically bind to both human and a non-human (e.g., mouse or non-human primate) orthologs of CD137.

As used herein, the terms "subject" and "patient" refer to an organism, such as a human, that receives treatment for a particular disease or condition as described herein. For instance, a patient, such as a human patient, may receive treatment prior to hematopoietic stem cell transplant therapy in order to treat or prevent GVHD by administration of an antibody, antigen-binding fragment thereof, or ligand as described herein capable of binding CD137.

As used herein, the phrase "substantially cleared from the blood" refers to a point in time following administration of a therapeutic agent (such as an anti-CD137 antibody, antigen-binding fragment thereof, ADC, or soluble ligand) to a patient when the concentration of the therapeutic agent in a blood sample isolated from the patient is such that the therapeutic agent is not detectable by conventional means (for instance, such that the therapeutic agent is not detectable above the noise threshold of the device or assay used to detect the therapeutic agent). A variety of techniques known in the art can be used to detect antibodies, antibody fragments and protein ligands, such as ELISA-based detection assays known in the art or described herein. Additional assays that can be used to detect antibodies, antibody fragments, and protein ligands include immunoprecipitation techniques and immunoblot assays, among others known in the art.

As used herein, the phrase "stem cell disorder" broadly refers to any disease, disorder, or condition that may be treated or cured by conditioning a subject's target tissues, and/or by ablating an endogenous stem cell population in a target tissue (e.g., ablating an endogenous hematopoietic stem or progenitor cell population from a subject's bone marrow tissue) and/or by engrafting or transplanting stem cells in a subject's target tissues. For example, Type I diabetes has been shown to be cured by hematopoietic stem cell transplant and may benefit from conditioning in accordance with the compositions and methods described herein. Additional disorders that can be treated using the compositions and methods described herein include, without limitation, sickle cell anemia, thalassemias, Fanconi anemia, Wiskott-Aldrich syndrome, ADA SCID, HIV/AIDS, metachromatic leukodystrophy, Diamond-Blackfan anemia, and Schwachman-Diamond syndrome. The subject may have or be affected by an inherited blood disorder (e.g., sickle cell anemia) or an autoimmune disorder. Additionally or alternatively, the subject may have or be affected by a malignancy, such as a malignancy selected from the group consisting of hematologic cancers (e.g., leukemia, lymphoma, multiple myeloma, or myelodysplastic syndrome) and neuroblastoma. In some embodiments, the subject has or is otherwise affected by a metabolic disorder. For example, the subject may suffer or otherwise be affected by a metabolic disorder selected from the group consisting of glycogen storage diseases, mucopolysaccharidoses, Gaucher's Disease, Hurlers Disease, sphingolipidoses, metachromatic leukodystrophy, or any other diseases or disorders which may benefit from the treatments and therapies disclosed herein and including, without limitation, severe combined immunodeficiency, Wiscott-Aldrich syndrome, hyper immunoglobulin M (IgM) syndrome, Chediak-Higashi disease, hereditary lymphohistiocytosis, osteopetrosis, osteogenesis imperfecta, storage diseases, thalassemia major, sickle cell disease, systemic sclerosis, systemic lupus erythematosus, multiple sclerosis, juvenile rheumatoid arthritis and those diseases, or disorders described in "Bone Marrow Transplantation for Non-Malignant Disease," ASH Education Book, 1:319-338 (2000), the disclosure of which is incorporated herein by reference in its entirety as it pertains to pathologies that may be treated by administration of hematopoietic stem cell transplant therapy.

As used herein, the term "suffering from disease" refers to a subject (e.g., a human) that is experiencing GVHD or an autoimmune disease. It is not intended that the present invention be limited to any particular signs or symptoms, nor disease. Thus, it is intended that the present invention encompass subjects that are experiencing any range of disease, from sub-clinical to full-blown disease, wherein the subject exhibits at least some of the indicia (e.g., signs and symptoms) associated with GVHD or an autoimmune disease.

As used herein, the term "transfection" refers to any of a wide variety of techniques commonly used for the introduction of exogenous DNA into a prokaryotic or eukaryotic host cell, such as electroporation, lipofection, calcium-phosphate precipitation, DEAE-dextran transfection and the like.

As used herein, the term "transplant" refers to any organ, body tissue, or cell(s) that has been transferred from its site of origin to a recipient site, or the act of doing so.

As used herein, the terms "treat" or "treatment" refer to therapeutic treatment, in which the object is to prevent or slow down (lessen) an undesired physiological change or disorder or to promote a beneficial phenotype in the patient being treated. Beneficial or desired clinical results include, but are not limited to, a decrease in the cell count or relative concentration of CD137 positive cells, a decrease in the cellular and clinical manifestations of GVHD or an autoimmune disease, promoting the engraftment of exogenous hematopoietic cells in a patient as described herein and subsequent hematopoietic stem cell transplant therapy. Additional beneficial results include an increase in the cell count or relative concentration of hematopoietic stem cells suffering from or at risk for GVHD. Beneficial results of therapy described herein may also include an increase in the cell count or relative concentration of one or more cells of hematopoietic lineage, such as a megakaryocyte, thrombocyte, platelet, erythrocyte, mast cell, myeoblast, basophil, neutrophil, eosinophil, microglial cell, granulocyte, monocyte, osteoclast, antigen-presenting cell, macrophage, dendritic cell, natural killer cell, T cell, or B cell, following hematopoietic stem cell transplant therapy.

As used herein, the term "effective amount" or "therapeutically effective amount" refers to an amount that is sufficient to achieve the desired result or to have an effect on GVHD or an autoimmune disease. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the art.

Dosage can vary, and can be administered in one or more dose administrations daily, for one or several days.

The "variable region" or "variable domain" of an antibody refers to the amino-terminal domains of a heavy or light chain of the antibody. The variable domain of the heavy chain may be referred to as "VH." The variable domain of the light chain may be referred to as "VL." These domains are generally the most variable parts of an antibody and contain the antigen-binding sites (CDRs).

As used herein, the term "vector" includes a nucleic acid vector, such as a plasmid, a DNA vector, a plasmid, a RNA vector, virus, or other suitable replicon. Expression vectors described herein may contain a polynucleotide sequence as well as, for example, additional sequence elements used for the expression of proteins and/or the integration of these polynucleotide sequences into the genome of a mammalian cell. Certain vectors that can be used for the expression of antibodies and antibody fragments of the invention include plasmids that contain regulatory sequences, such as promoter and enhancer regions, which direct gene transcription. Other useful vectors for expression of antibodies and antibody fragments contain polynucleotide sequences that enhance the rate of translation of these genes or improve the stability or nuclear export of the mRNA that results from gene transcription. These sequence elements may include, for example, 5' and 3' untranslated regions and a polyadenylation signal site in order to direct efficient transcription of the gene carried on the expression vector. The expression vectors described herein may also contain a polynucleotide encoding a marker for selection of cells that contain such a vector. Examples of a suitable marker include genes that encode resistance to antibiotics, such as ampicillin, chloramphenicol, kanamycin, and nourseothricin.

As used herein, the term "alkyl" refers to a straight- or branched-chain alkyl group having, for example, from 1 to 20 carbon atoms in the chain. Examples of alkyl groups include methyl, ethyl, n-propyl, isopropyl, butyl, isobutyl, sec-butyl, tert-butyl, pentyl, isopentyl, tert-pentyl, hexyl, isohexyl, and the like.

As used herein, the term "alkylene" refers to a straight- or branched-chain divalent alkyl group. The divalent positions may be on the same or different atoms within the alkyl chain. Examples of alkylene include methylene, ethylene, propylene, isopropylene, and the like.

As used herein, the term "heteroalkyl" refers to a straight or branched-chain alkyl group having, for example, from 1 to 20 carbon atoms in the chain, and further containing one or more heteroatoms (e.g., oxygen, nitrogen, or sulfur, among others) in the chain.

As used herein, the term "heteroalkylene" refers to a straight- or branched-chain divalent heteroalkyl group. The divalent positions may be on the same or different atoms within the heteroalkyl chain.

As used herein, the term "alkenyl" refers to a straight- or branched-chain alkenyl group having, for example, from 2 to 20 carbon atoms in the chain. Examples of alkenyl groups include vinyl, propenyl, isopropenyl, butenyl, tert-butylenyl, hexenyl, and the like.

As used herein, the term "alkenylene" refers to a straight- or branched-chain divalent alkenyl group. The divalent positions may be on the same or different atoms within the alkenyl chain. Examples of alkenylene include ethenylene, propenylene, isopropenylene, butenylene, and the like.

As used herein, the term "heteroalkenyl" refers to a straight- or branched-chain alkenyl group having, for example, from 2 to 20 carbon atoms in the chain, and further containing one or more heteroatoms (e.g., oxygen, nitrogen, or sulfur, among others) in the chain.

As used herein, the term "heteroalkenylene" refers to a straight- or branched-chain divalent heteroalkenyl group. The divalent positions may be on the same or different atoms within the heteroalkenyl chain.

As used herein, the term "alkynyl" refers to a straight- or branched-chain alkynyl group having, for example, from 2 to 20 carbon atoms in the chain. Examples of alkynyl groups include propargyl, butynyl, pentynyl, hexynyl, and the like.

As used herein, the term "alkynylene" refers to a straight- or branched-chain divalent alkynyl group. The divalent positions may be on the same or different atoms within the alkynyl chain.

As used herein, the term "heteroalkynyl" refers to a straight- or branched-chain alkynyl group having, for example, from 2 to 20 carbon atoms in the chain, and further containing one or more heteroatoms (e.g., oxygen, nitrogen, or sulfur, among others) in the chain.

As used herein, the term "heteroalkynylene" refers to a straight- or branched-chain divalent heteroalkynyl group. The divalent positions may be on the same or different atoms within the heteroalkynyl chain.

As used herein, the term "cycloalkyl" refers to a monocyclic, or fused, bridged, or spiro polycyclic ring structure that is saturated and has, for example, from 3 to 12 carbon ring atoms. Examples of cycloalkyl groups include cyclopropyl, cyclobutyl, cyclopentyl, cyclohexyl, cycloheptyl, cyclooctyl, bicyclo[3.1.0]hexane, and the like.

As used herein, the term "cycloalkylene" refers to a divalent cycloalkyl group. The divalent positions may be on the same or different atoms within the ring structure. Examples of cycloalkylene include cyclopropylene, cyclobutylene, cyclopentylene, cyclohexylene, and the like.

As used herein, the term "heterocyloalkyl" refers to a monocyclic, or fused, bridged, or spiro polycyclic ring structure that is saturated and has, for example, from 3 to 12 ring atoms per ring structure selected from carbon atoms and heteroatoms selected from, e.g., nitrogen, oxygen, and sulfur, among others. The ring structure may contain, for example, one or more oxo groups on carbon, nitrogen, or sulfur ring members.

As used herein, the term "heterocycloalkylene" refers to a divalent heterocyclolalkyl group. The divalent positions may be on the same or different atoms within the ring structure. As used herein, the term "aryl" refers to a monocyclic or multicyclic aromatic ring system containing, for example, from 6 to 19 carbon atoms. Aryl groups include, but are not limited to, phenyl, fluorenyl, naphthyl, and the like.

As used herein, the term "arylene" refers to a divalent aryl group. The divalent positions may be on the same or different atoms.

As used herein, the term "heteroaryl" refers to a monocyclic heteroaromatic, or a bicyclic or a tricyclic fused-ring heteroaromatic group. Heteroaryl groups include pyridyl, pyrrolyl, furyl, thienyl, imidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadia-zolyl, 1,2,5-oxadiazolyl, 1,3,4-oxadiazolyl, 1,3,4-triazinyl, 1,2,3-triazinyl, benzofuryl, [2,3-dihydro]benzofuryl, isobenzofuryl, benzothienyl, benzotriazolyl, isobenzothienyl, indolyl, isoindolyl, 3H-indolyl, benzimidazolyl, imidazo[1,2-a]pyridyl, benzothiazolyl, benzoxazolyl, quinolizinyl, quinazolinyl, pthalazinyl, quinoxalinyl, cinnolinyl, napthyridinyl, pyrido[3,4-b]pyridyl, pyrido[3,2-b]pyridyl, pyrido[4,3-b]pyridyl, quinolyl, isoquinolyl, tetrazolyl, 5,6,7,8-tetrahydroquinolyl, 5,6,7,8-tetrahydroisoquinolyl, purinyl, pteridinyl, carbazolyl, xanthenyl, benzoquinolyl, and the like.

As used herein, the term "heteroarylene" refers to a divalent heteroaryl group. The divalent positions may be on the same or different atoms.

Unless otherwise constrained by the definition of the individual substituent, the foregoing chemical moieties, such as "alkyl", "alkylene", "heteroalkyl", "heteroalkylene", "alkenyl", "alkenylene", "heteroalkenyl", "heteroalkenylene", "alkynyl", "alkynylene", "heteroalkynyl", "heteroalkynylene", "cycloalkyl", "cycloalkylene", "heterocyclolalkyl", heterocycloalkylene", "aryl," "arylene", "heteroaryl", and "heteroarylene" groups can optionally be substituted with, for example, from 1 to 5 substituents selected from the group consisting of alkyl, alkenyl, alkynyl, cycloalkyl, heterocycloalkyl, alkyl aryl, alkyl heteroaryl, alkyl cycloalkyl, alkyl heterocycloalkyl, amino, ammonium, acyl, acyloxy, acylamino, aminocarbonyl, alkoxycarbonyl, ureido, carbamate, aryl, heteroaryl, sulfinyl, sulfonyl, alkoxy, sulfanyl, halogen, carboxy, trihalomethyl, cyano, hydroxy, mercapto, nitro, and the like. The substitution may include situations in which neighboring substituents have undergone ring closure, such as ring closure of vicinal functional substituents, to form, for instance, lactams, lactones, cyclic anhydrides, acetals, hemiacetals, thioacetals, aminals, and hemiaminals, formed by ring closure, for example, to furnish a protecting group.

DETAILED DESCRIPTION

The invention provides methods of preventing and treating graft-vs-host-disease (GVHD) and autoimmune diseases by administration of an antibody, antigen-binding fragment thereof, ADC, or soluble ligand capable of binding an antigen expressed by hematopoietic cells. This administration can cause the selective depletion of a population of exogenous T cells that are reactive against the host. The invention is based in part on the discovery that an antibody, antigen-binding fragment thereof, ADC, or soluble ligand, capable of binding CD137 can be administered to a patient in order to prevent and treat GVHD and autoimmune diseases, such as those arising from hematopoietic stem cell transplant therapy.

Prevention and treatment of GVHD, due to the administration of anti-CD137 antibodies, antigen-binding fragments thereof, ADCs, or soluble ligands can manifest in a variety of clinical symptoms (see, e.g., McDonald, Blood. 127: 1544-1440, 2016, and Flowers et al., Blood. 125:606-615, the disclosure of which is incorporated herein by reference as it pertains, but is not limited to, the measurable clinical features of acute and chronic GVHD, respectively). Prevention and treatment of GVHD and autoimmune diseases, due to the administration of anti-CD137 antibodies, antigen-binding fragments thereof, or ADCs, can manifest in a variety of empirical measurements. For instance, depletion of CD137+ positive cells can be determined by fluorescence activated cell sorting (FACS) analysis methods known in the art to measure CD137+ white blood cell counts in peripheral blood during a post-transplant period, and/or by measuring recovery of marrow cells by donor cells in a bone marrow aspirate sample. Enumeration of the interferon-γ (IFN-γ)-producing T cells in the peripheral blood of recipients can assess the efficacy of anti-CD137 against GVHD and autoimmune diseases. The alteration of immune cell populations, as determined by FACS, can be indicative of GVHD or an autoimmune disease. Finally, genetic and proteomic biomarkers taken from the patient can also indicate GVHD or an autoimmune disease.

The sections that follow provide a description of antibodies, antigen-binding fragments thereof, ADCs, or soluble ligands that can be administered to a patient suffering from or at risk for GVHD or an autoimmune disease as well as methods of administering such therapeutics to the patient.

Anti-CD137 Antibodies and Ligands

The present invention is based in part on the discovery that antibodies, antigen-binding fragments thereof, and soluble ligands capable of binding CD137 (also referred to as CDw137, TNFRSF9, 4-1BB, and ILA) can be used as therapeutic agents to prevent and treat GVHD from hematopoietic stem cells in a patient suffering from or at risk for GVHD or an autoimmune disease. Additionally, it has been discovered that ligands that bind CD137, such as human CD137L, can be used as a therapeutic agent to prevent or treat patient suffering from or at risk for GVHD. These ligands, such as soluble human CD137, can be covalently bound to an effector domain, such as an Fc domain, for instance, in order to promote antibody-dependent cell-mediated cytotoxicity (ADCC).

T cells have been shown to express CD137, as this antigen is a transmembrane TNF receptor superfamily of costimulatory molecules and is expressed on a variety of hematopoietic cells and promotes T cell activation and regulates proliferation and survival of T cells (see, e.g., Cannons et al., J. Immunol. 167:1313-1324, 2001, the disclosure of which is incorporated herein by reference as it pertains to the expression of CD137 by T cells). Antibodies, antigen-binding fragments thereof, and ligands can be identified using techniques known in the art and described herein, such as by immunization, computational modeling techniques, and in vitro selection methods, such as the phage display and cell-based display platforms described below.

Anti-CD137 antibodies that can be used to prevent and treat GVHD or an autoimmune disease by the methods disclosed herein include those that have one or more, or all, of the following CDRs:
a. a CDR-H1 having the amino acid sequence STYWIS (SEQ ID NO: 1);
b. a CDR-H2 having the amino acid sequence KIYPGD-SYTNYSPSFQG (SEQ ID NO: 2);
c. a CDR-H3 having the amino acid sequence RGY-GIFDY (SEQ ID NO: 3);
d. a CDR-L1 having the amino acid sequence SGD-NIGDQYAH (SEQ ID NO: 4)
e. a CDR-L2 having the amino acid sequence QDKNRPS (SEQ ID NO: 5); and
f. a CDR-L3 having the amino acid sequence ATYTGF-GSLAV (SEQ ID NO: 6)

Additional anti-CD137 antibodies that can be used to prevent and treat GVHD and autoimmune diseases by the methods disclosed herein include those that have one or more, or all, of the following CDRs:
a. a CDR-H1 having the amino acid sequence STYWIS (SEQ ID NO: 1);
b. a CDR-H2 having the amino acid sequence KIYPGD-SYTNYSPSFQG (SEQ ID NO: 2);
c. a CDR-H3 having the amino acid sequence RGY-GIFDY (SEQ ID NO: 3);
d. a CDR-L1 having the amino acid sequence SGD-NIGDQYAH (SEQ ID NO: 4)
e. a CDR-L2 having the amino acid sequence QDKNRPS (SEQ ID NO: 5); and
f. a CDR-L3 having the amino acid sequence STYTFVG-FTTV (SEQ ID NO: 7)

Additional anti-CD137 antibodies include those that have one or more, or all, of the following CDRs:
a. a CDR-H1 having the amino acid sequence NSYAIS (SEQ ID NO: 8);
b. a CDR-H2 having the amino acid sequence GIIPGF-GTANYAQKFQG (SEQ ID NO: 9);
c. a CDR-H3 having the amino acid sequence RKNEEDGGFDH (SEQ ID NO: 10);
d. a CDR-L1 having the amino acid sequence SGDNL-GDYYAS (SEQ ID NO: 11)
e. a CDR-L2 having the amino acid sequence DDSNRPS (SEQ ID NO: 12); and
f. a CDR-L3 having the amino acid sequence QTWDGTLHFV (SEQ ID NO: 13)

Additional anti-CD137 antibodies or ADCs include those that have one or more, or all, of the following CDRs:
a. a CDR-H1 having the amino acid sequence SDYYMH (SEQ ID NO: 14);
b. a CDR-H2 having the amino acid sequence VISGSGSNTYYADSVKG (SEQ ID NO: 15);
c. a CDR-H3 having the amino acid sequence RLYAQFEGDF (SEQ ID NO: 16);
d. a CDR-L1 having the amino acid sequence SGDNIG-SKYVS (SEQ ID NO: 17)
e. a CDR-L2 having the amino acid sequence SDSERPS (SEQ ID NO: 18); and
f. a CDR-L3 having the amino acid sequence QSWDG-SISRV (SEQ ID NO: 19)

The foregoing antibodies are described, e.g., in U.S. Pat. No. 9,468,678, the disclosure of which is incorporated herein by reference as it pertains to anti-CD137 antibodies and antigen-binding fragments thereof. The antibodies and fragments thereof disclosed in U.S. Pat. No. 9,468,678 can be used in conjunction with the methods disclosed herein.

In another embodiment, an anti-CD137 antibody that may be used in the methods and compositions (including ADCs) described herein is the murine anti-CD137 antibody BBK2 (Thermo Fisher; MS621 PABX) or an anti-CD137 antibody comprising antigen binding regions corresponding to the BBK2 antibody. The BBK2 antibody (which may also be referred to as a BBK-2 antibody or an anti-4-1 BB antibody), is a mouse monoclonal antibody (IgG1, kappa) that binds to the ectodomain of human 4-1BB recombinant protein (4-1 BB is also known as CD137). In certain embodiments, the methods and compositions of the disclosure include an anti-CD137 antibody comprising the binding regions (e.g., the CDRs) of the BBK2 antibody. In another embodiment, the methods and compositions of the disclosure comprise an antibody that competitively inhibits the binding of the BBK2 antibody to its epitope on CD137. In certain embodiments, the anti-CD137 antibody is humanized BBK2 or chimeric BBK2.

In one embodiment, the methods and compositions described herein include a chimeric anti-CD137 (ch-BBK2) antibody comprising the variable heavy and light chain regions of BBK2. In certain embodiments, the chimeric BBK2 antibody is an IgG1 antibody comprising human constant regions. The heavy chain amino acid sequence of ch-BBK2 is described in SEQ ID NO: 23, and the light chain amino acid sequence of ch-BBK2 is described in SEQ ID NO: 24. The CDR regions (CDR1, CDR2, and CDR3) of each of the heavy and light chain sequences are described in bold below. The variable regions are italicized.

(SEQ ID NO: 23)
QVQLQQPGAELVRPGASVKLSCKASGYTFTSYWINWVKQRPGQGLEWIGN
IYPSDSYTNYNQKFKDKATLTVDKSSNTVYMQLNSPTSEDSAVYYCTRNG
VEGYPHYYAMEYWGQGTSVTVSSASTKGPSVFPLAPSSKSTSGGTAALGC
LVKDYFPEPVTVSWNSGALTSGVHTFPAVLQSSGLYSLSSVVTVPSSSLG
TQTYICNVNHKPSNTKVDKKVEPKSCDKTHTCPPCPAPELLGGPSVFLFP
PKPKDTLMISRTPEVTCVVVDVSHEDPEVKFNWYVDGVEVHNAKTKPREE
QYNSTYRVVSVLTVLHQDWLNGKEYKCKVSNKALPAPIEKTISKAKGQPR
EPQVYTLPPSRDELTKNQVSLTCLVKGFYPSDIAVEWESNGQPENNYKTT
PPVLDSDGSFFLYSKLTVDKSRWQQGNVFSCSVMHEALHNHYTQKSLSLS
PGK (SEQ ID NO: 24)
DIQMTQTTSALSASLGDRVTIGCRASQDLSNHLYWYQQKPDGTVKLLIYY
TSRLHSGVPSRFSGSGSGTDYSLTIRNLEQEDVATYFCQQGYTLPYTFGG
GTKLEIKRTVAAPSVFIFPPSDEQLKSGTASVVCLLNNFYPREAKVQWKV
DNALQSGNSQESVTEQDSKDSTYSLSSTLTLSKADYEKHKVYACEVTHQG
LSSPVTKSFNRGEC

The foregoing CDR regions (and BBK2 antibody) are described in Lee et al. (2002) *European J of Immunogenetics* 29(5):449-452. Thus, in one embodiment, the VH CDR amino acid sequences of anti-CD137 antibody BBK2 (including ch-BBK2) are as follows: SGYTFTSYW (VH CDR1; SEQ ID NO: 33); NIYPSDSYT (VH CDR2; SEQ ID NO: 34) and TRNGVEGYPHYYAME (VH CDR3; SEQ ID NO: 35). The VL CDR amino acid sequences of anti-CD137 antibody BBK2 (including ch-BBK2) are as follows: SQDL-SNH (VL CDR1; SEQ ID NO: 36); YYTS (VL CDR2; SEQ ID NO: 37) and CQQGYTLPY (VL CDR3; SEQ ID NO: 38).

Alternatively, the CDR regions of BBK2 can be defined according to Kabat numbering. CDRs as defined by Kabat numbering are described below for each of the heavy and light chain sequences (described in bold below). The variable regions of BBK2 are italicized.

*QVQLQQPGAELVRPGASVKLSCKASGYTFT**SYWINWVKQRPGQGLEWIGN*
*IYPSDSYTNYNQKFKDKATLTVDKSSNTVYMQLNSPTSEDSAVYYCTRNG*
*VEGYPHYYAMEY**WGQGTSVTVSS*ASTKGPSVFPLAPSSKSTSGGTAALGC
LVKDYFPEPVTVSWNSGALTSGVHTFPAVLQSSGLYSLSSVVTVPSSSLG
TQTYICNVNHKPSNTKVDKKVEPKSCDKTHTCPPCPAPELLGGPSVFLFP
PKPKDTLMISRTPEVTCVVVDVSHEDPEVKFNWYVDGVEVHNAKTKPREE
QYNSTYRVVSVLTVLHQDWLNGKEYKCKVSNKALPAPIEKTISKAKGQPR
EPQVYTLPPSRDELTKNQVSLTCLVKGFYPSDIAVEWESNGQPENNYKTT
PPVLDSDGSFFLYSKLTVDKSRWQQGNVFSCSVMHEALHNHYTQKSLSLS
PGK (ch-BBK2 heavy chain; SEQ ID NO: 23)
*DIQMTQTTSALSASLGDRVTIGC**RASQDLSNHLYWYQQKPDGTVKLLIYY*
*TSRLHSGVPSRFSGSGSGTDYSLTIRNLEQEDVATYFCQQGYTLPYT**FGG*
*GTKLEIK*RTVAAPSVFIFPPSDEQLKSGTASVVCLLNNFYPREAKVQWKV
DNALQSGNSQESVTEQDSKDSTYSLSSTLTLSKADYEKHKVYACEVTHQG
LSSPVTKSFNRGEC (ch-BBK2 light chain; SEQ ID NO: 24)

Thus, in one embodiment, the VH CDR amino acid sequences of anti-CD137 antibody BBK2 (including ch-BBK2) are as follows: SYWIN (VH CDR1; SEQ ID NO: 25); NIYPSDSYTNYNQKFKD (VH CDR2; SEQ ID NO: 26) and NGVEGYPHYYAMEY (VH CDR3; SEQ ID NO: 27), and the VL CDR amino acid sequences of anti-CD137 antibody BBK2 (including ch-BBK2) are as follows: RASQDLSNHLY (VL CDR1; SEQ ID NO: 29); YTSRLHS (VL CDR2; SEQ ID NO: 30) and QQGYTLPYT (VL CDR3; SEQ ID NO: 31).

The heavy chain variable region of BBK2 is set forth in SEQ ID NO: 28 as QVQLQQPGAELVRPGASVKLSCK-ASGYTFTSYWINWVKQRPGQGLEWIGNIYPSDSYT-NYNQK FKDKATLTVDKSSNTVYMQLNSPTSED-SAVYYCTRNGVEGYPHYYAMEYWGQGTSVTVSS.

The light chain variable region of BBK2 is set forth in SEQ ID NO: 32 as DIQMTQTTSAL-SASLGDRVTIGCRASQDLSNHLYWYQQKPDGT-VKLLIYYTSRLHSGVPSRFSG SGSGTDYSLTIRN-LEQEDVATYFCQQGYTLPYTFGGGTKLEIK. Anti-CD137 antibodies (including anti-CD137 ADCs) can comprise the heavy and light chain variable region amino acid sequences as set forth in SEQ ID Nos: 28 and 32, respectively.

In one embodiment, the anti-CD137 antibody, e.g., a chimeric (ch-BBK2) antibody or a humanized BBK2 antibody, comprises a heavy chain variable region comprising a CDR1 comprising the amino acid sequence of SEQ ID NO: 25, a CDR2 comprising the amino acid sequence of SEQ ID NO: 26, and a CDR3 comprising the amino acid sequence of SEQ ID NO: 27; and comprises a light chain variable region comprising a CDR1 comprising the amino acid sequence of SEQ ID NO: 29, a CDR2 comprising the amino acid sequence of SEQ ID NO: 30, and a CDR3 comprising the amino acid sequence of SEQ ID NO: 31.

In one embodiment, the anti-CD137 antibody, e.g., a chimeric (ch-BBK2) antibody or a humanized BBK2 antibody, comprises a heavy chain variable region comprising a CDR1 comprising the amino acid sequence of SEQ ID NO: 33, a CDR2 comprising the amino acid sequence of SEQ ID NO: 34, and a CDR3 comprising the amino acid sequence of SEQ ID NO: 35; and comprises a light chain variable region comprising a CDR1 comprising the amino acid sequence of SEQ ID NO: 36, a CDR2 comprising the amino acid sequence of SEQ ID NO: 37, and a CDR3 comprising the amino acid sequence of SEQ ID NO: 38.

Thus, BBK2, humanized BBK2, or chimeric BBK2 antibodies can be used in the anti-CD137 ADCs and methods described herein. Each of these antibodies can be conjugated to any of the cytotoxin described below using methods known in the art and those described herein.

Other anti-CD137 antibodies that can be used in conjunction with a cytotoxin described herein can be identified using techniques known in the art (e.g., hybridoma production). Hybridomas can be prepared using a murine system. Protocols for immunization and subsequent isolation of splenocytes for fusion are known in the art. Fusion partners and procedures for hybridoma generation are also known. Human anti-CD137 antibodies can also be generated in the HuMAb-Mouse® or XenoMouse™. In making anti-CD137 antibodies, the CD137 antigen is isolated and/or purified. The CD137 antigen may be a fragment of CD137 from the extracellular domain of CD137. Immunization of animals can be performed by any method known in the art. See, e.g., Harlow and Lane, Antibodies: A Laboratory Manual, New York: Cold Spring Harbor Press, 1990. Methods for immunizing animals such as mice, rats, sheep, goats, pigs, cattle and horses are well known in the art. See, e.g., Harlow and Lane, supra, and U.S. Pat. No. 5,994,619. The CD137 antigen may be administered with an adjuvant to stimulate the immune response. Adjuvants known in the art include complete or incomplete Freund's adjuvant, RIBI (muramyl dipeptides) or ISCOM (immunostimulating complexes). After immunization of an animal with a CD137 antigen, antibody-producing immortalized cell lines are prepared from cells isolated from the immunized animal. After immunization, the animal is sacrificed and lymph node and/or splenic B cells are immortalized by methods known in the art (e.g., oncogene transfer, oncogenic virus transduction, exposure to carcinogenic or mutating compounds, fusion with an immortalized cell, e.g., a myeloma cell, and inactivating a tumor suppressor gene. See, e.g., Harlow and Lane, supra. Hybridomas can be selected, cloned and further screened for desirable characteristics, including robust growth, high antibody production and desirable antibody characteristics.

Anti-CD137 antibodies can be generated from an isolated nucleic acid molecule that comprises a nucleotide sequence encoding an amino acid sequence of a CD137 binding molecule provided by the present disclosure. The amino acid sequence encoded by the nucleotide sequence may be any portion of an antibody, such as a CDR, a sequence comprising one, two, or three CDRs, a variable region of a heavy chain, variable region of a light chain, or may be a full-length heavy chain or full length light chain. A nucleic acid of the disclosure can be, for example, DNA or RNA, and may or may not contain intronic sequences. Typically, the nucleic acid is a cDNA molecule.

In addition to antibodies, and antigen-binding fragments, soluble CD137 ligands, such as human CD137 ligand, can be administered to a patient according to the methods described herein to condition a patient prior to hematopoietic stem cell transplant therapy. For instance, CD137 ligands, such as human CD137 ligand, can be conjugated to a cytotoxin (e.g., according to the methods described below or known in the art) or another effector molecule, such as an Fc domain. Maytansine cytotoxins for use with the methods described herein include, for example, human CD137 ligand-IgG1 Fc conjugates, human CD137 ligand-IgG2 Fc conjugates, human CD137 ligand-IgG3 Fc conjugates, human CD137 ligand-IgG4 Fc conjugates, human CD137 ligand-IgA Fc conjugates, human CD137 ligand-IgE Fc conjugates, human CD137 ligand-IgM Fc conjugates, and human CD137 ligand-IgD Fc conjugates.

Antibodies and ligands for use in conjunction with the compositions and methods described herein include variants of those antibodies described above, such as antibody fragments that contain or lack an Fc domain, as well as humanized variants of non-human antibodies described herein and antibody-like protein scaffolds (e.g., $^{10}$Fn3 domains) containing one or more, or all, of the CDRs or equivalent regions thereof of an antibody, antibody fragment, or soluble ligand described herein.

Methods of Identifying Antibodies and Ligands

Methods for high throughput screening of libraries of antibodies, antibody fragments, and ligands for molecules capable of binding CD137 can be used to identify and affinity mature agents that are, for example, useful for preventing and treating GVHD or autoimmune diseases. Such methods include in vitro display techniques known in the art, such as phage display, bacterial display, yeast display, mammalian cell display, ribosome display, mRNA display, and cDNA display, among others. The use of phage display to isolate antibodies, antigen-binding fragments, or ligands that bind biologically relevant molecules has been reviewed, for example, in Felici et al., Biotechnol. Annual Rev. 1:149-183, 1995; Katz, Annual Rev. Biophys. Biomol. Struct. 26:27-45, 1997; and Hoogenboom et al., Immunotechnology 4:1-20, 1998, the disclosures of each of which are incorporated herein by reference as they pertain to in vitro display techniques. Randomized combinatorial peptide libraries have been constructed to select for polypeptides that bind cell surface antigens as described in Kay, Perspect. Drug Discovery Des. 2:251-268, 1995 and Kay et al., Mol. Divers. 1:139-140, 1996, the disclosures of each of which are incorporated herein by reference as they pertain to the discovery of antigen-binding molecules. Proteins, such as multimeric proteins, have been successfully phage-displayed as functional molecules (see, for example, EP 0349578; EP 4527839; and EP 0589877, as well as Chiswell and McCafferty, Trends Biotechnol. 10:80-84 1992, the disclosures of each of which are incorporated herein by reference as they pertain to the use of in vitro display techniques for the discovery of antigen-binding molecules. In addition, functional antibody fragments, such as Fab and scFv fragments, have been expressed in in vitro display formats (see, for example, McCafferty et al., Nature 348: 552-554, 1990; Barbas et al., Proc. Natl. Acad. Sci. USA 88:7978-7982, 1991; and Clackson et al., Nature 352:624-628, 1991, the disclosures of each of which are incorporated herein by reference as they pertain to in vitro display platforms for the discovery of antigen-binding molecules). Human anti-CD137 antibodies can also be generated, for example, in the HuMAb-Mouse® or XenoMouse™. These techniques, among others, can be used to identify and improve the affinity of antibodies, antibody fragments, and ligands that bind CD137 that can in turn be used to deplete hematopoietic cells in a patient.

In addition to in vitro display techniques, computational modeling techniques can be used to design and identify anti-CD137 antibodies, antibody fragments and ligands in silico, for instance, using the procedures described in US 2013/0288373, the disclosure of which is incorporated herein as it pertains to molecular modeling methods for identifying anti-CD137 antibodies. For example, using computational modeling techniques, one of skill in the art can screen libraries of antibodies, antibody fragments, and ligands in silico for molecules capable of binding specific epitopes on CD137, such as extracellular epitopes of CD137.

Additional techniques can be used to identify antibodies, antigen-binding fragments, and ligands thereof that bind CD137 on the surface of a cell (e.g., a T cell) and that are internalized by the cell, for instance, by receptor-mediated endocytosis. For example, the in vitro display techniques described above can be adapted to screen for antibodies, antigen-binding fragments thereof, and ligands that bind CD137 on the surface of a hematopoietic stem cell and that are subsequently internalized. Phage display represents one such technique that can be used in conjunction with this screening paradigm. To identify anti-CD137 antibodies, fragments thereof, and ligands that bind CD137 and are subsequently internalized by hematopoietic stem cells, one of skill in the art can use the phage display techniques described in Williams et al., Leukemia 19:1432-1438, 2005, the disclosure of which is incorporated herein by reference in its entirety. For example, using mutagenesis methods known in the art, recombinant phage libraries can be produced that encode antibodies, antibody fragments, such as scFv fragments, Fab fragments, diabodies, triabodies, and $^{10}$Fn3 domains, among others, or ligands that contain randomized amino acid cassettes (e.g., in one or more, or all, of the CDRs or equivalent regions thereof or an antibody or antibody fragment). The framework regions, hinge, Fc domain, and other regions of the antibodies or antibody fragments may be designed such that they are non-immunogenic in humans, for instance, by virtue of having human germline antibody sequences or sequences that exhibit only minor variations relative to human germline antibodies.

Using phage display techniques described herein or known in the art, phage libraries containing randomized antibodies, antibody fragments, or ligands covalently bound to the phage particles can be incubated with CD137 antigen, for instance, by first incubating the phage library with blocking agents (such as, for instance, milk protein, bovine serum albumin, and/or IgG so as to remove phage encoding antibodies, fragments thereof, or ligands that exhibit non-specific protein binding and phage that encode antibodies or fragments thereof that bind Fc domains, and then incubating the phage library with a population of hematopoietic stem cells, which are CD137+. The phage library can be incubated with the hematopoietic stem cells for a time sufficient to allow CD137 specific antibodies, antigen-binding fragments thereof, or ligands to bind cell-surface CD137 and to subsequently be internalized by the hematopoietic stem cells (e.g., from 30 minutes to 6 hours at 4° C., such as 1 hour at 4° C.). Phage containing antibodies, fragments thereof, or ligands that do not exhibit sufficient affinity for CD137 so as to permit binding to, and internalization by, hematopoietic stem cells can subsequently be removed by washing the cells, for instance, with cold (4° C.) 0.1 M glycine buffer at pH 2.8. Phage bound to antibodies, fragments thereof, or ligands that have been internalized by the hematopoietic stem cells can be identified, for instance, by lysing the cells and recovering internalized phage from the cell culture medium. The phage can then be amplified in bacterial cells, for example, by incubating bacterial cells with recovered phage in 2×YT medium using methods known in the art. Phage recovered from this medium can then be characterized, for instance, by determining the nucleic acid sequence of the gene(s) encoding the antibodies, fragments thereof, or ligands inserted within the phage genome. The encoded antibodies, fragments thereof, or ligands can subsequently be prepared de novo by chemical synthesis (for instance, of antibody fragments, such as scFv fragments, or CD137 ligands) or by recombinant expression (for instance, of full-length antibodies).

The internalizing capacity of the prepared antibodies, fragments thereof, or ligands can be assessed, for instance, using radionuclide internalization assays known in the art. For example, anti-CD137 antibodies, fragments thereof, or ligands identified using in vitro display techniques described herein or known in the art can be functionalized by incorporation of a radioactive isotope, such as $^{18}$F, $^{75}$Br, $^{77}$Br, $^{122}$I, $^{123}$I, $^{124}$I, $^{125}$I, $^{129}$I, $^{131}$I, $^{211}$At, $^{67}$Ga, $^{111}$In, $^{99}$Tc, $^{169}$Yb, $^{186}$Re, $^{64}$Cu, $^{67}$Cu, $^{177}$Lu, $^{77}$As, $^{72}$As, $^{86}$Y, $^{90}$Y, $^{89}$Zr, $^{212}$Bi, $^{213}$Bi, or $^{225}$Ac. For instance, radioactive halogens, such as $^{18}$F, $^{75}$Br, $^{77}$Br, $^{122}$I, $^{123}$I, $^{124}$I, $^{125}$I, $^{129}$I, $^{131}$I, $^{211}$At, can be incorporated into antibodies, fragments thereof, or ligands using beads, such as polystyrene beads, containing electrophilic halogen reagents (e.g., Iodination Beads, Thermo Fisher Scientific, Inc., Cambridge, Mass.). Radiolabeled antibodies, fragments thereof, ADCs, or ligands can be incubated with hematopoietic stem cells for a time sufficient to permit internalization (e.g., from 30 minutes to 6 hours at 4° C., such as 1 hour at 4° C.). The cells can then be washed to remove non-internalized antibodies or fragments thereof, (e.g., using cold (4° C.) 0.1 M glycine buffer at pH 2.8). Internalized antibodies, fragments thereof, or ligands can be identified by detecting the emitted radiation (e.g., γ-radiation) of the resulting hematopoietic stem cells in comparison with the emitted radiation (e.g., γ-radiation) of the recovered wash buffer. The foregoing internalization assays can also be used to characterize ADCs.

Antibodies may be produced using recombinant methods and compositions, e.g., as described in U.S. Pat. No. 4,816,567. In one embodiment, isolated nucleic acid encoding an anti-CD137 antibody described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., Y0, NS0, Sp20 cell). In one embodiment, a method of making an anti-CLL-1 antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an anti-CD137 antibody, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, Methods in Molecular Biology, Vol. 248 (B. K. C. Lo, ed., Humana Press, Totowa, N.J., 2003), pp. 245-254, describing expression of antibody fragments in E. coli.) After expression, the antibody may be isolated from the bacterial cell paste in a soluble fraction and can be further purified.

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., J. Gen Virol. 36:59 (1977)); baby hamster kidney cells (BHK); mouse sertoli cells (TM4 cells as described, e.g., in Mather, Biol. Reprod. 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., Annals N.Y. Acad. Sci. 383:44-68 (1982); MRC 5 cells; and FS4 cells. Other useful mammalian host cell lines include Chinese hamster ovary (CHO) cells, including DHFR-CHO cells (Urlaub et al., Proc. Natl. Acad. Sci. USA 77:4216 (1980)); and myeloma cell lines such as Y0, NS0 and Sp2/0. For a review of certain mammalian host cell lines suitable for antibody production, see, e.g., Yazaki and Wu, Methods in Molecular Biology, Vol. 248 (B. K. C. Lo, ed., Humana Press, Totowa, N.J.), pp. 255-268 (2003).

Drug-Antibody Conjugates

Cytotoxins

Antibodies, antigen-binding fragments thereof, and ligands described herein (e.g., antibodies, antigen-binding fragments thereof, and soluble ligands that recognize and bind CD137) can be conjugated (or linked) to a cytotoxin, such as a microtubule-binding agent (for instance, maytansine or a maytansinoid), an amatoxin, *pseudomonas* exotoxin A, deBouganin, diphtheria toxin, such as α-amanitin, saporin, an auristatin, an anthracycline, a calicheamicin, irinotecan, SN-38, a duocarmycin, a pyrrolobenzodiazepine, a pyrrolobenzodiazepine dimer, an indolinobenzodiazepine, and an indolinobenzodiazepine dimer, or a variant thereof, or another cytotoxic compound described herein or known in the art in order to promote the depletion of hematopoietic cells, such as a host-reactive T cell, upon administration to a patient. In some embodiments, the cytotoxic molecule is conjugated to an internalizing anti-CD137 antibody, antigen-binding fragment thereof or soluble ligand, such that following the cellular uptake of the antibody, fragment thereof, or soluble ligand, the cytotoxin may access its intracellular target and mediate hematopoietic cell death. Additional cytotoxins suitable for use with the compositions and methods described herein include DNA-intercalating agents, (e.g., anthracyclines), agents capable of disrupting the mitotic spindle apparatus (e.g., vinca alkaloids, maytansine, maytansinoids, and derivatives thereof), RNA polymerase inhibitors (e.g., an amatoxin, such as α-amanitin, and derivatives thereof), agents capable of disrupting protein biosynthesis (e.g., agents that exhibit rRNA N-glycosidase activity, such as saporin and ricin A-chain), among others known in the art.

Maytansinoids

Anti-CD137 antibodies can be conjugated to a cytotoxin that is a microtubule binding agent. In some embodiments, the cytotoxin is a maytansine, maytansinoid or maytansinoid analog. Maytansinoids are microtubule binding agents that prohibit tubulin polymerization. Examples of suitable maytansinoids include esters of maytansinol, synthetic maytansinol, and maytansinol analogs and derivatives. Included are any drugs that inhibit microtubule formation and that are highly toxic to mammalian cells, as are maytansinoids, maytansinol, and maytansinol analogs, and derivatives.

Examples of suitable maytansinol esters include those having a modified aromatic ring and those having modifications at other positions. Such suitable maytansinoids are disclosed in U.S. Pat. Nos. 4,137,230; 4,151,042; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,362,663; 4,364,866; 4,424,219; 4,450,254; 4,322,348; 4,362,663; 4,371,533; 5,208,020; 5,416,064; 5,475,092; 5,585,499; 5,846,545; 6,333,410; 7,276,497; and 7,473,796, the disclosures of each of which are incorporated herein by reference as they pertain to maytansinoids and derivatives thereof.

In some embodiments, the immunoconjugates (ADCs) of the invention utilize the thiol-containing maytansinoid (DM1), formally termed $N^{2'}$-deacetyl-$N^{2'}$-(3-mercapto-1-oxopropyl)-maytansine, as the cytotoxic agent. DM1 is represented by the following structural formula (I):

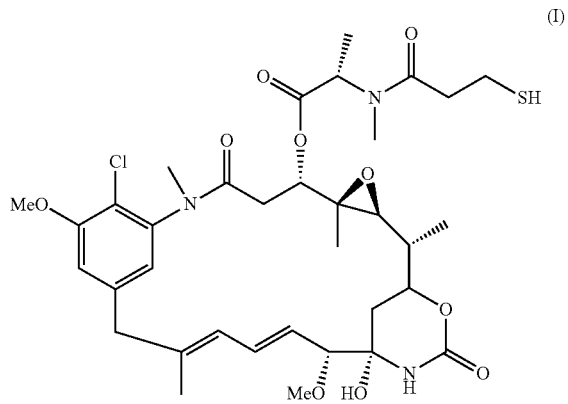 [SMILES: COc1cc2cc(c1Cl)N(C)C(=O)C[C@H](OC(=O)[C@H](C)N(C)C(=O)CCS)[C@]1(C)O[C@H]1[C@H](C)C1C[C@@](O)(NC(=O)O1)[C@H](OC)/C=C/C=C(\C)C2]

(I)

In another embodiment, the conjugates of the present invention utilize the thiol-containing maytansinoid $N^{2'}$-deacetyl-$N^{2'}$(4-methyl-4-mercapto-1-oxopentyl)-maytansine (e.g., DM4) as the cytotoxic agent. DM4 is represented by the following structural formula (II):

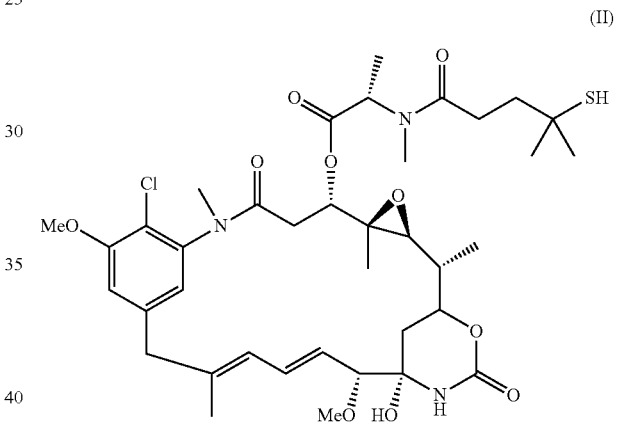

(II)

Another maytansinoid comprising a side chain that contains a sterically hindered thiol bond is $N^{2'}$-deacetyl-N-$^{2'}$(4-mercapto-1-oxopentyl)-maytansine (termed DM3), represented by the following structural formula (III):

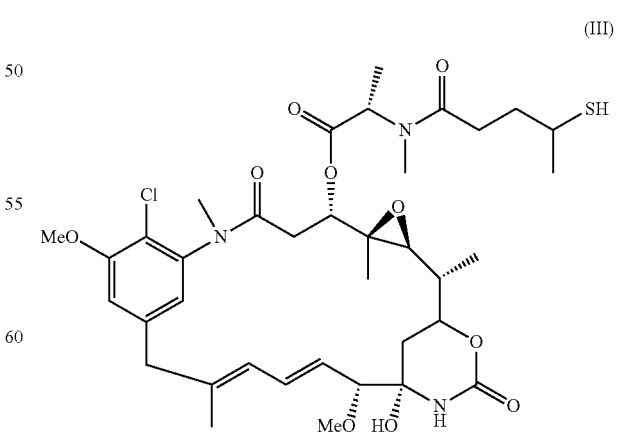

(III)

Each of the maytansinoids taught in U.S. Pat. Nos. 5,208,020 and 7,276,497, can also be used in the conjugate of the present invention. In this regard, the entire disclosure of U.S. Pat. Nos. 5,208,020 and 7,276,697 is incorporated herein by reference.

Many positions on maytansinoids can serve as the position to chemically link the linking moiety. For example, the C-3 position having a hydroxyl group, the C-14 position modified with hydroxymethyl, the C-15 position modified with hydroxy and the C-20 position having a hydroxy group are all expected to be useful. In some embodiments, the C-3 position serves as the position to chemically link the linking moiety, and in some particular embodiments, the C-3 position of maytansinol serves as the position to chemically link the linking moiety.

The invention also includes various isomers and mixtures of maytansinoids and conjugates. Certain compounds and conjugates of the present invention may exist in various stereoisomeric, enantiomeric, and diastereomeric forms. Several descriptions for producing such antibody-maytansinoid conjugates are provided in U.S. Pat. Nos. 5,208,020, 5,416,064 6,333,410, 6,441,163, 6,716,821, and 7,368,565, each of which is incorporated herein in its entirety.

A therapeutically effective number of maytansinoid molecules bound per antibody molecule can be determined by measuring spectrophotometrically the ratio of the absorbance at 252 nm and 280 nm. An average of 3 to 4 maytansinoid molecules conjugated per antibody molecule can enhancing cytotoxicity of target cells without negatively affecting the function or solubility of the antibody, although one molecule of toxin/antibody can enhance cytotoxicity over antibody alone. The average number of maytansinoid molecules/antibody or antigen binding fragment thereof, or soluble ligand, can be, for example, 1-10 or 2-5.

Amatoxins

In some embodiments, the cytotoxin is an amatoxin or derivative thereof, such as α-amanitin, β-amanitin, γ-amanitin, ε-amanitin, amanin, amaninamide, amanullin, amanullinic acid, or proamanullin. For instance, suitable cytotoxins that may be conjugated to an antibody, antigen-binding fragment thereof, or soluble ligand described herein include an amatoxin or derivative thereof represented by formula (IV)

$R_2$ is H, OH, $OR_B$, or $OR_C$;
$R_A$ and $R_B$, together with the oxygen atoms to which they are bound, combine to form an optionally substituted 5-membered heterocycloalkyl group;
$R_3$ is H, $R_C$, or $R_D$;
$R_4$ is H, OH, $OR_C$, $OR_D$, $R_C$, or $R_D$;
$R_5$ is H, OH, $OR_C$, $OR_D$, $R_C$, or $R_D$;
$R_6$ is H, OH, $OR_C$, $OR_D$, $R_C$, or $R_D$;
$R_7$ is H, OH, $OR_C$, $OR_D$, $R_C$, or $R_D$;
$R_8$ is OH, $NH_2$, $OR_C$, $OR_D$, $NHR_C$, or $NR_CR_D$;
$R_9$ is H, OH, $OR_C$, or $OR_D$;
X is —S—, —S(O)—, or —SO$_2$—;
$R_C$ is L-Z;
$R_D$ is optionally substituted $C_1$-$C_6$ alkyl, optionally substituted $C_1$-$C_6$ heteroalkyl, optionally substituted $C_2$-$C_6$ alkenyl, optionally substituted $C_2$-$C_6$ heteroalkenyl, optionally substituted $C_2$-$C_6$ alkynyl, optionally substituted $C_2$-$C_6$ heteroalkynyl, optionally substituted cycloalkyl, optionally substituted heterocycloalkyl, optionally substituted aryl, or optionally substituted heteroaryl;
L is a linker, such as optionally substituted $C_1$-$C_6$ alkylene, optionally substituted $C_1$-$C_6$ heteroalkylene, optionally substituted $C_2$-$C_6$ alkenylene, optionally substituted $C_2$-$C_6$ heteroalkenylene, optionally substituted $C_2$-$C_6$ alkynylene, optionally substituted $C_2$-$C_6$ heteroalkynylene, optionally substituted cycloalkylene, optionally substituted heterocycloalkylene, optionally substituted arylene, or optionally substituted heteroarylene; and
Z is a chemical moiety that forms a coupling reaction between a reactive substituent present on L and a reactive substituent present within an antibody, antigen-binding fragment thereof, or soluble ligand that binds CD137.

In some embodiments, the cytotoxin contains one $R_C$ substituent.

In some embodiments, the cytotoxin is an amatoxin or derivative thereof represented by formula (IVA)

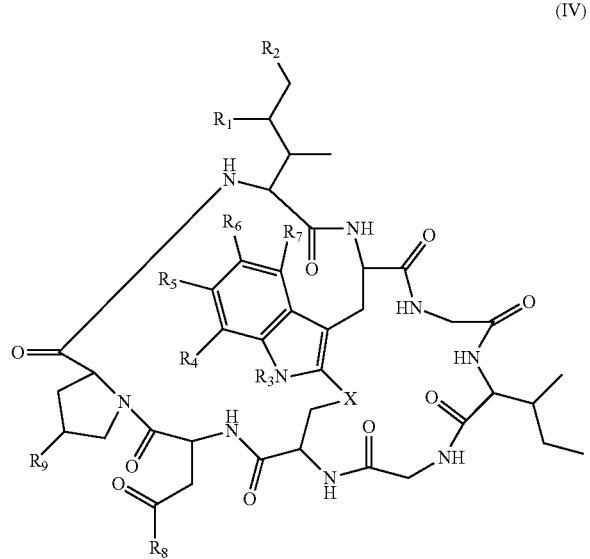

(IV)

wherein $R_1$ is H, OH, $OR_A$, or $OR_C$;

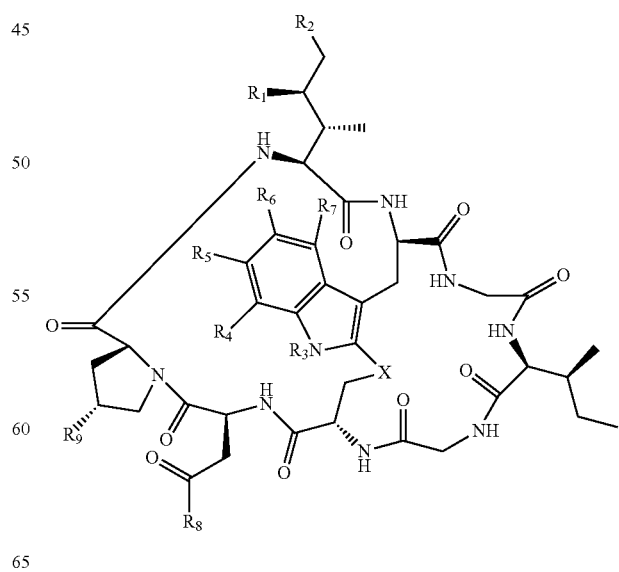

(IVA)

wherein $R_1$ is H, OH, $OR_A$, or $OR_C$;
$R_2$ is H, OH, $OR_B$, or $OR_C$;

$R_A$ and $R_B$, together with the oxygen atoms to which they are bound, combine to form an optionally substituted 5-membered heterocycloalkyl group;

$R_3$ is H, $R_C$, or $R_D$;

$R_4$ is H, OH, $OR_C$, $OR_D$, $R_C$, or $R_D$;

$R_5$ is H, OH, $OR_C$, $OR_D$, $R_C$, or $R_D$;

$R_6$ is H, OH, $OR_C$, $OR_D$, $R_C$, or $R_D$;

$R_7$ is H, OH, $OR_C$, $OR_D$, $R_C$, or $R_D$;

$R_8$ is OH, $NH_2$, $OR_C$, $OR_D$, $NHR_C$, or $NR_CR_D$;

$R_9$ is H, OH, $OR_C$, or $OR_D$;

X is —S—, —S(O)—, or —$SO_2$—;

$R_C$ is L-Z;

$R_D$ is optionally substituted $C_1$-$C_6$ alkyl, optionally substituted $C_1$-$C_6$ heteroalkyl, optionally substituted $C_2$-$C_6$ alkenyl, optionally substituted $C_2$-$C_6$ heteroalkenyl, optionally substituted $C_2$-$C_6$ alkynyl, optionally substituted $C_2$-$C_6$ heteroalkynyl, optionally substituted cycloalkyl, optionally substituted heterocycloalkyl, optionally substituted aryl, or optionally substituted heteroaryl;

L is optionally substituted $C_1$-$C_6$ alkylene, optionally substituted $C_1$-$C_6$ heteroalkylene, optionally substituted $C_2$-$C_6$ alkenylene, optionally substituted $C_2$-$C_6$ heteroalkenylene, optionally substituted $C_2$-$C_6$ alkynylene, optionally substituted $C_2$-$C_6$ heteroalkynylene, optionally substituted cycloalkylene, optionally substituted heterocycloalkylene, optionally substituted arylene, or optionally substituted heteroarylene;

Z is a chemical moiety that forms a coupling reaction between a reactive substituent present on L and a reactive substituent present within an antibody, antigen-binding fragment thereof, or soluble ligands that binds CD137; and wherein the cytotoxin contains one $R_C$ substituent.

In some embodiments, $R_A$ and $R_B$, together with the oxygen atoms to which they are bound, combine to form:

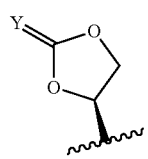

wherein Y is selected from O, S, $NR_E$, and $CR_ER_{E'}$, and $R_E$ and $R_{E'}$ are each independently optionally substituted $C_1$-$C_6$ alkylene-$R_C$, optionally substituted $C_1$-$C_6$ heteroalkylene-$R_C$, optionally substituted $C_2$-$C_6$ alkenylene-$R_C$, optionally substituted $C_2$-$C_6$ heteroalkenylene-$R_C$, optionally substituted $C_2$-$C_6$ alkynylene-$R_C$, optionally substituted $C_2$-$C_6$ heteroalkynylene-$R_C$, optionally substituted cycloalkylene-$R_C$, optionally substituted heterocycloalkylene-$R_C$, optionally substituted arylene-$R_C$, or optionally substituted heteroarylene-$R_C$.

In some embodiments, the cytotoxin is an amatoxin or derivative thereof represented by formula (IVA), wherein $R_1$ is H, OH, $OR_A$, or $OR_C$;

$R_2$ is H, OH, $OR_B$, or $OR_C$;

$R_A$ and $R_B$, together with the oxygen atoms to which they are bound, combine to form:

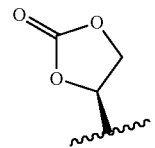 [SMILES: *[C@@H]1COC(=O)O1]

$R_3$ is H or $R_C$;

$R_4$ is H, OH, $OR_C$, $OR_D$, $R_C$, or $R_D$;

$R_5$ is H, OH, $OR_C$, $OR_D$, $R_C$, or $R_D$;

$R_6$ is H, OH, $OR_C$, $OR_D$, $R_C$, or $R_D$;

$R_7$ is H, OH, $OR_C$, $OR_D$, $R_C$, or $R_D$;

$R_8$ is OH, $NH_2$, $OR_C$, or $NHR_C$;

$R_9$ is H or OH; and wherein $R_C$ and $R_D$ are each as defined above. Toxins useful in conjunction with the conjugates described herein include those that contain an amatoxin or derivative thereof represented by formula (IVA), wherein $R_1$ is H, OH, $OR_A$, or $OR_C$;

$R_2$ is H, OH, $OR_B$, or $OR_C$;

$R_A$ and $R_B$, together with the oxygen atoms to which they are bound, combine to form:

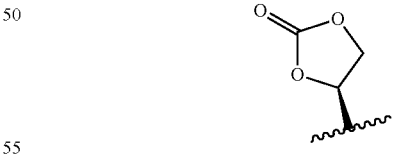

$R_3$ is H or $R_C$;

$R_4$ and $R_5$ are each independently H, OH, $OR_C$, $R_C$, or $OR_D$;

$R_6$ and $R_7$ are each H;

$R_8$ is OH, $NH_2$, $OR_C$, or $NHR_C$;

$R_9$ is H or OH; and wherein $R_C$ is as defined above.

Toxins useful in conjunction with the conjugates described herein include those that contain an amatoxin or derivative thereof represented by formula (IVA), wherein $R_1$ is H, OH, or $OR_A$;

$R_2$ is H, OH, or $OR_B$;

$R_A$ and $R_B$, together with the oxygen atoms to which they are bound, combine to form:

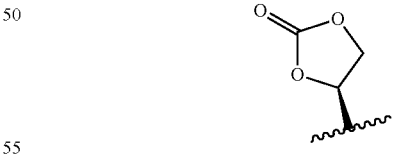

$R_3$, $R_4$, $R_6$, and $R_7$ are each H;

$R_5$ is $OR_C$;

$R_8$ is OH or $NH_2$;

$R_9$ is H or OH; and wherein $R_C$ is as defined above. Such amatoxin conjugates are described, for example, in US Patent Application Publication No. 2016/0002298, the disclosure of which is incorporated herein by reference in its entirety.

Toxins useful in conjunction with the conjugates described herein include those that contain an amatoxin or derivative thereof represented by formula (IVA), wherein $R_1$ and $R_2$ are each independently H or OH;
$R_3$ is $R_C$;
$R_4$, $R_6$, and $R_7$ are each H;
$R_5$ is H, OH, or $OC_1$—$C_6$ alkyl;
$R_8$ is OH or $NH_2$;
$R_9$ is H or OH; and
wherein $R_C$ is as defined above. Such amatoxin conjugates are described, for example, in US Patent Application Publication No. 2014/0294865, the disclosure of which is incorporated herein by reference in its entirety.

Toxins useful in conjunction with the conjugates described herein include those that contain an amatoxin or derivative thereof represented by formula (IVA),
wherein $R_1$ and $R_2$ are each independently H or OH;
$R_3$, $R_6$, and $R_7$ are each H;
$R_4$ and $R_5$ are each independently H, OH, $OR_C$, or $R_C$;
$R_8$ is OH or $NH_2$;
$R_9$ is H or OH; and
wherein $R_C$ is as defined above. Such amatoxin conjugates are described, for example, in US Patent Application Publication No. 2015/0218220, the disclosure of which is incorporated herein by reference in its entirety.

Toxins useful in conjunction with the conjugates described herein include those that contain an amatoxin or derivative thereof represented by formula (IVA),
wherein $R_1$ and $R_2$ are each independently H or OH;
$R_3$, $R_6$, and $R_7$ are each H;
$R_4$ and $R_5$ are each independently H or OH;
$R_8$ is OH, $NH_2$, $OR_C$, or $NHR_C$;
$R_9$ is H or OH; and
wherein $R_C$ is as defined above. Such amatoxin conjugates are described, for example, in U.S. Pat. Nos. 9,233,173 and 9,399,681, the disclosures of each of which are incorporated herein by reference in their entirety.

In some embodiments, antibodies or antigen-binding fragments thereof, described herein are conjugated to an amatoxin, such as α-amanitin, or a variant thereof. For instance, in some embodiments, antibodies or antigen-binding fragments, described herein (e.g., antibodies or antigen-binding fragments that recognize and bind CD137) are conjugated to an α-amanitin compound represented by formula (V):

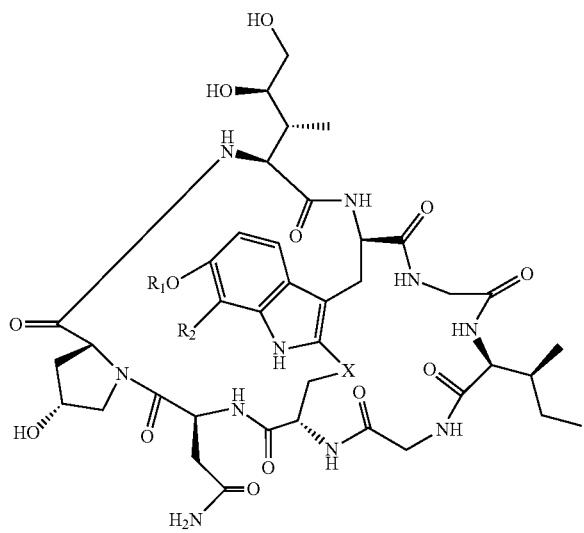

wherein X is S, SO, or $SO_2$; $R_1$ is H or a linker covalently bound to the antibody, antigen-binding fragment thereof or ligand; and $R_2$ is H or a linker covalently bound to the antibody, antigen-binding fragment thereof or ligand; wherein when $R_1$ is H, $R_2$ is the linker, and when $R_2$ is H, $R_1$ is the linker.

In some embodiments, the cytotoxin is an α-amanitin. In some embodiments, the α-amanitin is a compound of formula IV. In some embodiments, the α-amanitin of formula IV is attached to an anti-CD137 antibody via a linker L. The linker L may be attached to the α-amanitin of formula IV at any one of several possible positions (e.g., any of $R^1$-$R^9$). In some embodiments, the linker is attached at position $R^1$. In some embodiments, the linker is attached at position $R^2$. In some embodiments, the linker is attached at position $R^3$. In some embodiments, the linker is attached at position $R^4$. In some embodiments, the linker is attached at position $R^5$. In some embodiments, the linker is attached at position $R^6$. In some embodiments, the linker is attached at position $R^7$. In some embodiments, the linker is attached at position $R^8$. In some embodiments, the linker is attached at position $R^9$. In some embodiments, the linker includes a hydrazine, a disulfide, a thioether or a dipeptide. In some embodiments, the linker includes a dipeptide selected from Val-Ala and Val-Cit. In some embodiments, the linker includes a para-aminobenzyl group (PAB). In some embodiments, the linker includes the moiety PAB-Cit-Val. In some embodiments, the linker includes the moiety PAB-Ala-Val. In some embodiments, the linker includes a —((C=O)(CH$_2$)$_n$— unit, wherein n is an integer from 1-6. In some embodiments, the linker is -PAB-Cit-Val-((C=O)(CH$_2$)$_n$—. In some embodiments, the linker is -PAB-Ala-Val-((C=O)(CH$_2$)$_n$—.

In some embodiments, the cytotoxin is a β-amanitin. In some embodiments, the β-amanitin is a compound of formula IV. In some embodiments, the β-amanitin of formula IV is attached to an anti-CD137 antibody via a linker L. The linker L may be attached to the β-amanitin of formula IV at any one of several possible positions (e.g., any of $R^1$-$R^9$). In some embodiments, the linker is attached at position $R^1$. In some embodiments, the linker is attached at position $R^2$. In some embodiments, the linker is attached at position $R^3$. In some embodiments, the linker is attached at position $R^4$. In some embodiments, the linker is attached at position $R^5$. In some embodiments, the linker is attached at position $R^6$. In some embodiments, the linker is attached at position $R^7$. In some embodiments, the linker is attached at position $R^8$. In some embodiments, the linker is attached at position $R^9$. In some embodiments, the linker includes a hydrazine, a disulfide, a thioether or a dipeptide. In some embodiments, the linker includes a dipeptide selected from Val-Ala and Val-Cit. In some embodiments, the linker includes a para-aminobenzyl group (PAB). In some embodiments, the linker includes the moiety PAB-Cit-Val. In some embodiments, the linker includes the moiety PAB-Ala-Val. In some embodiments, the linker includes a —((C=O)(CH$_2$)$_n$— unit, wherein n is an integer from 1-6. In some embodiments, the linker is -PAB-Cit-Val-((C=O)(CH$_2$)$_n$—. In some embodiments, the linker is -PAB-Ala-Val-((C=O)(CH$_2$)$_n$—.

In some embodiments, the cytotoxin is a γ-amanitin. In some embodiments, the γ-amanitin is a compound of formula IV. In some embodiments, the γ-amanitin of formula IV is attached to an anti-CD137 antibody via a linker L. The linker L may be attached to the γ-amanitin of formula IV at any one of several possible positions (e.g., any of $R^1$-$R^9$). In some embodiments, the linker is attached at position $R^1$. In some embodiments, the linker is attached at position $R^2$. In some embodiments, the linker is attached at position $R^3$. In some embodiments, the linker is attached at position $R^4$. In some embodiments, the linker is attached at position $R^5$. In some embodiments, the linker is attached at position $R^6$. In some embodiments, the linker is attached at position $R^7$. In some embodiments, the linker is attached at position $R^8$. In some embodiments, the linker is attached at position $R^9$. In some embodiments, the linker includes a hydrazine, a disulfide, a thioether or a dipeptide. In some embodiments, the linker includes a dipeptide selected from Val-Ala and Val-Cit. In some embodiments, the linker includes a para-aminobenzyl group (PAB). In some embodiments, the linker includes the moiety PAB-Cit-Val. In some embodiments, the linker includes the moiety PAB-Ala-Val. In some embodiments, the linker includes a —((C=O)(CH$_2$)$_n$— unit, wherein n is an integer from 1-6. In some embodiments, the linker is -PAB-Cit-Val-((C=O)(CH$_2$)$_n$—. In some embodiments, the linker is -PAB-Ala-Val-((C=O)(CH$_2$)$_n$—.

In some embodiments, the cytotoxin is a ε-amanitin. In some embodiments, the ε-amanitin is a compound of formula IV. In some embodiments, the ε-amanitin of formula IV is attached to an anti-CD137 antibody via a linker L. The linker L may be attached to the ε-amanitin of formula IV at any one of several possible positions (e.g., any of $R^1$-$R^9$). In some embodiments, the linker is attached at position $R^1$. In some embodiments, the linker is attached at position $R^2$. In some embodiments, the linker is attached at position $R^3$. In some embodiments, the linker is attached at position $R^4$. In some embodiments, the linker is attached at position $R^5$. In some embodiments, the linker is attached at position $R^6$. In some embodiments, the linker is attached at position $R^7$. In some embodiments, the linker is attached at position $R^8$. In some embodiments, the linker is attached at position $R^9$. In some embodiments, the linker includes a hydrazine, a disulfide, a thioether or a dipeptide. In some embodiments, the linker includes a dipeptide selected from Val-Ala and Val-Cit. In some embodiments, the linker includes a para-aminobenzyl group (PAB). In some embodiments, the linker includes the moiety PAB-Cit-Val. In some embodiments, the linker includes the moiety PAB-Ala-Val. In some embodiments, the linker includes a —((C=O)(CH$_2$)$_n$— unit, wherein n is an integer from 1-6. In some embodiments, the linker is -PAB-Cit-Val-((C=O)(CH$_2$)$_n$—. In some embodiments, the linker is -PAB-Ala-Val-((C=O)(CH$_2$)$_n$—.

In some embodiments, the cytotoxin is an amanin. In some embodiments, the amanin is a compound of formula IV. In some embodiments, the amanin of formula IV is attached to an anti-CD137 antibody via a linker L. The linker L may be attached to the amanin of formula IV at any one of several possible positions (e.g., any of $R^1$-$R^9$). In some embodiments, the linker is attached at position $R^1$. In some embodiments, the linker is attached at position $R^2$. In some embodiments, the linker is attached at position $R^3$. In some embodiments, the linker is attached at position $R^4$. In some embodiments, the linker is attached at position $R^5$. In some embodiments, the linker is attached at position $R^6$. In some embodiments, the linker is attached at position $R^7$. In some embodiments, the linker is attached at position $R^8$. In some embodiments, the linker is attached at position $R^9$. In some embodiments, the linker includes a hydrazine, a disulfide, a thioether or a dipeptide. In some embodiments, the linker includes a dipeptide selected from Val-Ala and Val-Cit. In some embodiments, the linker includes a para-aminobenzyl group (PAB). In some embodiments, the linker includes the moiety PAB-Cit-Val. In some embodiments, the linker includes the moiety PAB-Ala-Val. In some embodiments, the linker includes a —((C=O)(CH$_2$)$_n$-unit, wherein n is an integer from 1-6. In some embodiments, the linker is -PAB-Cit-Val-((C=O)(CH$_2$)$_n$—. In some embodiments, the linker is -PAB-Ala-Val-((C=O)(CH$_2$)$_n$—.

In some embodiments, the cytotoxin is an amaninamide. In some embodiments, the amaninamide is a compound of formula IV. In some embodiments, the amaninamide of formula IV is attached to an anti-CD137 antibody via a linker L. The linker L may be attached to the amaninamide of formula IV at any one of several possible positions (e.g., any of $R^1$-$R^9$). In some embodiments, the linker is attached at position $R^1$. In some embodiments, the linker is attached at position $R^2$. In some embodiments, the linker is attached at position $R^3$. In some embodiments, the linker is attached at position $R^4$. In some embodiments, the linker is attached at position $R^5$. In some embodiments, the linker is attached at position $R^6$. In some embodiments, the linker is attached at position $R^7$. In some embodiments, the linker is attached at position $R^8$. In some embodiments, the linker is attached at position $R^9$. In some embodiments, the linker includes a hydrazine, a disulfide, a thioether or a dipeptide. In some embodiments, the linker includes a dipeptide selected from Val-Ala and Val-Cit. In some embodiments, the linker includes a para-aminobenzyl group (PAB). In some embodiments, the linker includes the moiety PAB-Cit-Val. In some embodiments, the linker includes the moiety PAB-Ala-Val. In some embodiments, the linker includes a —((C=O)(CH$_2$)$_n$— unit, wherein n is an integer from 1-6. In some embodiments, the linker is -PAB-Cit-Val-((C=O)(CH$_2$)$_n$—. In some embodiments, the linker is -PAB-Ala-Val-((C=O)(CH$_2$)$_n$—.

In some embodiments, the cytotoxin is an amanullin. In some embodiments, the amanullin is a compound of formula IV. In some embodiments, the amanullin of formula IV is attached to an anti-CD137 antibody via a linker L. The linker L may be attached to the amanullin of formula IV at any one of several possible positions (e.g., any of $R^1$-$R^9$). In some embodiments, the linker is attached at position $R^1$. In some embodiments, the linker is attached at position $R^2$. In some embodiments, the linker is attached at position $R^3$. In some embodiments, the linker is attached at position $R^4$. In some embodiments, the linker is attached at position $R^5$. In some embodiments, the linker is attached at position $R^6$. In some embodiments, the linker is attached at position $R^7$. In some embodiments, the linker is attached at position $R^8$. In some embodiments, the linker is attached at position $R^9$. In some embodiments, the linker includes a hydrazine, a disulfide, a thioether or a dipeptide. In some embodiments, the linker includes a dipeptide selected from Val-Ala and Val-Cit. In some embodiments, the linker includes a para-aminobenzyl group (PAB). In some embodiments, the linker includes the moiety PAB-Cit-Val. In some embodiments, the linker includes the moiety PAB-Ala-Val. In some embodiments, the linker includes a —((C=O)(CH$_2$)$_n$— unit, wherein n is an integer from 1-6. In some embodiments, the linker is -PAB-Cit-Val-((C=O)(CH$_2$)$_n$—. In some embodiments, the linker is -PAB-Ala-Val-((C=O)(CH$_2$)$_n$—.

In some embodiments, the cytotoxin is an amanullinic acid. In some embodiments, the amanullinic acid is a compound of formula IV. In some embodiments, the amanullinic acid of formula IV is attached to an anti-CD137 antibody via a linker L. The linker L may be attached to the amanullinic acid of formula IV at any one of several possible positions (e.g., any of $R^1$-$R^9$). In some embodiments, the linker is attached at position $R^1$. In some embodiments, the linker is attached at position $R^2$. In some embodiments, the linker is attached at position $R^3$. In some embodiments, the linker is attached at position $R^4$. In some embodiments, the linker is attached at position $R^5$. In some embodiments, the linker is attached at position $R^6$. In some embodiments, the linker is attached at position $R^7$. In some embodiments, the linker is attached at position $R^8$. In some embodiments, the linker is attached at position $R^9$. In some embodiments, the linker includes a hydrazine, a disulfide, a thioether or a dipeptide. In some embodiments, the linker includes a dipeptide selected from Val-Ala and Val-Cit. In some embodiments, the linker includes a para-aminobenzyl group (PAB). In some embodiments, the linker includes the moiety PAB-Cit-Val. In some embodiments, the linker includes the moiety PAB-Ala-Val. In some embodiments, the linker includes a —((C=O)(CH$_2$)$_n$— unit, wherein n is an integer from 1-6. In some embodiments, the linker is -PAB-Cit-Val-((C=O)(CH$_2$)$_n$—. In some embodiments, the linker is -PAB-Ala-Val-((C=O)(CH$_2$)$_n$—.

In some embodiments, the cytotoxin is a proamanullin. In some embodiments, the proamanullin is a compound of formula IV. In some embodiments, the proamanullin of formula IV is attached to an anti-CD137 antibody via a linker L. The linker L may be attached to the proamanullin of formula IV at any one of several possible positions (e.g., any of $R^1$-$R^9$). In some embodiments, the linker is attached at position $R^1$. In some embodiments, the linker is attached at position $R^2$. In some embodiments, the linker is attached at position $R^3$. In some embodiments, the linker is attached at position $R^4$. In some embodiments, the linker is attached at position $R^5$. In some embodiments, the linker is attached at position $R^6$. In some embodiments, the linker is attached at position $R^7$. In some embodiments, the linker is attached at position $R^8$. In some embodiments, the linker is attached at position $R^9$. In some embodiments, the linker includes a hydrazine, a disulfide, a thioether or a dipeptide. In some embodiments, the linker includes a dipeptide selected from Val-Ala and Val-Cit. In some embodiments, the linker includes a para-aminobenzyl group (PAB). In some embodiments, the linker includes the moiety PAB-Cit-Val. In some embodiments, the linker includes the moiety PAB-Ala-Val. In some embodiments, the linker includes a —((C=O)(CH$_2$)$_n$— unit, wherein n is an integer from 1-6. In some embodiments, the linker is -PAB-Cit-Val-((C=O)(CH$_2$)$_n$—. In some embodiments, the linker is -PAB-Ala-Val-((C=O)(CH$_2$)$_n$—.

Antibodies, antigen-binding fragments, and ligands for use with the compositions and methods described herein can be conjugated to an amatoxin, such as α-amanitin or a variant thereof using conjugation techniques known in the art or described herein. For instance, antibodies, antigen-binding fragments thereof, and ligands that recognize and bind CD137 can be conjugated to α-amanitin or a variant thereof, as described in US 2015/0218220, the disclosure of which is incorporated herein by reference as it pertains, for example, to amatoxins, such as α-amanitin and variants thereof, as well as covalent linkers that can be used for covalent conjugation.

Exemplary antibody-drug conjugates and ligand-drug conjugates useful in conjunction with the methods described herein may be formed by the reaction of an antibody, antigen-binding fragment thereof, or ligand with an amatoxin that is conjugated to a linker containing a substituent suitable for reaction with a reactive residue on the antibody, antigen-binding fragment thereof, or ligand. Amatoxins that are conjugated to a linker containing a substituent suitable for reaction with a reactive residue on the antibody, antigen-binding fragment thereof, or ligand include, without limitation, 7'C-(4-(6-(maleimido)hexanoyl)piperazin-1-yl)-amatoxin; 7'C-(4-(6-(maleimido)hexanamido)piperidin-1-yl)-amatoxin; 7'C-(4-(6-(6-(maleimido)hexanamido)hexanoyl) piperazin-1-yl)-amatoxin; 7'C-(4-(4-((maleimido)methyl) cyclohexanecarbonyl)piperazin-1-yl)-amatoxin; 7'C-(4-(6-(4-((maleimido)methyl)cyclohexanecarboxamido) hexanoyl)piperazin-1-yl)-amatoxin; 7'C-(4-(2-(6-(maleimido)hexanamido)ethyl)piperidin-1-yl)-amatoxin; 7'C-(4-(2-(6-(6-(maleimido)hexanamido)hexanamido) ethyl)piperidin-1-yl)-amatoxin; 7'C-(4-(2-(4-((maleimido) methyl)cyclohexanecarboxamido)ethyl)piperidin-1-yl)-amatoxin; 7'C-(4-(2-(6-(4-((maleimido)methyl) cyclohexanecarboxamido)hexanamido)ethyl)piperidin-1-yl)-amatoxin; 7'C-(4-(2-(3-carboxypropanamido)ethyl) piperidin-1-yl)-amatoxin; 7'C-(4-(2-(2-bromoacetamido) ethyl)piperidin-1-yl)-amatoxin; 7'C-(4-(2-(3-(pyridin-2-yldisulfanyl)propanamido)ethyl)piperidin-1-yl)-amatoxin; 7'C-(4-(2-(4-(maleimido)butanamido)ethyl)piperidin-1-yl)-amatoxin; 7'C-(4-(2-(maleimido)acetyl)piperazin-1-yl)-amatoxin; 7'C-(4-(3-(maleimido)propanoyl)piperazin-1-yl)-amatoxin; 7'C-(4-(4-(maleimido)butanoyl)piperazin-1-yl)-amatoxin; 7'C-(4-(2-(6-(4-((maleimido)methyl) cyclohexanecarboxamido)hexanamido)ethyl)piperidin-1-yl)-amatoxin; 7'C-(3-((6-(maleimido)hexanamido)methyl) pyrrolidin-1-yl)-amatoxin; 7'C-(3-((6-(6-(maleimido) hexanamido)hexanamido)methyl)pyrrolidin-1-yl)-amatoxin; 7'C-(3-((4-((maleimido)methyl) cyclohexanecarboxamido)methyl)pyrrolidin-1-yl)-amatoxin; 7'C-(3-((6-((4-(maleimido)methyl) cyclohexanecarboxamido)hexanamido)methyl)pyrrolidin-1-yl)-amatoxin; 7'C-(4-(2-(6-(2-(aminooxy)acetamido) hexanamido)ethyl)piperidin-1-yl)-amatoxin; 7'C-(4-(2-(4-(2-(aminooxy)acetamido)butanamido)ethyl)piperidin-1-yl)-amatoxin; 7'C-(4-(4-(2-(aminooxy)acetamido)butanoyl) piperazin-1-yl)-amatoxin; 7'C-(4-(6-(2-(aminooxy) acetamido)hexanoyl)piperazin-1-yl)-amatoxin; 7'C-((4-(6-(maleimido)hexanamido)piperidin-1-yl)methyl)-amatoxin; 7'C-((4-(2-(6-(maleimido)hexanamido)ethyl)piperidin-1-yl) methyl)-amatoxin; 7'C-((4-(6-(maleimido)hexanoyl)piper-azin-1-yl)methyl)-amatoxin; (R)-7'C-((3-((6-(maleimido) hexanamido)methyl)pyrrolidin-1-yl)methyl)-amatoxin; (S)-7'C-((3-((6-(maleimido)hexanamido)methyl)pyrrolidin-1-yl)methyl)-amatoxin; 7'C-((4-(2-(6-(6-(maleimido) hexanamido)hexanamido)ethyl)piperidin-1-yl)methyl)-amatoxin; 7'C-((4-(2-(4-((maleimido)methyl) cyclohexanecarboxamido)ethyl)piperidin-1-yl)methyl)-amatoxin; 7'C-(4-(2-(6-(4-((maleimido)methyl) cyclohexanecarboxamido)hexanamido)ethyl)piperidin-1-yl) methyl)-amatoxin; 7'C-((4-(2-(6-(maleimido)hexanamido) ethyl)piperazin-1-yl)methyl)-amatoxin; 7'C-((4-(2-(6-(6-(maleimido)hexanamido)hexanamido)ethyl)piperazin-1-yl) methyl)-amatoxin; 7'C-((4-(2-(4-((maleimido)methyl) cyclohexanecarboxamido)ethyl)piperazin-1-yl)methyl)-amatoxin; 7'C-((2-(6-(4-((maleimido)methyl) cyclohexanecarboxamido)hexanamido)ethyl)piperazin-1-yl)methyl)-amatoxin; 7'C-((3-((6-(6-(maleimido) hexanamido)hexanamido)-S-methyl)pyrrolidin-1-yl) methyl)-amatoxin; 7'C-((3-((6-(6-(maleimido)hexanamido) hexanamido)-R-methyl)pyrrolidin-1-yl)methyl)-amatoxin; 7'C-((3-((4-((maleimido)methyl)cyclohexanecarboxamido)-S-methyl)pyrrolidin-1-yl)methyl)-amatoxin; 7'C-((3-((4-((maleimido)methyl)cyclohexanecarboxamido)-R-methyl) pyrrolidin-1-yl)methyl)-amatoxin; 7'C-((3-((6-(4-((maleimido)methyl)cyclohexanecarboxamido) hexanamido)methyl)pyrrolidin-1-yl)methyl)-amatoxin; 7'C-((4-(2-(3-carboxypropanamido)ethyl)piperazin-1-yl) methyl)-amatoxin; 7'C-((4-(6-(6-(maleimido)hexanamido) hexanoyl)piperazin-1-yl)methyl)-amatoxin; 7'C-((4-(6-(4-((maleimido)methyl)cyclohexanecarboxamido)hexanoyl) piperazin-1-yl)methyl)-amatoxin; 7'C-(4-(2-(maleimido)

acetyl)piperazin-1-yl)methyl)-amatoxin; 7'C-((4-(3-(maleimido)propanoyl)piperazin-1-yl)methyl)-amatoxin; 7'C-((4-(4-(maleimido)butanoyl)piperazin-1-yl)methyl)-amatoxin; 7'C-((4-(2-(2-(maleimido)acetamido)ethyl)piperidin-1-yl)methyl)-amatoxin; 7'C-((4-(2-(4-(maleimido)butanamido)ethyl)piperidin-1-yl)methyl)-amatoxin; 7'-((4-(2-(6-(4-((maleimido)methyl)cyclohexanecarboxamido)hexanamido)ethyl)piperidin-1-yl)methyl)-amatoxin; 7'C-((3-((6-(maleimido)hexanamido)methyl)azetidin-1-yl)methyl)-amatoxin; 7'C-((3-(2-(6-(maleimido)hexanamido)ethyl)azetidin-1-yl)methyl)-amatoxin; 7'C-((3-((4-((maleimido)methyl)cyclohexanecarboxamido)methyl)azetidin-1-yl)methyl)-amatoxin; 7'C-((2-(4-((maleimido)methyl)cyclohexanecarboxamido)ethyl)azetidin-1 yl)methyl)-amatoxin; 7'C-((2-(6-(4-((maleimido)methyl)cyclohexanecarboxamido)hexanamido)ethyl)azetidin-1-yl)methyl)-amatoxin; 7'C-(((2-(6-(maleimido)-N-methyl hexanamido)ethyl)(methyl)amino)methyl)-amatoxin; 7'C-(((4-(6-(maleimido)-N-methylhexanamido)butyl(methyl)amino)methyl)-amatoxin; 7'C-((2-(2-(6-(maleimido)hexanamido)ethyl)aziridin-1-yl)methyl)-amatoxin; 7'C-((2-(2-(6-(4-((maleimido)methyl)cyclohexanecarboxamido)hexanamido)ethyl)aziridin-1-yl)methyl)-amatoxin; 7'C-((4-(6-(6-(2-(aminooxy)acetamido)hexanamido)hexanoyl)piperazin-1-yl)methyl)-amatoxin; 7'C-((4-(1-(aminooxy)-2-oxo-6,9,12,15-tetraoxa-3-azaheptadecan-17-oyl)piperazin-1-yl)methyl)-amatoxin; 7'C-((4-(2-(2-(aminooxy)acetamido)acetyl)piperazin-1-yl)methyl)-amatoxin; 7'C-((3-(2-(aminooxy)acetamido)propanoyl)piperazin-1-yl)methyl)-amatoxin; 7'C-((4-(4-(2-(aminooxy)acetamido)butanoyl)piperazin-1-yl)methyl)-amatoxin; 7'C-((2-(6-(2-(aminooxy)acetamido)hexanamido)ethyl)piperidin-1-yl)methyl)-amatoxin; 7'C-((4-(2-(2-(2-(aminooxy)acetamido)acetamido)ethyl)piperidin-1-yl)methyl)-amatoxin; 7'C-((2-(6-(2-(aminooxy)acetamido)butanamido)ethyl)piperidin-1-yl)methyl)-amatoxin; 7'C-((4-(20-(aminooxy)-4,19-dioxo-6,9,12,15-tetraoxa-3,18-diazaicosyl)piperidin-1-yl)methyl)-amatoxin; 7'C-(((2-(6-(2-(aminooxy)acetamido)-N-methylhexanamido)ethyl)(methyl)amino)methyl)-amatoxin; 7'C-(((4-(6-(2-(aminooxy)acetamido)-N-methyl hexanamido)butyl)(methyl)amino)methyl)-amatoxin; 7'C-(3-((6-(4-((maleimido)methyl)cyclohexanecarboxamido)hexanamido)methyl)pyrrolidin-1-yl)-S-methyl)-amatoxin; 7'C-((3-((6-(4-((maleimido)methyl)cyclohexanecarboxamido)hexanamido)-R-methyl)pyrrolidin-1-yl)methyl)-amatoxin; 7'C-((4-(2-(2-bromoacetamido)ethyl)piperazin-1-yl)methyl)-amatoxin; 7'C-((4-(2-(2-bromoacetamido)ethyl)piperidin-1-yl)methyl)-amatoxin; 7'C-((4-(2-(3-(pyridine-2-yldisulfanyl)propanamido)ethyl)piperidin-1-yl)methyl)-amatoxin; 6'O-(6-(6-(maleimido)hexanamido)hexyl)-amatoxin; 6'O-(5-(4-((maleimido)methyl)cyclohexanecarboxamido)pentyl)-amatoxin; 6'O-(2-((6-(maleimido)hexyl)oxy)-2-oxoethyl)-amatoxin; 6'O-((6-(maleimido)hexyl)carbamoyl)-amatoxin; 7'C-((4-((maleimido)methyl)cyclohexanecarboxamido)hexyl)carbamoyl)-amatoxin; 6'O-(6-(2-bromoacetamido)hexyl)-amatoxin; 7'C-(4-(6-(azido)hexanamido)piperidin-1-yl)-amatoxin; 7'C-(4-(hex-5-ynoylamino)piperidin-1-yl)-amatoxin; 7'C-(4-(2-(6-(maleimido)hexanamido)ethyl)piperazin-1-yl)-amatoxin; 7'C-(4-(2-(6-(6-(maleimido)hexanamido)hexanamido)ethyl)piperazin-1-yl)-amatoxin; 6'O-(6-(6-(11,12-didehydro-5,6-dihydro-dibenz[b,f]azocin-5-yl)-6-oxohexanamido)hexyl)-amatoxin; 6'O-(6-(hex-5-ynoylamino)hexyl)-amatoxin; 6'O-(6-(2-(aminooxy)acetylamido)hexyl)-amatoxin; 6'O-((6-aminooxy)hexyl)-amatoxin; and 6'O-(6-(2-iodoacetamido)hexyl)-amatoxin. The foregoing linkers, among others useful in conjunction with the compositions and methods described herein, are described, for example, in US Patent Application Publication No. 2015/0218220, the disclosure of which is incorporated herein by reference in its entirety.

Additional cytotoxins that can be conjugated to antibodies, antigen-binding fragments thereof, and ligands that recognize and bind CD137 for use in treatment of GVHD or an autoimmune disease include, without limitation, 5-ethynyluracil, abiraterone, acylfulvene, adecypenol, adozelesin, aldesleukin, altretamine, ambamustine, amidox, amifostine, aminolevulinic acid, amrubicin, amsacrine, anagrelide, anastrozole, andrographolide, angiogenesis inhibitors, antarelix, anti-dorsalizing morphogenetic protein-1, antiandrogen, prostatic carcinoma, antiestrogen, antineoplaston, antisense oligonucleotides, aphidicolin glycinate, apoptosis gene modulators, apoptosis regulators, apurinic acid, asulacrine, atamestane, atrimustine, axinastatin 1, axinastatin 2, axinastatin 3, azasetron, azatoxin, azatyrosine, baccatin III derivatives, balanol, batimastat, BCR/ABL antagonists, benzochlorins, benzoylstaurosporine, beta lactam derivatives, beta-alethine, betaclamycin B, betulinic acid, bFGF inhibitors, bicalutamide, bisantrene, bisaziridinylspermine, bisnafide, bistratene A, bizelesin, breflate, bleomycin A2, bleomycin B2, bropirimine, budotitane, buthionine sulfoximine, calcipotriol, calphostin C, camptothecin derivatives (e.g., 10-hydroxy-camptothecin), capecitabine, carboxamide-amino-triazole, carboxyamidotriazole, carzelesin, casein kinase inhibitors, castanospermine, cecropin B, cetrorelix, chlorins, chloroquinoxaline sulfonamide, cicaprost, cis-porphyrin, cladribine, clomifene and analogues thereof, clotrimazole, collismycin A, collismycin B, combretastatin A4, combretastatin analogues, conagenin, crambescidin 816, crisnatol, cryptophycin 8, cryptophycin A derivatives, curacin A, cyclopentanthraquinones, cycloplatam, cypemycin, cytarabine ocfosfate, cytolytic factor, cytostatin, dacliximab, decitabine, dehydrodidemnin B, 2'deoxycoformycin (DCF), deslorelin, dexifosfamide, dexrazoxane, dexverapamil, diaziquone, didemnin B, didox, diethylnorspermine, dihydro-5-azacytidine, dihydrotaxol, dioxamycin, diphenyl spiromustine, discodermolide, docosanol, dolasetron, doxifluridine, droloxifene, dronabinol, duocarmycin SA, ebselen, ecomustine, edelfosine, edrecolomab, eflornithine, elemene, emitefur, epothilones, epithilones, epristeride, estramustine and analogues thereof, etoposide, etoposide 4'-phosphate (also referred to as etopofos), exemestane, fadrozole, fazarabine, fenretinide, filgrastim, finasteride, flavopiridol, flezelastine, fluasterone, fludarabine, fluorodaunorunicin hydrochloride, forfenimex, formestane, fostriecin, fotemustine, gadolinium texaphyrin, gallium nitrate, galocitabine, ganirelix, gelatinase inhibitors, gemcitabine, glutathione inhibitors, hepsulfam, homoharringtonine (HHT), hypericin, ibandronic acid, idoxifene, idramantone, ilmofosine, ilomastat, imidazoacridones, imiquimod, immunostimulant peptides, iobenguane, iododoxorubicin, ipomeanol, irinotecan, iroplact, irsogladine, isobengazole, jasplakinolide, kahalalide F, lamellarin-N triacetate, lanreotide, leinamycin, lenograstim, lentinan sulfate, leptolstatin, letrozole, lipophilic platinum compounds, lissoclinamide 7, lobaplatin, lometrexol, lonidamine, losoxantrone, loxoribine, lurtotecan, lutetium texaphyrin, lysofylline, masoprocol, maspin, matrix metalloproteinase inhibitors, menogaril, rnerbarone, meterelin, methioninase, metoclopramide, MIF inhibitor, ifepristone, miltefosine, mirimostim, mithracin, mitoguazone, mitolactol, mitomycin and analogues thereof, mitonafide, mitoxantrone, mofarotene, molgramostim, mycaperoxide B, myriaporone, N-acetyldinaline, N-substituted benzamides, nafarelin, nagrestip, napavin, naphterpin, nartograstim, nedaplatin, nemorubicin, neridronic acid, nilutamide, nisamycin, nitrullyn, octreotide, okicenone, onapristone, ondansetron, oracin, ormaplatin, oxaliplatin, oxaunomycin, paclitaxel and analogues thereof, palauamine, palmitoylrhizoxin, pamidronic acid, panaxytriol, panomifene, parabactin, pazelliptine, pegaspargase, peldesine, pentosan polysulfate sodium, pentostatin, pentrozole, perflubron, perfosfamide, phenazinomycin, picibanil, pirarubicin, piritrexim, podophyllotoxin, porfiromycin, purine nucleoside phosphorylase inhibitors, raltitrexed, rhizoxin, rogletimide, rohitukine, rubiginone B1, ruboxyl, safingol, saintopin, sarcophytol A, sargramostim, sobuzoxane, sonermin, sparfosic acid, spicamycin D, spiromustine, stipiamide, sulfinosine, tallimustine, tegafur, temozolomide, teniposide, thaliblastine, thiocoraline, tirapazamine, topotecan, topsentin, triciribine, trimetrexate, veramine, vinorelbine, vinxaltine, vorozole, zeniplatin, and zilascorb, among others.

Linkers for Chemical Conjugation

A variety of linkers can be used to conjugate antibodies, antigen-binding fragments, and ligands described herein (e.g., antibodies, antigen-binding fragments thereof, and soluble ligands that recognize and bind CD137) with a cytotoxic molecule. Suitable linkers include those that may be cleaved, for instance, by enzymatic hydrolysis, photolysis, hydrolysis under acidic conditions, hydrolysis under basic conditions, oxidation, disulfide reduction, nucleophilic cleavage, or organometallic cleavage (see, for example, Leriche et al., Bioorg. Med. Chem., 20:571-582, 2012, the disclosure of which is incorporated herein by reference as it pertains to linkers suitable for covalent conjugation). Examples of linkers useful for the synthesis of drug-antibody and drug-ligand conjugates include those that contain electrophiles, such as Michael acceptors (e.g., maleimides), activated esters, electron-deficient carbonyl compounds, and aldehydes, among others, suitable for reaction with nucleophilic substituents present within antibodies, antigen-binding fragments, and ligands such as amine and thiol moieties. For instance, linkers suitable for the synthesis of drug-antibody and drug-ligand conjugates include, without limitation, succinimidyl 4-(N-maleimidomethyl)-cyclohexane-L-carboxylate (SMCC), N-succinimidyl iodoacetate (SIA), sulfo-SMCC, m-maleimidobenzoyl-N-hydroxysuccinimidyl ester (MBS), sulfo-MBS, and succinimidyl iodoacetate, among others described, for instance, Liu et al., 18:690-697, 1979, the disclosure of which is incorporated herein by reference as it pertains to linkers for chemical conjugation. Additional linkers include the non-cleavable maleimidocaproyl linkers, which are particularly useful for the conjugation of microtubule-disrupting agents such as auristatins, are described by Doronina et al., Bioconjugate Chem. 17:14-24, 2006, the disclosure of which is incorporated herein by reference as it pertains to linkers for chemical conjugation. Additional linkers suitable for the synthesis of drug-antibody and drug-ligand conjugates as described herein include those capable of releasing a cytotoxin by a 1,6-elimination process, such as p-aminobenzyl alcohol (PABC), 6-maleimidohexanoic acid, pH-sensitive carbonates, and other reagents described in Jain et al., Pharm. Res. 32:3526-3540, 2015, the disclosure of which is incorporated herein by reference in its entirety.

Linkers that can be used to conjugate an antibody, antigen-binding fragment thereof, or ligand to a cytotoxic agent include those that are covalently bound to the cytotoxic agent on one end of the linker and, on the other end of the linker, contain a chemical moiety formed from a coupling reaction between a reactive substituent present on the linker and a reactive substituent present within the antibody, antigen-binding fragment thereof, or ligand that binds CD137. Reactive substituents that may be present within an antibody, antigen-binding fragment thereof, or ligand that binds CD137 include, without limitation, hydroxyl moieties of serine, threonine, and tyrosine residues; amino moieties of lysine residues; carboxyl moieties of aspartic acid and glutamic acid residues; and thiol moieties of cysteine residues, as well as propargyl, azido, haloaryl (e.g., fluoroaryl), haloheteroaryl (e.g., fluoroheteroaryl), haloalkyl, and haloheteroalkyl moieties of non-naturally occurring amino acids. Linkers useful in conjunction with the antibody-drug and ligand-conjugates described herein include, without limitation, linkers containing chemical moieties formed by coupling reactions as depicted in Table 1, below. Curved lines designate points of attachment to the antibody, antigen-binding fragment, or ligand and the cytotoxic molecule, respectively.

TABLE 1

Exemplary chemical moieties formed by coupling reactions in the formation of antibody-drug conjugates

| Exemplary Coupling Reaction | Chemical Moiety Formed by Coupling Reactions |
|---|---|
| [3 + 2] Cycloaddition | |
| [3 + 2] Cycloaddition | |

TABLE 1-continued

Exemplary chemical moieties formed by coupling reactions in the formation of antibody-drug conjugates

| Exemplary Coupling Reaction | Chemical Moiety Formed by Coupling Reactions |
|---|---|
| [3 + 2] Cycloaddition, Esterification | 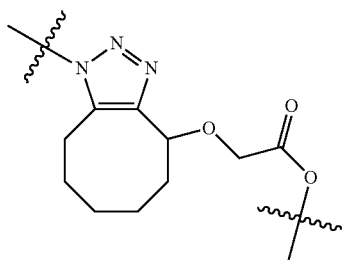 [SMILES: *OC(=O)COC1CCCCCc2c1nnn2*] |
| [3 + 2] Cycloaddition, Esterification | 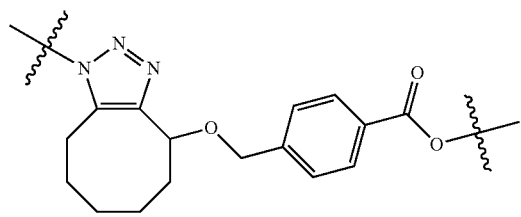 [SMILES: *OC(=O)c1ccc(COC2CCCCCc3c2nnn3*)cc1] |
| [3 + 2] Cycloaddition, Esterification | 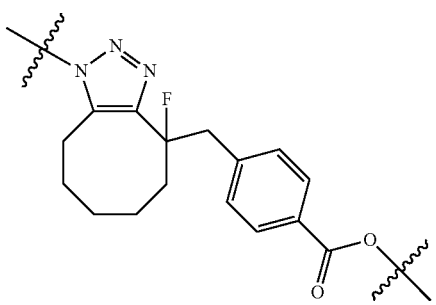 [SMILES: *OC(=O)c1ccc(CC2(F)CCCCCc3c2nnn3*)cc1] |
| [3 + 2] Cycloaddition, Esterification | 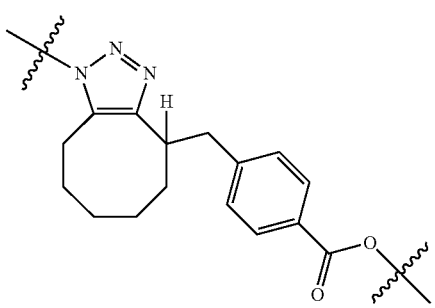 [SMILES: *OC(=O)c1ccc(CC2CCCCCc3c2nnn3*)cc1] |
| [3 + 2] Cycloaddition, Esterification | 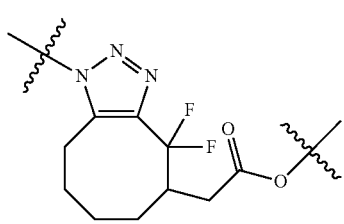 [SMILES: *OC(=O)CC1CCCCc2c(nnn2*)C1(F)F] |

TABLE 1-continued
Exemplary chemical moieties formed by coupling reactions in the formation of antibody-drug conjugates
| Exemplary Coupling Reaction | Chemical Moiety Formed by Coupling Reactions |
|---|---|
| [3 + 2] Cycloaddition, Esterification | 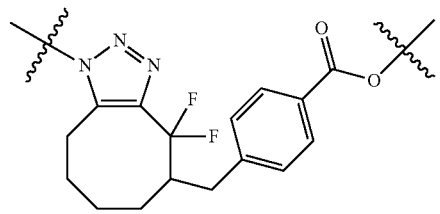 [SMILES: *OC(=O)c1ccc(CC2CCCCc3c(nnn3*)C2(F)F)cc1] |
| [3 + 2] Cycloaddition, Esterification | 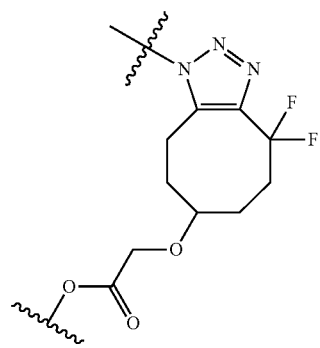 [SMILES: *OC(=O)COC1CCc2c(nnn2*)C(F)(F)CC1] |
| [3 + 2] Cycloaddition, Esterification | 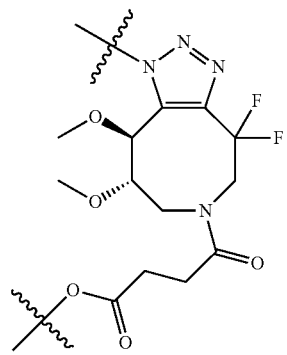 [SMILES: *OC(=O)CCC(=O)N1C[C@H](OC)[C@@H](OC)c2c(nnn2*)C(F)(F)C1] |
| [3 + 2] Cycloaddition, Esterification | 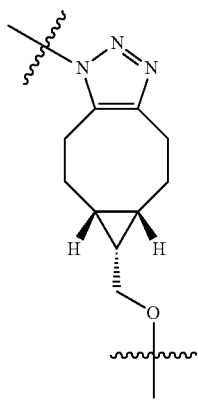 [SMILES: *OC[C@@H]1[C@@H]2CCc3c(nnn3*)CC[C@@H]21] |

TABLE 1-continued

Exemplary chemical moieties formed by coupling reactions in the formation of antibody-drug conjugates

| Exemplary Coupling Reaction | Chemical Moiety Formed by Coupling Reactions |
|---|---|
| [3 + 2] Cycloaddition, Esterification | |
| [3 + 2] Cycloaddition, Esterification | |
| [3 + 2] Cycloaddition, Etherification | |
| [3 + 2] Cycloaddition | |
| Michael addition | |

TABLE 1-continued

Exemplary chemical moieties formed by coupling reactions in the formation of antibody-drug conjugates

| Exemplary Coupling Reaction | Chemical Moiety Formed by Coupling Reactions |
| --- | --- |
| Michael addition | [structure: pyrrolidinone with S, OCH$_3$, N substituents] |
| Imine condensation, Amidation | [structure: C=N-O-CH$_2$-C(=O)-NH-] |
| Imine condensation | [structure: C=N-O-] |
| Disulfide formation | [structure: -S-S-] |
| Thiol alkylation | [structure: -S-CH$_2$-C(=O)-] |
| Condensation, Michael addition | [structure: amidine-CH$_2$CH$_2$-S-succinimide] |

In some embodiments, the ADC comprises an anti-CD137 antibody conjugated to a toxin via linker, wherein the linker includes a hydrazine, a disulfide, a thioether or a dipeptide. In some embodiments, the linker includes a dipeptide selected from Val-Ala and Val-Cit. In some embodiments, the linker includes a para-aminobenzyl group (PAB). In some embodiments, the linker includes the moiety PAB-Cit-Val. In some embodiments, the linker includes the moiety PAB-Ala-Val. In some embodiments, the linker includes a —((C═O)(CH$_2$)$_n$— unit, wherein n is an integer from 1-6. In some embodiments, the linker is -PAB-Cit-Val-((C═O)(CH$_2$)$_n$—. In some embodiments, the linker is -PAB-Ala-Val-((C═O)(CH$_2$)$_n$—.

Antibody Pharmacokinetic Profile

In some embodiments, the antibody, antigen-binding fragment thereof, or drug-antibody conjugate has a defined serum half-life. Antibodies, antigen-binding fragments thereof, and conjugates useful in the methods herein include those that have a serum half-life, for example, from 1-24 hours. In some embodiments, the transplant is administered prior, at the same time or after the antibody, antigen-binding fragment thereof, drug-antibody conjugate, when the level of the circulating antibody is at a therapeutically effective level. Pharmacokinetic analysis by measurement of serum levels can be performed by assays known in the art.

Routes of Administration and Dosing

Antibodies, antigen-binding fragments thereof, ADCs, and ligands described herein can be administered to a patient (e.g., a human patient suffering from or at risk for GVHD or an autoimmune disease) in a variety of dosage forms. For instance, antibodies, antigen-binding fragments thereof, ADCs, and ligands described herein can be administered to a patient suffering from or at risk for GVHD in the form of an aqueous solution, such as an aqueous solution containing one or more pharmaceutically acceptable excipients. Suitable pharmaceutically acceptable excipients for use with the compositions and methods described herein include viscosity-modifying agents. The aqueous solution may be sterilized using techniques known in the art.

Pharmaceutical formulations comprising anti-CD137 ADCs as described herein are prepared by mixing such ADC with one or more optional pharmaceutically acceptable carriers (Remington's Pharmaceutical Sciences 16th edition, Osol, A. Ed. (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG).

The antibodies, antigen-binding fragments, ADCs, and ligands described herein may be administered by a variety of routes, such as orally, transdermally, subcutaneously, intranasally, intravenously, intramuscularly, intraocularly, or parenterally. The most suitable route for administration in any given case will depend on the particular antibody, antigen-binding fragment administered, or ADC, the patient, pharmaceutical formulation methods, administration methods (e.g., administration time and administration route), the patient's age, body weight, sex, severity of the diseases being treated, the patient's diet, and the patient's excretion rate.

The effective dose of an antibody, antigen-binding fragment thereof, ADC, or ligand described herein can range, for example from about 0.001 to about 100 mg/kg of body weight per single (e.g., bolus) administration, multiple administrations, or continuous administration, or to achieve an optimal serum concentration (e.g., a serum concentration of 0.0001-5000 µg/mL) of the antibody, antigen-binding fragment thereof, ADC, or soluble ligand. The dose may be administered one or more times (e.g., 2-10 times) per day, week, or month to a subject (e.g., a human) suffering from or at risk for GVHD or an autoimmune disease. The antibody, antigen-binding fragment thereof, ADC, or ligand can be administered in an amount sufficient to reduce the quantity of host-reactive T cells, for example, by 10%, 20%, 30%, 40%, 50%, 60%, 70%, 80%, 90%, 95%, or more prior to hematopoietic stem cell transplant.

Methods of Treatment

The compositions and methods described herein may be used to deplete activated T cells that are associated with graft failure and autoimmune diseases in order to achieve transplant tolerance. The compositions and methods described herein are particularly useful for preventing and treating GVHD and autoimmune diseases. The methods and compositions disclosed herein are also useful in reducing the risk of transplant failure in a human patient receiving an allogenic transplant. The preferred subject is human. The amount of antibody, antibody-drug conjugate, or ligand-drug conjugate administered should be sufficient to deplete cells, e.g., activated T cells, that promote GVHD or autoimmune disease. The determination of a therapeutically effective dose is within the capability of practitioners in this art, however, as an example, in embodiments of the method described herein utilizing systemic administration of an antibody for the treatment of GHVD or autoimmune disease, an effective human dose will be in the range of 0.1-150 mg/kg (e.g., 5 mg/kg, 10 mg/kg, 25 mg/kg, 50 mg/kg, 75 mg/kg, 100 mg/kg, 150 mg/kg etc.). The route of administration may affect the recommended dose. Repeated systemic doses are contemplated in order to maintain an effective level, e.g., to attenuate or inhibit GVHD or autoimmune disease, depending on the mode of administration adopted.

The antibody, antibody-drug conjugate, or ligand-drug conjugate can be administered to the human patient in need prior to, concomitantly with, or after transplantation of cells or a solid organ to the patient. In one embodiment, an anti-CD137 ADC is administered to the human patient in need thereof prior to (e.g., 3 days before, 2 days before, 12 hours before) transplantation of cells or a solid organ. In one embodiment, an anti-CD137 ADC is administered to the human patient in need thereof after (e.g., 1 days after, 2 days after, 3 days after, or 4 days after) transplantation of cells or a solid organ. A single dose of an anti-CD137 ADC may be administered to the human patient either prior to, concomitantly with, or after transplantation of cells or an organ, where such single dose is sufficient to treat or prevent GVHD or graft failure.

Anti-CD137 ADCs may be used as an alternative to traditional agents (e.g., chemotherapy and/or radiation) used to promote acceptance of a transplant, including an allogeneic transplant. Traditional agents generally reduce a patient's immune response in order to promote engraftment and acceptance of the transplanted cells or organ. The methods and compositions described herein provide a more selective therapy that allows much of the patient's immune system to remain intact, while targeting and depleting CD137 expressing activated T cells. Thus, the ability of anti-CD137 ADCs disclosed herein to selectively deplete activated T cells provides an advantageous therapy over traditional therapy in the context of transplantation given that, in particular, allo-activated immune cells can be targeted and depleted in order to achieve successful transplantation of cells or a solid organ.

The methods and compositions disclosed herein may be used to prevent or treat graft failure. Graft failure or graft rejection, including failure after allogeneic hematopoietic stem cell transplantation, may be manifested generally as either lack of initial engraftment of donor cells, or loss of donor cells after initial engraftment (for review see Mattsson et al. (2008) Biol Blood Marrow Transplant. 14(Suppl 1): 165-170). Compositions and methods disclosed herein may be used to deplete CD137 expressing activated T cells in a graft or transplantation scenario where graft failure is of concern, e.g., where the human patient is at risk of developing graft failure following transplantation of a solid organ or cells, particularly where the transplanted cells or organ is allogeneic.

In one embodiment, the anti-CD137 antibody, antibody-drug conjugate, or ligand-drug conjugate is used to deplete CD137 expressing donor cells, e.g., activated T cells expressing CD137, by contacting the cells, graft or solid organ with the anti-CD137 antibody, antibody-drug conjugate, or ligand-drug conjugate prior to transplantation of the cells, graft or organ to a human patient. In one embodiment, the cells, graft or organ are allogeneic.

The risk of GVHD remains high following transplantation with current therapies. The methods and compositions disclosed herein may be used to inhibit graft versus host disease (GVHD) in a human patient. The anti-CD137 ADCs may be used to selectively target activated T cells in a patient who will be receiving a transplant, such as a stem cell transplant. Anti-CD137 ADCs, as described herein, may also be used to reduce the risk of GVHD by targeting and depleting CD137 positive cells in a human patient who is going to be or has already received a transplant, such as but not limited to, an HSC transplant. In certain embodiments, the compositions and methods disclosed herein are for treating GVHD prior to appearance of symptoms of GVHD in a patient following a transplantation therapy, e.g., allogeneic HSCs.

The methods described herein are also useful for preventing host versus graft (HvG) reactions. An anti-CD137-ADC can also be used as an immunosuppressant to prevent host versus graft (HvG) reactions thereby preventing or reducing the risk of allogeneic graft failure. Use of an anti-CD137 ADC in a patient at risk for a HvG reaction would enable engraftment of donor cells with a greater degree of HLA-mismatch. Additional uses include tolerance induction in solid organ transplant, where host versus graft reactions are prevented or dampened by the CD137-ADC. These would include solid organ transplants done with or without hematopoietic stem cell transplants, including xeno-transplants where the organ is non-human in origin and/or genetically modified.

In one embodiment, an anti-CD137-ADC is used to prevent graft versus graft (GvG) in the context of allogeneic transplants where two donors are used. Examples include the use of 2 cord blood stem cell donors in adult and pediatric patients. Prevention of GvG would enable more rapid hematopoietic (e.g. neutrophil and platelet) reconstitution post-transplant as both stem cell sources would successfully engraft.

In some embodiments, the transplant is allogeneic. In some embodiments, the transplant is autologous.

In some embodiments, the transplant is a bone marrow transplant, a peripheral blood transplant, or a cord blood transplant.

In some embodiments, the transplant includes hematopoietic cells (e.g., hematopoietic stem cells).

In any of the embodiments described herein, the transplant may be any solid organ or skin transplant. In some embodiments, the transplant is selected from the group consisting of kidney transplant, heart transplant, liver transplant, pancreas transplant, lung transplant, intestine transplant and skin transplant.

The methods described herein are useful for treating multiple sclerosis (MS). MS is a devastating autoimmune inflammatory disease of the central nervous system. It is well accepted that the damage in the central nervous system (CNS) results from an autoimmune attack against (auto) antigens within the myelin sheath. The mechanisms responsible for tissue damage in MS involve the activation of self-reactive T cells, which attack proteins in the myelin sheath. It is common for individuals to experience the first signs between the ages of 15 and 50. Affected individuals encounter bouts of inflammatory demyelination producing the classic course of the disease of exacerbation—remittance.

The methods described herein are also useful for treating human systemic lupus (SLE). SLE, or lupus, is a systemic chronic autoimmune disease characterized by autoantibody production against self-antigens. Autoreactive B cells are driven by self-antigen, including antibodies to double stranded DNA, to nuclear protein antigens and to ribonucleoproteins. The factors that promote the loss of B cell tolerance and drive autoantibody production are unknown. Systemic lupus can affect almost any organ or system of the body. Systemic lupus may include periods in which few, if any, symptoms are evident ("remission") and other times when the disease becomes more active ("flare").

The methods described herein are also useful for treating rheumatoid arthritis (RA). RA is a systemic autoimmune disease which initially attacks the synovium, a connective tissue membrane that lines the cavity between joints and secretes a lubricating fluid. Although the cause of RA is unknown, infectious, genetic, and hormonal factors may contribute to the RA. RA is associated with abnormal immunity, as the joints of patients suffering from RA are severely infiltrated with leukocytes, such as macrophages and dendritic cells, and T and B cells. The disease can occur at any age, but the peak incidence of disease onset is between the ages of 25 and 55. The incidence increases with age. The onset of the disease is usually gradual, with fatigue, morning stiffness lasting more than one hour, diffuse muscular aches, loss of appetite, and weakness. Eventually, joint pain appears, with warmth, swelling, tenderness, and stiffness of the joint after inactivity.

The methods described herein are also useful for treating inflammatory bowel disease (IBD). Manifestations of IBD include ulcerative colitis, Crohn's disease, lymphocytic colitis, and collagenous colitis. IBD is a spontaneously relapsing, immunologically mediated disorder of the gastrointestinal tract, characterized by uncontrolled inflammation and persistent activation of the mucosal immune system. CD4 T cells are believed to play a critical role in the pathogenesis of human IBD, due to their influx into the inflamed mucosa.

The methods described herein are particularly useful for treating psoriasis. Psoriasis is a chronic inflammatory skin disease characterized by red, scaly, raised plaques. Psoriasis is mediated by T cells and associated elevation in cytokine levels leading to increased cell division and aberrant differentiation. Psoriasis is a chronic, recurrent skin condition with varying degrees of severity and is also associated with serious co-morbidities, including psoriatic arthritis, depression, malignancy, metabolic syndrome, cardiovascular morbidity and mortality and autoimmune diseases, such as inflammatory bowel disease (IBD).

The methods described herein are also useful for treating Type 1 diabetes mellitus (Type 1 diabetes). Type 1 diabetes is a metabolic disorder in humans that include juvenile onset patients that are not over-weight relative to their age and height, with rapid onset of the disease at an early age, often before 30, although Type 1 diabetes can occur at any age. Type 1 diabetes is considered to be a disease of autoimmune etiology. CD4 and CD8 T cells have been implicated as causative agents for damage to beta cells (insulin producing cells).

The methods described herein are also useful for treating other autoimmune diseases including, but not limited to, acute disseminated encephalomyelitis (ADEM), Addison's disease, alopecia universalis, ankylosing spondylitisis, antiphospholipid antibody syndrome (APS), aplastic anemia, autoimmune hemolytic anemia, autoimmune hepatitis, autoimmune inner ear disease (AIED), autoimmune lymphoproliferative syndrome (ALPS), autoimmune oophoritis, Balo disease, Behcet's disease, bullous pemphigoid, cardiomyopathy, Chagas' disease, chronic fatigue immune dysfunction syndrome (CFIDS), chronic inflammatory demyelinating polyneuropathy, Crohn's disease, cicatrical pemphigoid, coeliac sprue-dermatitis herpetiformis, cold agglutinin disease, CREST syndrome, Degos disease, discoid lupus, dysautonomia, endometriosis, essential mixed cryoglobulinemia, fibromyalgia-fibromyositis, Goodpasture's syndrome, Grave's disease, Guillain-Barre syndrome (GBS), Hashimoto's thyroiditis, Hidradenitis suppurativa, idiopathic and/or acute thrombocytopenic purpura, idiopathic pulmonary fibrosis, IgA neuropathy, interstitial cystitis, juvenile arthritis, Kawasaki's disease, lichen planus, Lyme disease, Meniere disease, mixed connective tissue disease (MCTD), myasthenia gravis, neuromyotonia, opsoclonus myoclonus syndrome (OMS), optic neuritis, Ord's thyroiditis, pemphigus vulgaris, pernicious anemia, polychondritis, polymyositis and dermatomyositis, primary biliary cirrhosis, polyarteritis nodosa, polyglandular syndromes, polymyalgia rheumatica, primary agammaglobulinemia, Raynaud phenomenon, Reiter's syndrome, rheumatic fever, sarcoidosis, scleroderma, Sjögren's syndrome, stiff person syndrome, Takayasu's arteritis, temporal arteritis (also known as "giant cell arteritis"), ulcerative colitis, uveitis, vasculitis, vitiligo, vulvodynia ("vulvar vestibulitis"), and Wegener's granulomatosis.

The compositions and methods described herein can be used to treat a variety of disorders, including, without limitation, a non-malignant hemoglobinopathy (e.g., a hemoglobinopathy selected from the group consisting of sickle cell anemia, thalassemia, Fanconi anemia, and Wiskott-Aldrich syndrome). Additionally or alternatively, the compositions and methods described herein can be used to treat an immunodeficiency, such as a congenital immunodeficiency. Additionally or alternatively, the compositions and methods described herein can be used to treat an acquired immunodeficiency (e.g., an acquired immunodeficiency selected from the group consisting of HIV and AIDS). The compositions and methods described herein can be used to treat a metabolic disorder (e.g., a metabolic disorder selected from the group consisting of glycogen storage diseases, mucopolysaccharidoses, Gaucher's Disease, Hurlers Disease, sphingolipidoses, and metachromatic leukodystrophy). Additionally or alternatively, the compositions and methods described herein can be used to treat a malignancy, such as a hematologic cancer (e.g., leukemia, lymphoma, multiple myeloma and myelodysplastic syndrome), as well as other cancerous conditions, including neuroblastoma.

Additional disorders that can be treated by administration of the compositions and methods described herein include adenosine deaminase deficiency and severe combined immunodeficiency, hyper immunoglobulin M syndrome, Chediak-Higashi disease, hereditary lymphohistiocytosis, osteopetrosis, osteogenesis imperfecta, storage diseases, thalassemia major, systemic sclerosis, systemic lupus erythematosus, multiple sclerosis, and juvenile rheumatoid arthritis.

EXAMPLES

The following examples are put forth so as to provide those of ordinary skill in the art with a description of how the compositions and methods described herein may be used, made, and evaluated, and are intended to be purely exemplary of the invention and are not intended to limit the scope of what the inventors regard as their invention.

Example 1. Administration of an Anti-CD137 Antibody or ADC to a Human Patient in Preparation for Hematopoietic Stem Cell Transplant Therapy According to the methods disclosed herein, a physician of skill in the art can administer to the human patient an antibody, antigen-binding fragment thereof, ADC, or soluble ligand capable of binding CD137, such as an anti-CD137 antibody described herein. The antibody, fragment thereof, ADC, or soluble ligand may be covalently conjugated to a toxin, such as a cytotoxic molecule described herein or known in the art, or an Fc domain. For instance, an anti-CD137 antibody, antigen-binding fragment thereof, ADC, or soluble ligand can be covalently conjugated to a cytotoxin, such as microtubule-binding agent, maytansine, a maytansinoid, an amatoxin, *pseudomonas* exotoxin A, deBouganin, diphtheria toxin, such as α-amanitin, saporin, an auristatin, an anthracycline, a calicheamicin, irinotecan, SN-38, a duocarmycin, a pyrrolobenzodiazepine, a pyrrolobenzodiazepine dimer, an indolinobenzodiazepine, and an indolinobenzodiazepine dimer, or a variant thereof.

This conjugation can be performed using covalent bond-forming techniques described herein or known in the art. The antibody, antigen-binding fragment thereof, or drug-antibody conjugate, or drug-ligand conjugate can subsequently be administered to the patient, for example, by intravenous administration, prior to transplantation of exogenous hematopoietic stem cells (such allogeneic hematopoietic stem cells) to the patient.

The anti-CD137 antibody, antigen-binding fragment thereof, drug-antibody conjugate, or drug-ligand conjugate can be administered in an amount sufficient to reduce the quantity of host-reactive T cells, for example, by 10%, 20%, 30%, 40%, 50%, 60%, 70%, 80%, 90%, 95%, or more prior, at the time of, or after the hematopoietic stem cell transplant therapy. The reduction in donor T cell count can be monitored using conventional techniques known in the art, such as by FACS analysis of cells expressing characteristic hematopoietic cell surface antigens in a blood sample withdrawn from the patient. For instance, a physician of skill in the art can withdraw a blood sample from the patient at various time points and determine the extent of donor CD137+ T cell reduction by conducting a FACS analysis to elucidate the relative concentrations of T cells in the sample using antibodies that bind to donor T cell antigens.

The anti-CD137 antibody, antigen-binding fragment thereof, drug-antibody conjugate, or drug-ligand conjugate can be administered to the patient in an aqueous solution containing one or more pharmaceutically acceptable excipients, such as a viscosity-modifying agent. The aqueous solution may be sterilized using techniques described herein or known in the art. The antibody, antigen-binding fragment thereof, drug-antibody conjugate, or drug-ligand conjugate can be administered to the patient at a dosage of, for example, from 0.001 mg/kg to 100 mg/kg prior to administration of a hematopoietic stem cell graft to the patient. The antibody, antigen-binding fragment thereof, drug-antibody conjugate, or drug-ligand conjugate can be administered to the patient at a time that optimally promotes engraftment of the exogenous hematopoietic stem cells, for instance, from 1 hour to 7 days (e.g., 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, 2 days, 3 days, 4 days, 5 days, 6 days, or 7 days) or more prior to the administration of the exogenous hematopoietic stem cell transplant. For example, the antibody, antigen-binding fragment thereof, drug-antibody conjugate, or drug-ligand conjugate may be administered about 3 days prior to transplant. Alternatively, the antibody, antigen-binding fragment thereof, drug-antibody conjugate, or drug-ligand conjugate can be administered to the patient at a time that optimally promotes engraftment of the exogenous hematopoietic stem cells, for instance, concurrent with the administration of the exogenous hematopoietic stem cell transplant. Additionally, the antibody, antigen-binding fragment thereof, drug-antibody conjugate, or drug-ligand conjugate can be administered to the patient at a time that optimally promotes engraftment of the exogenous hematopoietic stem cells, for instance, from 1 hour to 10 days (e.g., 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, 2 days, 3 days, 4 days, 5 days, 6 days, 7 days, 8 days, 9 days, or 10 days) or more after the administration of the exogenous hematopoietic stem cell transplant. For example, the antibody, antigen-binding fragment thereof, drug-antibody conjugate, or drug-ligand conjugate may be administered about 3 to 4 days after the transplant. The amount of antibody, antigen-binding fragment thereof, drug-antibody conjugate, or drug-ligand conjugate can be quantified, by methods known in the art, in the plasma of patients to determine when the concentration of antibody, antigen-binding fragment thereof, drug-antibody conjugate, or drug-ligand conjugate has reached its maximum.

The patient may then receive an infusion (e.g., an intravenous infusion) of exogenous hematopoietic stem cells, such as from the same physician that administered the antibody or antigen-binding fragment thereof or drug-antibody conjugate or from a different physician. The physician may administer the patient an infusion of autologous, syngeneic, or allogeneic hematopoietic stem cells, for instance, at a dosage of from $1 \times 10^3$ to $1 \times 10^9$ CD34$^+$ cells/kg. The physician may monitor the engraftment of the hematopoietic stem cell transplant, for example, by withdrawing a blood sample from the patient and determining the increase in concentration of hematopoietic stem cells or cells of the hematopoietic lineage (such as megakaryocytes, thrombocytes, platelets, erythrocytes, mast cells, myeloblasts, basophils, neutrophils, eosinophils, microglia, granulocytes, monocytes, osteoclasts, antigen-presenting cells, macrophages, dendritic cells, natural killer cells, T cells, and B cells) following administration of the transplant. This analysis may be conducted, for example, from 1 hour to 6 months, or more, following hematopoietic stem cell transplant therapy (e.g., 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, 2 days, 3 days, 4 days, 5 days, 6 days, 7 days, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, or more). A finding that the concentration of hematopoietic stem cells or cells of the hematopoietic lineage has increased (e.g., by 1%, 2%, 3%, 4%, 5%, 6%, 7%, 8%, 9%, 10%, 20%, 30%, 40%, 50%, 60%, 70%, 80%, 90%, 100%, 200%, 500%, or more) following the transplant therapy relative to the concentration of the corresponding cell type prior to transplant therapy provides one indication that treatment with the anti-CD137 antibody, antigen-binding fragment thereof, drug-antibody conjugate, or drug-ligand conjugate has successfully promoted engraftment of the transplanted hematopoietic stem cell graft.

Example 2. Generating Anti-CD137 Antibodies by Phage Display

An exemplary method for in vitro evolution of anti-CD137 antibodies for use with the compositions and methods described herein is phage display. Phage display libraries can be created by making a designed series of mutations or variations within a coding sequence for the CDRs of an antibody or the analogous regions of an antibody-like scaffold (e.g., the BC, CD, and DE loops of $^{10}$Fn3 domains). The template antibody-encoding sequence into which these mutations are introduced may be, for example, a naive human germline sequence. These mutations can be performed using standard mutagenesis techniques known in the art. Each mutant sequence thus encodes an antibody corresponding to the template save for one or more amino acid variations. Retroviral and phage display vectors can be engineered using standard vector construction techniques known in the art. P3 phage display vectors along with compatible protein expression vectors can be used to generate phage display vectors for antibody diversification.

The mutated DNA provides sequence diversity, and each transformant phage displays one variant of the initial template amino acid sequence encoded by the DNA, leading to a phage population (library) displaying a vast number of different but structurally related amino acid sequences. Due to the well-defined structure of antibody hypervariable regions, the amino acid variations introduced in a phage display screen are expected to alter the binding properties of the binding peptide or domain without significantly altering its overall molecular structure.

In a typical screen, a phage library may be contacted with and allowed to bind CD137 or an epitope thereof. To facilitate separation of binders and non-binders, it is convenient to immobilize the target on a solid support. Phage bearing a CD137-binding moiety can form a complex with the target on the solid support, whereas non-binding phage remain in solution and can be washed away with excess buffer. Bound phage can then liberated from the target by changing the buffer to an extreme pH (pH 2 or pH 10), changing the ionic strength of the buffer, adding denaturants, or other known means.

The recovered phage can then be amplified through infection of bacterial cells, and the screening process can be repeated with the new pool that is now depleted in non-binding antibodies and enriched for antibodies that bind CD137. The recovery of even a few binding phage is sufficient to amplify the phage for a subsequent iteration of screening. After a few rounds of selection, the gene sequences encoding the antibodies or antigen-binding fragments thereof derived from selected phage clones in the binding pool are determined by conventional methods, thus revealing the peptide sequence that imparts binding affinity of the phage to the target. During the panning process, the sequence diversity of the population diminishes with each round of selection until desirable peptide-binding antibodies remain. The sequences may converge on a small number of related antibodies or antigen-binding fragments thereof. An increase in the number of phage recovered at each round of selection is an indication that convergence of the library has occurred in a screen.

Example 3. Producing Humanized Anti-CD137 Antibodies

Non-human antibodies that bind CD137 can be humanized, for instance, according to the following procedure. Consensus human antibody heavy chain and light chain sequences are known in the art (see e.g., the "VBASE" human germline sequence database; Kabat et al. Sequences of Proteins of Immunological Interest, Fifth Edition, U.S. Department of Health and Human Services, NIH Publication No. 91-3242, 1991; Tomlinson et al., J. Mol. Biol. 227:776-798, 1992; and Cox et al. Eur. J. Immunol. 24:827-836, 1994, the disclosures of each of which are incorporated herein by reference as they pertain to consensus human antibody heavy chain and light chain sequences. Using established procedures, one of skill in the art can identify the variable domain framework residues and CDRs of a consensus antibody sequence (e.g., by sequence alignment). One can substitute one or more CDRs of the heavy chain and/or light chain variable domains of consensus human antibody with one or more corresponding CDRs of a non-human antibody that binds CD137 in order to produce a humanized antibody. This CDR exchange can be performed using gene editing techniques described herein or known in the art.

One example of a variable domain of a consensus human antibody contains the heavy chain variable domain EVQLVESGGGLVQPGGSLRLSCAASGFTFSDYAM-SWVRQAPGKGLEWVAVISENGSDTYYAD SVKGR-FTISRDDSKNTLYLQMNSLRAEDTAVYYCARDRG-GAVSYFDVWGQGTLVTVSS (SEQ ID NO: 21) and the light chain variable domain DIQMTQSPSSLSAS-VGDRVTITCRASQDVSSYLAWYQQKPGKAPKLLI-YAASSLESGVPSRFSG SGSGTDFTLTISSLQPEDFA-TYYCQQYNSLPYTFGQGTKVEIKRT (SEQ ID NO: 22), identified in U.S. Pat. No. 6,054,297, the disclosure of which is incorporated herein by reference as it pertains to human antibody consensus sequences. The CDRs in the above sequences are shown in bold.

To produce humanized antibodies, one can recombinantly express a polynucleotide encoding the above consensus sequence in which one or more variable region CDRs have been replaced with one or more variable region CDR sequences of a non-human antibody that binds CD137. As the affinity of the antibody for CD137 is determined primarily by the CDR sequences, the resulting humanized antibody is expected to exhibit an affinity for CD137 that is about the same as that of the non-human antibody from which the humanized antibody was derived. Methods of determining the affinity of an antibody for a target antigen include, for instance, ELISA-based techniques described herein and known in the art, as well as surface plasmon resonance, fluorescence anisotropy, and isothermal titration calorimetry, among others.

Example 4. Administration of an Anti-CD137 Antibody or ADC to a Human Patient at Risk for or Suffering from GVHD According to the methods disclosed herein, a physician of skill in the art can administer to the human patient an antibody, antigen-binding fragment thereof, ADC, or soluble ligand capable of binding CD137, such as an anti-CD137 antibody or ADC described herein. The antibody, fragment thereof, ADC, or soluble ligand may be covalently conjugated to a toxin, such as a cytotoxic molecule described herein or known in the art, or an Fc domain. For instance, an anti-CD137 antibody, antigen-binding fragment thereof, or soluble ligand can be covalently conjugated to a cytotoxin, such as a microtubule-binding agent, maytansine, a maytansinoid, an amatoxin, *pseudomonas* exotoxin A, deBouganin, diphtheria toxin, such as α-amanitin, saporin, an auristatin, an anthracycline, a calicheamicin, irinotecan, SN-38, a duocarmycin, a pyrrolobenzodiazepine, a pyrrolobenzodiazepine dimer, an indolinobenzodiazepine, and an indolinobenzodiazepine dimer, or a variant thereof.

This conjugation can be performed using covalent bond-forming techniques described herein or known in the art. The antibody, antigen-binding fragment thereof, or drug-antibody conjugate, or drug-ligand conjugate can subsequently be administered by intravenous administration, for example, to a patient at risk for GVHD. The antibody, antigen-binding fragment thereof, or drug-antibody conjugate, or drug-ligand conjugate can subsequently be administered by intravenous administration, for example, to a patient suffering from GVHD. For example, the antibody, antigen-binding fragment thereof, or drug-antibody conjugate, or drug-ligand conjugate can be administered to the patient prior, at the time of, or after the transplantation of exogenous hematopoietic stem cells (such as allogeneic hematopoietic stem cells).

The anti-CD137 antibody, antigen-binding fragment thereof, drug-antibody conjugate, or drug-ligand conjugate can be administered in an amount sufficient to reduce the quantity of host-reactive T cells, for example, by 10%, 20%, 30%, 40%, 50%, 60%, 70%, 80%, 90%, 95%, or more following hematopoietic stem cell transplant therapy. The reduction in donor T cell count can be monitored using conventional techniques known in the art, such as by FACS analysis of cells expressing characteristic hematopoietic cell surface antigens in a blood sample withdrawn from the patient. For instance, a physician of skill in the art can withdraw a blood sample from the patient at various time points and determine the extent of donor CD137+ T cell reduction by conducting a FACS analysis to elucidate the relative concentrations of T cells in the sample using antibodies that bind to donor T cell antigens.

The anti-CD137 antibody, antigen-binding fragment thereof, drug-antibody conjugate, or drug-ligand conjugate can be administered to the patient in an aqueous solution containing one or more pharmaceutically acceptable excipients, such as a viscosity-modifying agent. The aqueous solution may be sterilized using techniques described herein or known in the art. The antibody, antigen-binding fragment thereof, drug-antibody conjugate, or drug-ligand conjugate can be administered to the patient at a dosage of, for example, from 0.001 mg/kg to 100 mg/kg prior to administration of a hematopoietic stem cell graft to the patient. The antibody, antigen-binding fragment thereof, drug-antibody conjugate, or drug-ligand conjugate can be administered to the patient at a time that optimally promotes prevention and treatment of GVHD, for instance, from 1 hour to 7 days (e.g., 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, 2 days, 3 days, 4 days, 5 days, 6 days, or 7 days) or more prior to the administration of the exogenous hematopoietic stem cell transplant. For example, the antibody, antigen-binding fragment thereof, drug-antibody conjugate, or drug-ligand conjugate may be administered about 3 days prior to transplant. Alternatively, the antibody, antigen-binding fragment thereof, drug-antibody conjugate, or drug-ligand conjugate can be administered to the patient at a time that optimally promotes engraftment of the exogenous hematopoietic stem cells, for instance, concurrent with the administration of the exogenous hematopoietic stem cell transplant. Additionally, the antibody, antigen-binding fragment thereof, drug-antibody conjugate, or drug-ligand conjugate can be administered to the patient at a time that optimally promotes engraftment of the exogenous hematopoietic stem cells, for instance, from 1 hour to 10 days (e.g., 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, 2 days, 3 days, 4 days, 5 days, 6 days, 7 days, 8 days, 9 days, or 10 days) or more after the administration of the exogenous hematopoietic stem cell transplant. For example, the antibody, antigen-binding fragment thereof, drug-antibody conjugate, or drug-ligand conjugate may be administered about 3 to 4 days after the transplant. The amount of antibody, antigen-binding fragment thereof, drug-antibody conjugate, or drug-ligand conjugate can be quantified, by methods known in the art, in the plasma of patients to determine when the concentration of antibody, antigen-binding fragment thereof, drug-antibody conjugate, or drug-ligand conjugate has reached its maximum.

The patient may then receive an infusion (e.g., an intravenous infusion) of exogenous hematopoietic stem cells, such as from the same physician that administered the antibody or antigen-binding fragment thereof or drug-antibody conjugate, or from a different physician. The physician may administer the patient an infusion of autologous or allogeneic hematopoietic stem cells, for instance, at a dosage of from $1 \times 10^3$ to $1 \times 10^9$ CD34$^+$ cells/kg.

A physician of skill in the art can evaluate the clinical manifestations of GVHD after administering to the human patient an antibody, antigen-binding fragment thereof, ADC, or soluble ligand capable of binding CD137, such as an anti-CD137 antibody described herein.

Example 5. Administration of an Anti-CD137 Antibody or ADC to a Human Patient that Develops an Autoimmune Disease as a Result of Hematopoietic Stem Cell Transplantation According to the methods disclosed herein, a physician of skill in the art can administer to the human patient an antibody, antigen-binding fragment thereof, ADC, or soluble ligand capable of binding CD137, such as an anti-CD137 antibody or ADC described herein. The antibody, fragment thereof, or soluble ligand may be covalently conjugated to a toxin, such as a cytotoxic molecule described herein or known in the art, or an Fc domain. For instance, an anti-CD137 antibody, antigen-binding fragment thereof, or soluble ligand can be covalently conjugated to a cytotoxin, such as a microtubule-binding agent, maytansine, a maytansinoid, an amatoxin, *pseudomonas* exotoxin A, deBouganin, diphtheria toxin, such as α-amanitin, saporin, an auristatin, an anthracycline, a calicheamicin, irinotecan, SN-38, a duocarmycin, a pyrrolobenzodiazepine, a pyrrolobenzodiazepine dimer, an indolinobenzodiazepine, and an indolinobenzodiazepine dimer, or a variant thereof.

This conjugation can be performed using covalent bond-forming techniques described herein or known in the art. The antibody, antigen-binding fragment thereof, or drug-antibody conjugate, or drug-ligand conjugate can subsequently be administered by intravenous administration, for example, to a patient at risk for an autoimmune disease (e.g., multiple sclerosis, rheumatoid arthritis, intestinal bowel disease, psoriasis, lupus, and Type 1 diabetes). For example, the antibody, antigen-binding fragment thereof, or drug-antibody conjugate, or drug-ligand conjugate can be administered to the patient suffering from autoimmune disease that develops after the transplantation of exogenous hematopoietic stem cells (such as autologous or allogeneic hematopoietic stem cells).

The anti-CD137 antibody, antigen-binding fragment thereof, drug-antibody conjugate, or drug-ligand conjugate can be administered in an amount sufficient to reduce the quantity of host-reactive lymphocytes, for example, by 10%, 20%, 30%, 40%, 50%, 60%, 70%, 80%, 90%, 95%, or more prior to hematopoietic stem cell transplant therapy. The reduction in donor lymphocyte count can be monitored using conventional techniques known in the art, such as by FACS analysis of cells expressing characteristic hematopoietic cell surface antigens in a blood sample withdrawn from the patient. For instance, a physician of skill in the art can withdraw a blood sample from the patient at various time points and determine the extent of CD137+ T cell reduction by conducting a FACS analysis to elucidate the relative concentrations of T cells in the sample using antibodies that bind to T cell antigens. Efficacy against autoimmune disease can be measured by assays known in the art (e.g., autoantibody responses measurement from serum samples, and T cell proliferation in response to autoantigens).

The anti-CD137 antibody, antigen-binding fragment thereof, drug-antibody conjugate, or drug-ligand conjugate can be administered to the patient in an aqueous solution containing one or more pharmaceutically acceptable excipients, such as a viscosity-modifying agent. The aqueous solution may be sterilized using techniques described herein or known in the art. The antibody, antigen-binding fragment thereof, drug-antibody conjugate, or drug-ligand conjugate can be administered to the patient at a dosage of, for example, from 0.001 mg/kg to 100 mg/kg prior to administration of a hematopoietic stem cell graft to the patient. The antibody, antigen-binding fragment thereof, drug-antibody conjugate, or drug-ligand conjugate can be administered to the patient at a time that optimally promotes prevention and treatment of autoimmune disease, for instance, from 1 hour to 7 days (e.g., 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, 2 days, 3 days, 4 days, 5 days, 6 days, or 7 days) or more prior to the administration of the exogenous hematopoietic stem cell transplant. For example, the antibody, antigen-binding fragment thereof, drug-antibody conjugate, or drug-ligand conjugate may be administered about 3 days prior to transplant. Alternatively, the antibody, antigen-binding fragment thereof, drug-antibody conjugate, or drug-ligand conjugate can be administered to the patient at a time that optimally promotes engraftment of the exogenous hematopoietic stem cells, for instance, concurrent with the administration of the exogenous hematopoietic stem cell transplant. Additionally, the antibody, antigen-binding fragment thereof, drug-antibody conjugate, or drug-ligand conjugate can be administered to the patient at a time that optimally promotes engraftment of the exogenous hematopoietic stem cells, for instance, from 1 hour to 10 days (e.g., 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, 2 days, 3 days, 4 days, 5 days, 6 days, 7 days, 8 days, 9 days, or 10 days) or more after the administration of the exogenous hematopoietic stem cell transplant. For example, the antibody, antigen-binding fragment thereof, drug-antibody conjugate, or drug-ligand conjugate may be administered about 3 to 4 days after the transplant. The amount of antibody, antigen-binding fragment thereof, drug-antibody conjugate, or drug-ligand conjugate can be quantified, by methods known in the art, in the plasma of patients to determine when the concentration of antibody, antigen-binding fragment thereof, drug-antibody conjugate, or drug-ligand conjugate has reached its maximum.

The patient may then receive an infusion (e.g., an intravenous infusion) of exogenous hematopoietic stem cells, such as from the same physician that administered the antibody or antigen-binding fragment thereof or drug-antibody conjugate or from a different physician. The physician may administer the patient an infusion of autologous or allogeneic hematopoietic stem cells, for instance, at a dosage of from $1 \times 10^3$ to $1 \times 10^9$ CD34+ cells/kg.

A physician of skill in the art can evaluate the clinical manifestations of autoimmune disease after administering to the human patient an antibody, antigen-binding fragment thereof, ADC, or soluble ligand capable of binding CD137, such as an anti-CD137 antibody or ADC described herein.

Example 6. Administration of an Anti-CD137 Antibody to a Human Patient at Risk or Suffering from an Autoimmune Disease According to the methods disclosed herein, a physician of skill in the art can administer to the human patient an antibody, antigen-binding fragment thereof, ADC, or soluble ligand capable of binding CD137, such as an anti-CD137 antibody or ADC described herein. The antibody, fragment thereof, or soluble ligand may be covalently conjugated to a toxin, such as a cytotoxic molecule described herein or known in the art, or an Fc domain.

This conjugation can be performed using covalent bond-forming techniques described herein or known in the art. The antibody, antigen-binding fragment thereof, or drug-antibody conjugate, or drug-ligand conjugate can subsequently be administered by intravenous administration, for example, to a patient at risk for autoimmune disease (e.g., multiple sclerosis, rheumatoid arthritis, intestinal bowel disease, psoriasis, lupus, and Type 1 diabetes). The antibody, antigen-binding fragment thereof, or drug-antibody conjugate, or drug-ligand conjugate can subsequently be administered by intravenous administration, for example, to a patient suffering from autoimmune disease (e.g., multiple sclerosis, rheumatoid arthritis, intestinal bowel disease, psoriasis, lupus, and Type 1 diabetes).

The anti-CD137 antibody, antigen-binding fragment thereof, drug-antibody conjugate, or drug-ligand conjugate can be administered in an amount sufficient to reduce the quantity of host-reactive lymphocytes, for example, by 10%, 20%, 30%, 40%, 50%, 60%, 70%, 80%, 90%, 95%, or more. The reduction in donor lymphocyte count can be monitored using conventional techniques known in the art, such as by FACS analysis of cells expressing characteristic hematopoietic cell surface antigens in a blood sample withdrawn from the patient. For instance, a physician of skill in the art can withdraw a blood sample from the patient at various time points and determine the extent of CD137+ T cell reduction by conducting a FACS analysis to elucidate the relative concentrations of T cells in the sample using antibodies that bind to T cell antigens. Efficacy against autoimmune disease can be measured by assays known in the art (e.g., autoantibody responses measurement from serum samples, and T cell proliferation in response to autoantigens).

The anti-CD137 antibody, antigen-binding fragment thereof, drug-antibody conjugate, or drug-ligand conjugate can be administered to the patient in an aqueous solution containing one or more pharmaceutically acceptable excipients, such as a viscosity-modifying agent. The aqueous solution may be sterilized using techniques described herein or known in the art. The antibody, antigen-binding fragment thereof, drug-antibody conjugate, or drug-ligand conjugate can be administered to the patient at a dosage of, for example, from 0.001 mg/kg to 100 mg/kg prior to administration of a hematopoietic stem cell graft to the patient. The antibody, antigen-binding fragment thereof, drug-antibody conjugate, or drug-ligand conjugate can be administered to the patient at a time that optimally promotes prevention and treatment of autoimmune disease. The amount of antibody, antigen-binding fragment thereof, drug-antibody conjugate, or drug-ligand conjugate can be quantified, by methods known in the art, in the plasma of patients to determine when the concentration of antibody, antigen-binding fragment thereof, drug-antibody conjugate, or drug-ligand conjugate has reached its maximum.

A physician of skill in the art can evaluate the clinical manifestations of autoimmune disease after administering to the human patient an antibody, antigen-binding fragment thereof, or soluble ligand capable of binding CD137, such as an anti-CD137 antibody or ADC described herein.

Example 7. In Vitro Cell Line Binding Assay

Jurkat cells (i.e., an immortalized human T lymphocyte cell line) characterized by stable, over-expression of hCD137 were plated at 20,000 cells/well and stained with a titration of primary murine anti-CD137 antibody BBK2 (BBK2-mIgG1) for 4 hours at 4° C. Secondary anti-mouse AF488 stain, at a constant amount, was added for 30 minutes at 4° C. After washing, plates were run on a flow cytometer and binding of BBK2-mIgG1 (and the negative control, i.e., mIgG1) was determined based on geometric mean fluorescence intensity in the AF488 channel. Results from these assays are provided in FIGS. 1A and B.

Figure 1B:
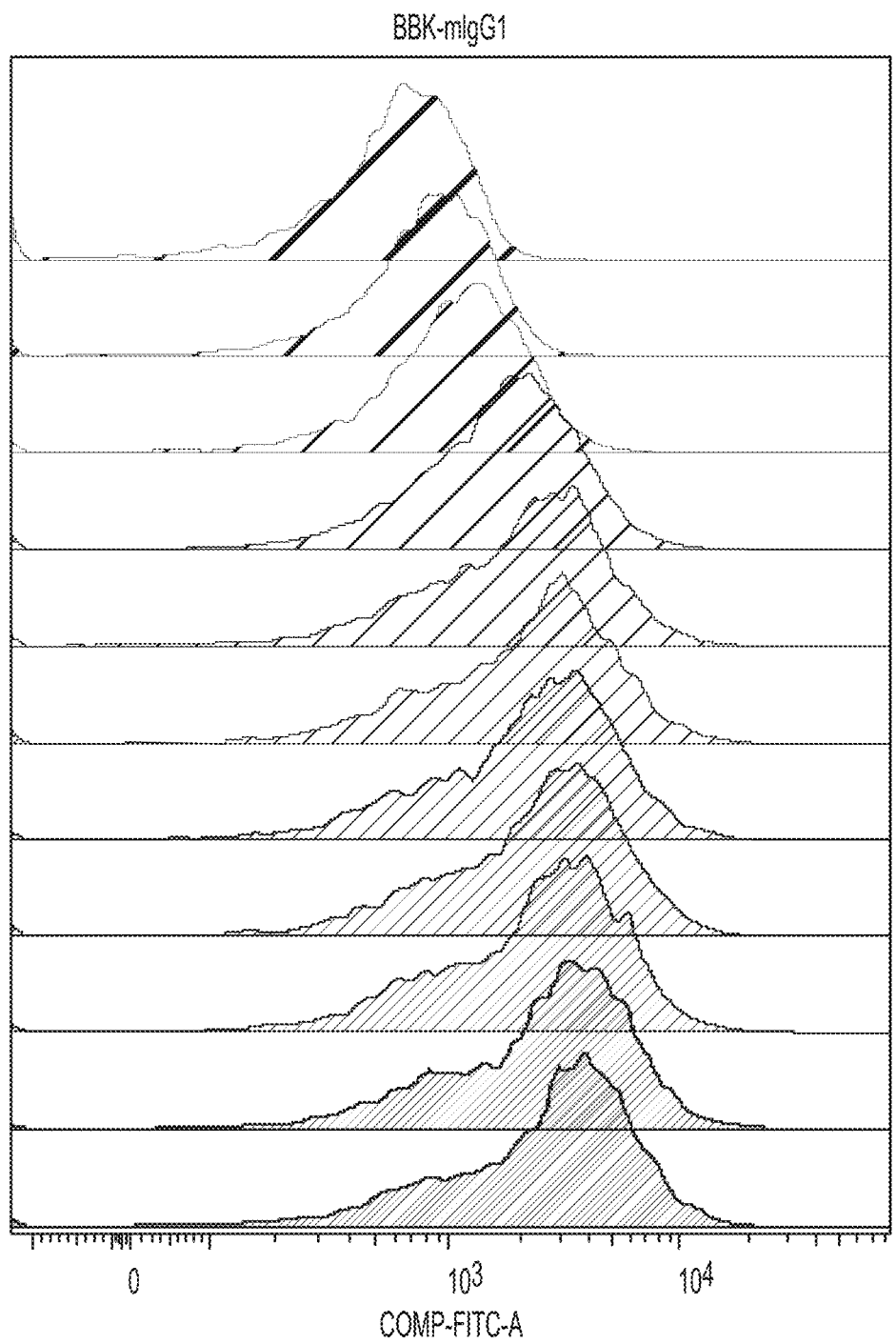

As shown in FIGS. 1A and 1B, the murine BBK2 antibody binds to human T cells (i.e. CD137-expressing Jurkat cells), with an $EC_{50}=35$ pM.

Example 8. In Vitro Analysis of an Anti-CD137-Amanitin Antibody Drug Conjugate (ADC) Using an In Vitro T Cell Killing Assay Cryopreserved negatively-selected primary human T cells were thawed and stimulated with anti-CD3/anti-CD28 beads (Invitrogen) at a bead:cell ratio of 0.5:1. At the start of the assay, 2e4 T cells were seeded per well of a 384 well plate and ADCs were added to the wells at various concentrations between 0.003 nm and 30 nm before being placed in an incubator with 37° C. and 5% $CO_2$. Following 4 days of culture, cells were analyzed by flow cytometry. Cells were stained with a viability marker Live/Dead Yellow (Invitrogen) and run on a volumetric flow cytometer. Numbers of viable, activated cells (FIG. 2A) and viable, non-activated cells (FIG. 2B) were determined by FSC vs SSC. A non-specific human IgG conjugated to amanitin (hIgG-amanitin) served as a negative control. Thus control was compared to two different ADCs: 1) chimeric anti-CD137 antibody BBK2 conjugated to amanitin (CD137-Amanitin); and 2) an ADC including an antibody specific a T-cell antigen conjugated to Amanitin (anti-Tcell-Amanitin). The anti-Tcell-Amanitin ADC served as a positive control as it was expected to bind and kill both activated and non-activated T cells.

Figure 2A:
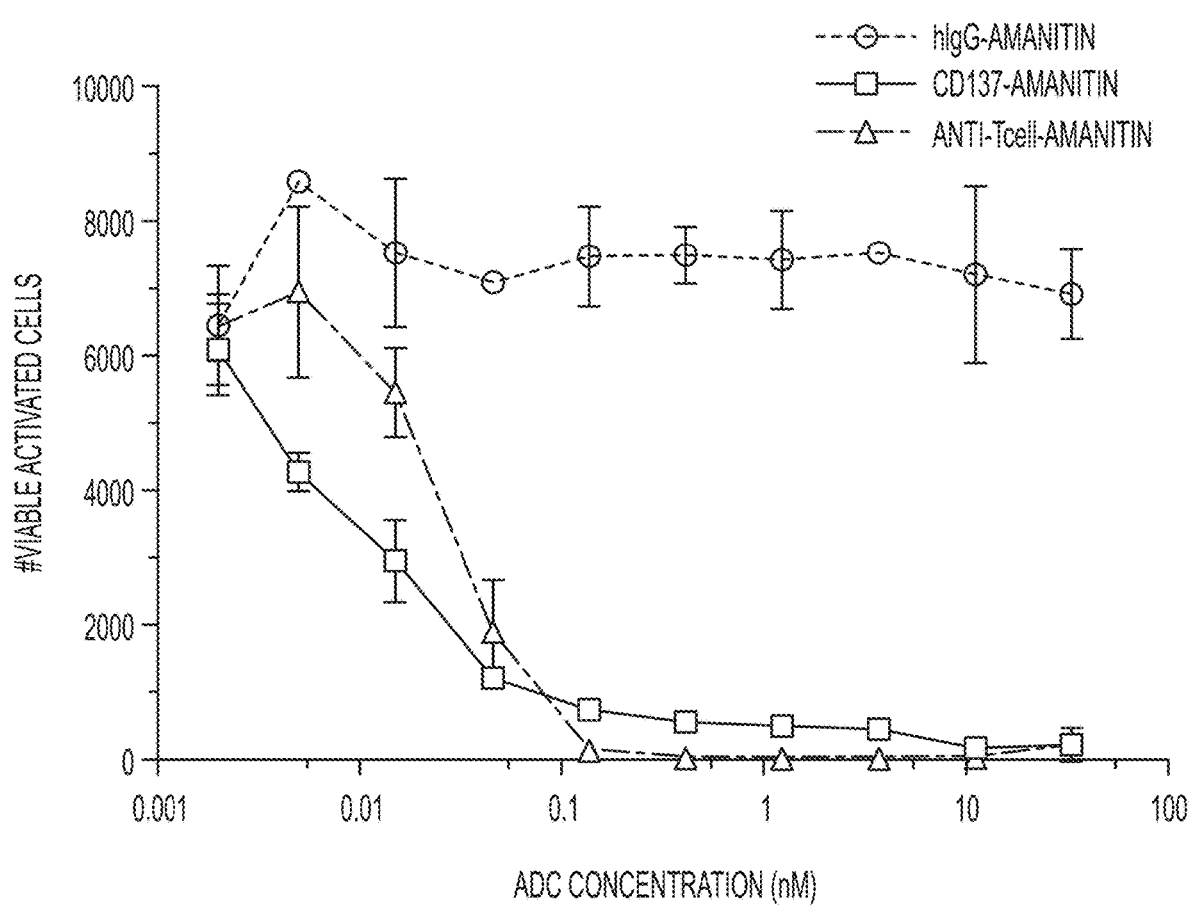
FIGS. 2A and 2B graphically depict results of an in vitro T cell killing assay including an anti-CD137-amanitin ADC (i.e., "CD137-Amanitin") and an anti-T cell specific-amanitin ADC (i.e., "anti-Tcell-Amanitin") in comparison to a negative control (i.e., "hIgG-Amanitin"). The results show the number of viable activated cells (FIG. 2A) or viable non-activated cells (FIG. 2B) of each ADC (y-axis) as a function of ADC concentration (x-axis).
Figure 2B:
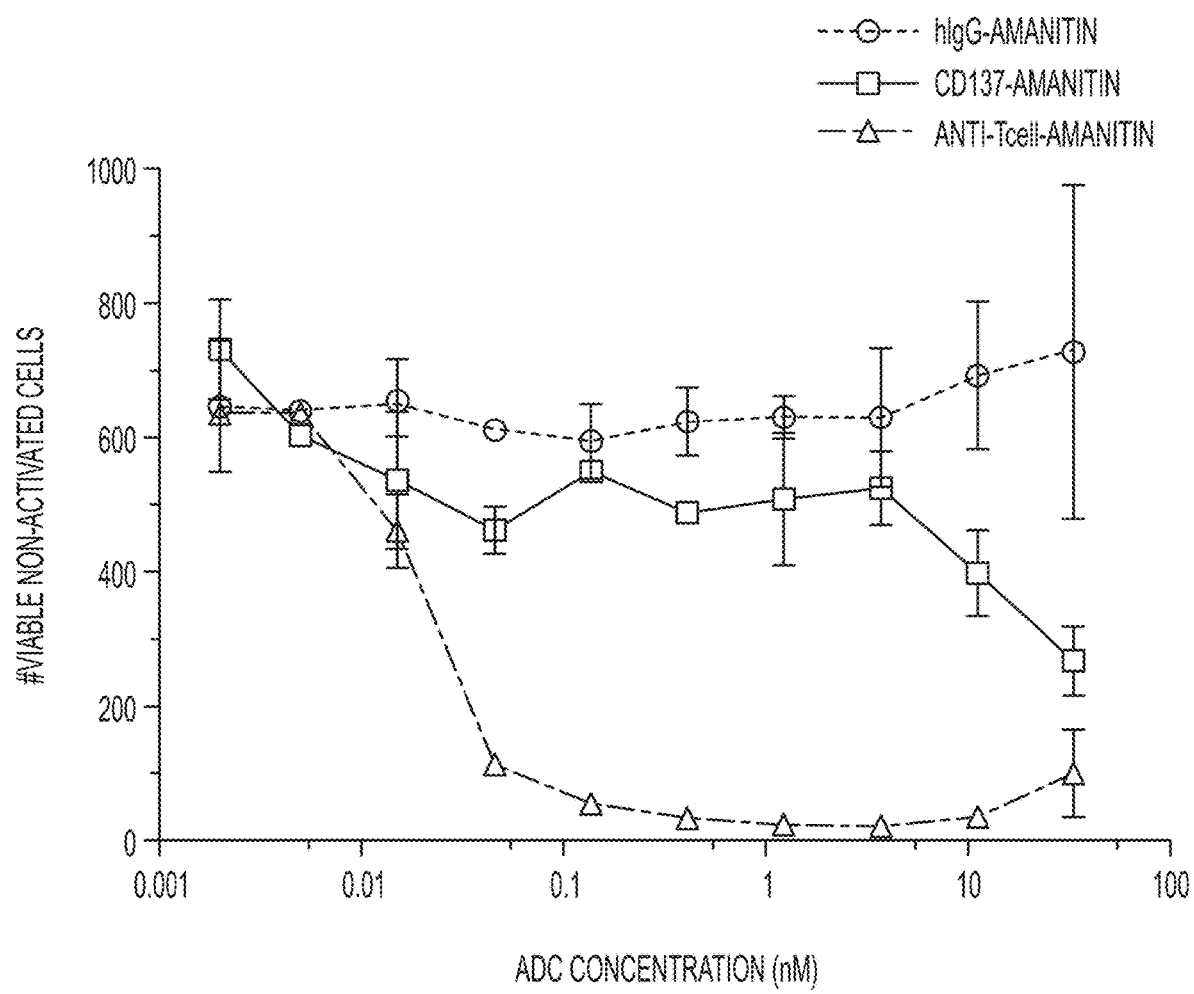

As shown in FIGS. 2A and 2B, the anti-CD137-amanitin ADC (i.e., "CD137-Amanitin) specifically killed activated T cells and did not appreciably kill non-activated (resting, steady-state) T cells. In addition, the positive control (i.e., the "anti-Tcell-Amanitin" ADC), which was an ADC that specifically targeted both activated and non-activated T cells, killed both activated and non-activated T cells.

Example 9. Analysis of the Prevention of GVHD Using a Xeno-GVHD Mouse Model

The ability of an anti-CD137-amanitin ADC to prevent the formation or occurrence of GVHD was assessed in vivo using a xeno-GVHD mouse model. Female, 6-8-week-old NSG mice were irradiated (200 cGy) and transplanted the following day with $6 \times 10^6$ human peripheral blood mononuclear cells (PBMCs) to generate the GVHD mouse model. One day later, animals were dosed (at 3 mg/kg) with an anti-CD137-amanitin ADC (i.e., "CD137-Amanitin") or with various control reagents (i.e., buffer alone ("PBS"), an anti-CD137 antibody ("CD137 Naked"), or an amanitin-based ADC that is not specific to CD137 ("Isotype-Amanitin")). The anti-CD137 antibody used in this example in the ADCs and as a naked antibody was chimeric BBK2.

Animals were followed closely daily after dosing for signs of GVHD and/or decreased body conditions including, but not limited to, hunched posture, ruffled fur, weight loss, and/or limited activity. Animals with severe body condition concerns, or those animals that showed weight loss >20%, were sacrificed and their tissues were analyzed for human cells. Peripheral blood and spleens of mice were stained with a cocktail of antibodies, including hCD45, mCD45, hCD3, and hCD137 antibodies, red blood cell were lysed, and analyzed by flow cytometry. The number of human T cells in the blood were defined as hCD45+CD3+ and normalized to input blood volume. The percent survival as a function of days post-treatment is provided in FIG. 3. The number of human T cells in the peripheral blood as a function of days post-transplant is provided in FIG. 4.

Figure 3:
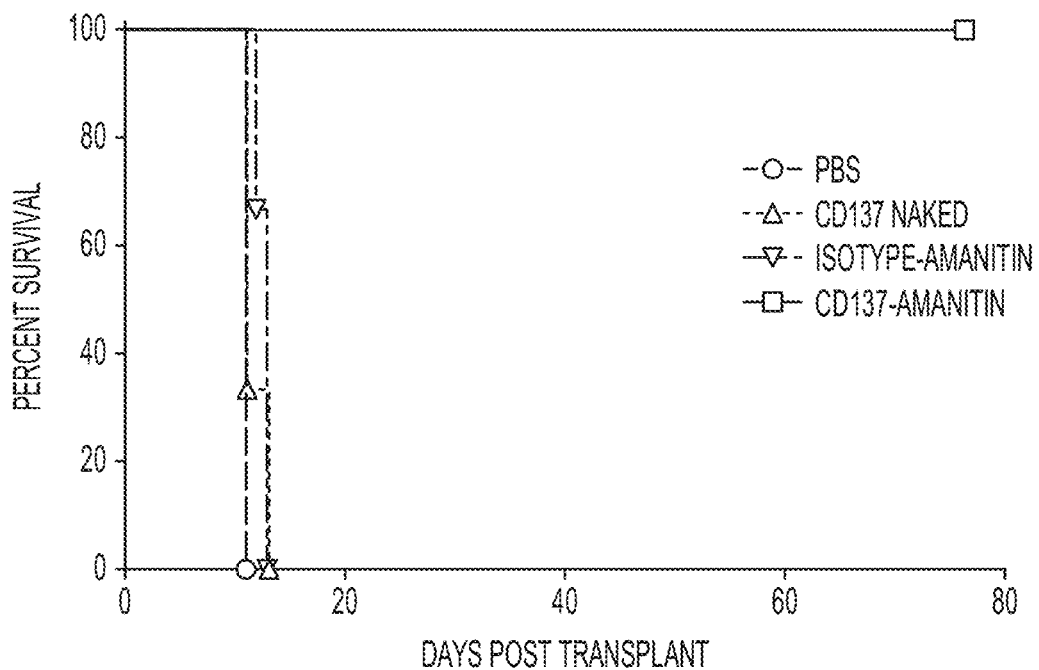
FIG. 3 graphically depicts the results of an in vivo assay comparing the percent survival of mice (y-axis) as a function of days post-transplant (x-axis) for an anti-CD137-amanitin ADC in comparison to controls PBS, an anti-CD137 antibody (naked), and isotype-amanitin in a NSG mouse xeno-GVHD model.
Figure 4:
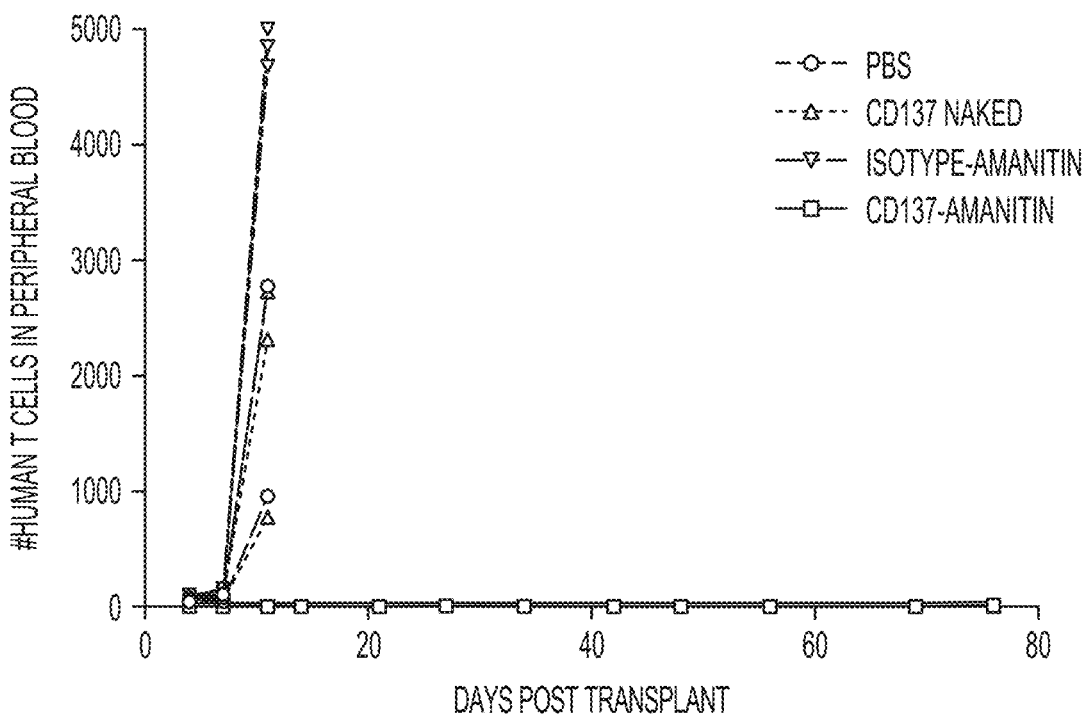
FIG. 4 graphically depicts the results of an in vivo assay comparing the number of human T cells detected in the peripheral blood (y-axis) as a function of days post-transplant (x-axis) for an anti-CD137-amanitin ADC in comparison to controls PBS, an anti-CD137 antibody (naked), and isotype-amanitin in a NSG mouse xeno-GVHD model.

As demonstrated in FIG. 3, the animals treated with a single dose of the anti-CD137-amanitin ADC ("CD137-Amanitin") showed essentially complete prevention of GVHD, even at 80 days post-transplant, while the animals treated with a control (i.e., PBS, an anti-CD137 antibody (naked), and isotype-amanitin) all died within 11 to 13 days post-transplant. These results also indicate that the anti-CD137-amanitin ADC was well-tolerated in all animals and that a single dose of the anti-CD137-amanitin ADC was sufficient to completely prevent GVHD (as opposed to requiring multiple doses). As demonstrated in FIG. 4, no human T cells were detectable in the peripheral blood of mice over a period of at least 70 days after the transplant in anti-CD137-amanitin treated mice, while animals treated with a control were characterized as having human T cells detectable in the peripheral blood of mice several days post-transplant, indicating the development of GVHD in the animals treated with a control.

Figure 5A:
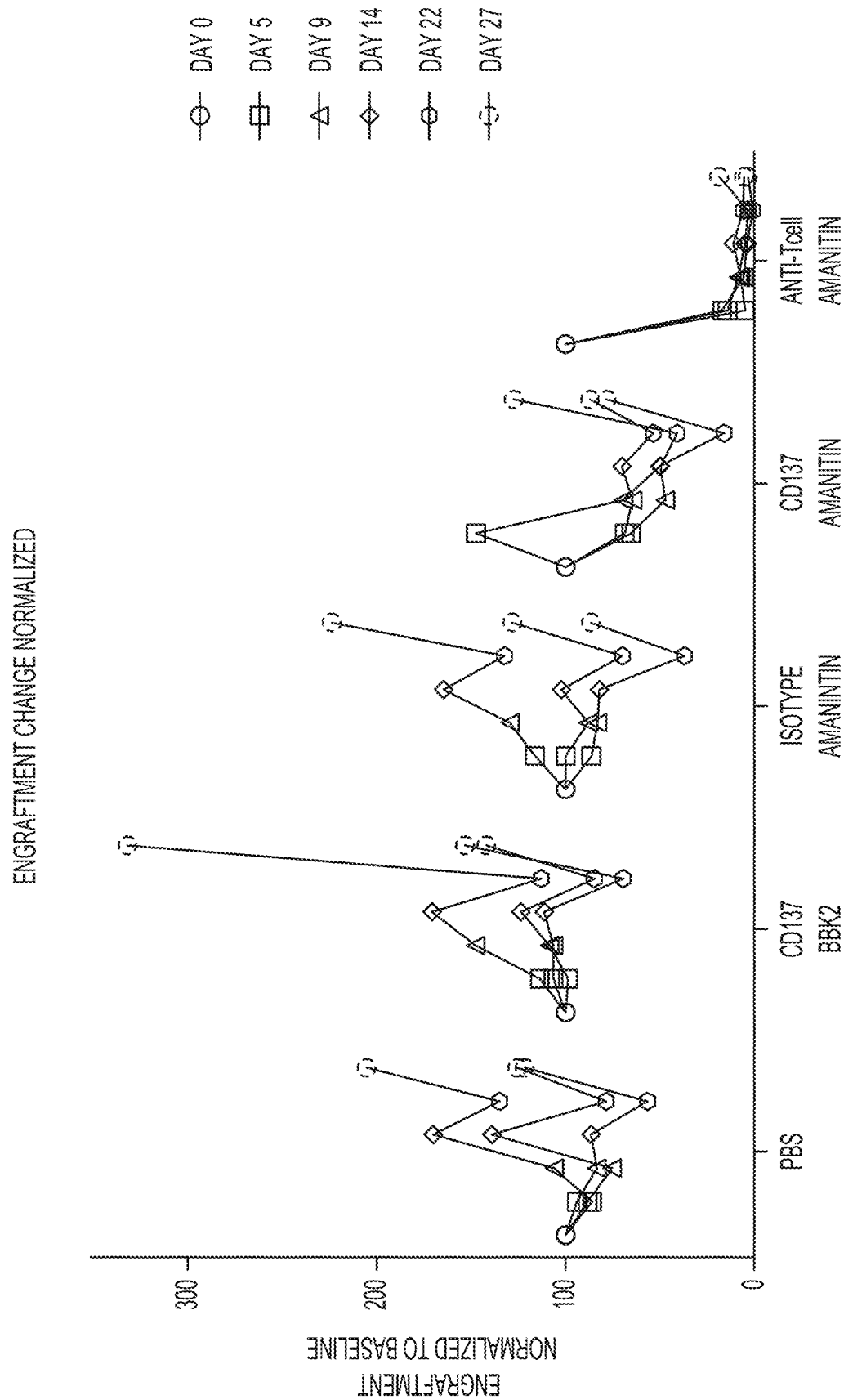
FIGS. 5A and 5B graphically depict the results of in vivo assays for determining engraftment rates (FIG. 5A) and T cell frequency (FIG. 5B) in a humanized NSG-SGM3 mouse model where engraftment and T cell frequency were measured at day 5, day 9, day 14, day 22 and at day 27 post-transplant for an anti-CD137-amanitin ADC in comparison to controls PBS, an anti-CD137-BBK antibody (naked), an isotype-amanitin, and an anti-Tcell-Amanitin ADC in a NSG mouse xeno-GVHD model.
Figure 5B:
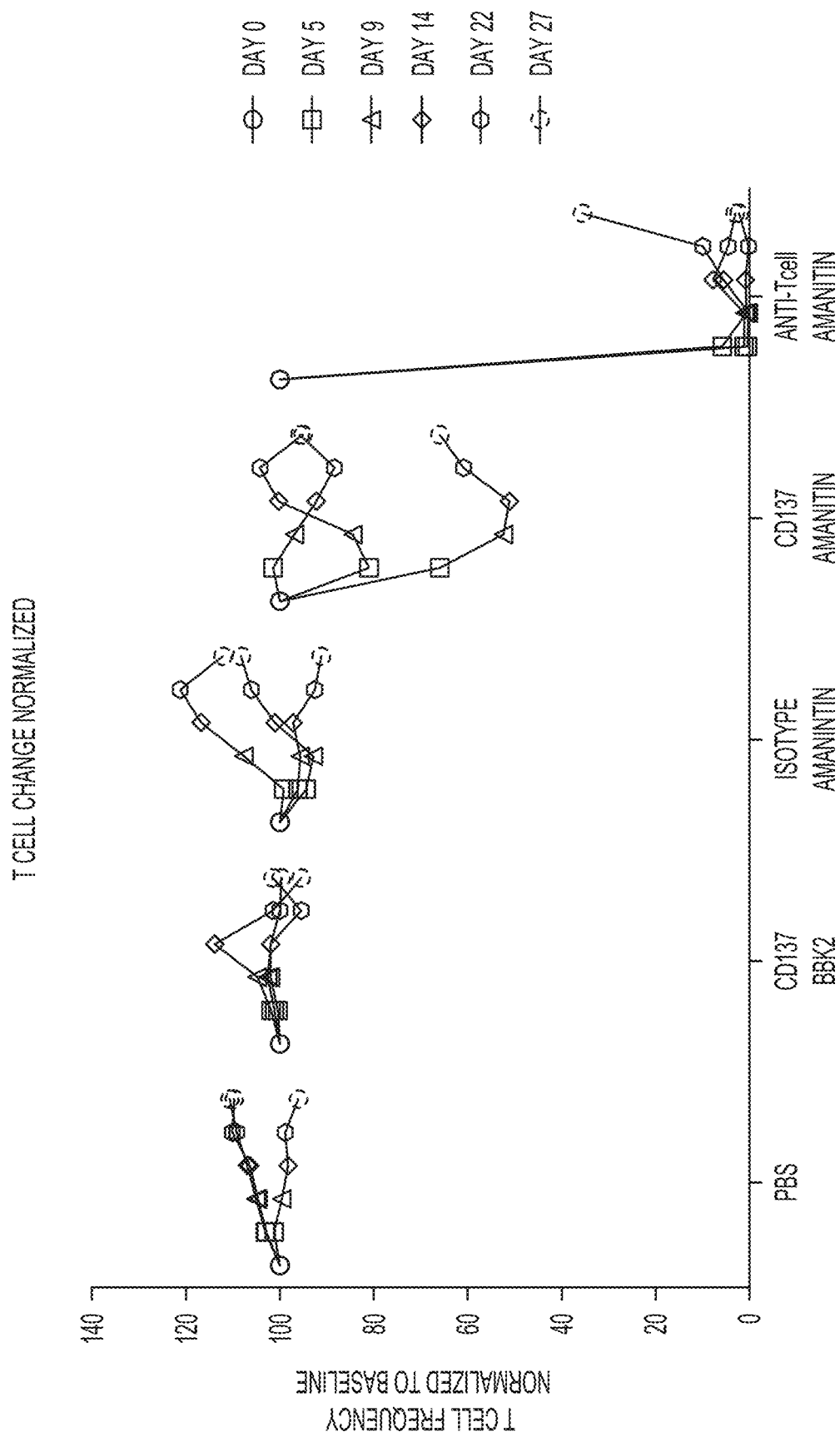

Example 10. Determination of Engraftment Rates and Steady-State T Cell Depletion in a hNSG-SGM3 Mouse Model Female, humanized NSG-SGM3 mice were evaluated for baseline human hematopoietic (overall and T-cell) engraftment rates in the peripheral blood by flow cytometry using hCD45, mCD45, hCD3, and hCD137 antibodies. Mice were randomized and then treated with CD137-Amanitin ADC (chimeric BBK2-Amanitin ADC), Isotype-Amanitin ADC, or an anti-T cell Amanitin ADC, each at a dose of 3 mg/kg. Engraftment and T cell depletion in the periphery of the mice was measured at day 5, day 9, day 14, day 22 and day 27 post treatment (FIGS. 5A and 5B). Peripheral blood was stained to evaluate changes in chimerism and T cell numbers. Equivalent amounts of blood were run on a volumetric flow cytometer and absolute counts were determined based on event numbers. Decreases in engraftment and T cell numbers was normalized to baseline values.

The results in FIGS. 5A and 5B indicate that the anti-CD137-amanitin ADC was well-tolerated in this mouse model. Further, engraftment and T cell frequency (after normalizing to baseline) remained near baseline levels, with a moderate to transient decrease in engraftment and T cell frequency for the anti-CD137-amanitin ADC treated mice. These data indicate that there is generally a lack of T cell depletion in steady-state humanized NSG mice, which indicates that the immune function can be preserved in anti-CD137-amanitin ADC treated mice because most of the T cells are not depleted. To the contrary, mice treated with an ADC that specifically targets an alternate T cell marker ("anti-Tcell-Amanitin") demonstrated complete ablation of engraftment and T cell numbers.

The heavy and light chain amino acid sequences of chimeric BBK2 described in the above examples are set forth in SEQ ID NOs: 23 and 24, respectively.

Other Embodiments

All publications, patents, and patent applications mentioned in this specification are incorporated herein by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the invention that come within known or customary practice within the art to which the invention pertains and may be applied to the essential features hereinbefore set forth, and follows in the scope of the claims.

Other embodiments are within the claims.

The invention claimed is:

1. An antibody drug conjugate (ADC) comprising an anti-CD137 antibody, or antigen binding portion thereof, said antibody comprising a heavy chain variable region comprising a CDR1, a CDR2, and a CDR3 having an amino acid sequence as set forth in SEQ ID NOs: 25, 26, and 27, respectively, and comprising a light chain variable region comprising a CDR1, a CDR2, and a CDR3 having an amino acid sequence as set forth in SEQ ID NOs: 29, 30, and 31, respectively, wherein the antibody, or antigen binding portion thereof, is conjugated at a cysteine residue to an amatoxin via a linker, and wherein the amatoxin is represented by formula (IV)

wherein $R_1$ is H, OH, or $OR_A$;

$R_2$ is H, OH, or $OR_B$;

$R_A$ and $R_B$, together with the oxygen atoms to which they are bound, combine to form a 5-membered heterocyclolalkyl group;

$R_3$ is H or $R_D$;

$R_4$, $R_6$, and $R_7$ are each independently H, OH, $OR_D$, or $R_D$;

$R_5$ is H, OH, $OR_C$, $OR_D$, $R_C$, or $R_D$;

$R_8$ is OH, $NH_2$, $OR_C$, $OR_D$, $NHR_C$, or $NR_CR_D$;

$R_9$ is H, OH, or $OR_D$;

X is —S—, —S(O)—, or —$SO_2$—;

$R_C$ is -L-Z;

$R_D$ is $C_1$-$C_6$ alkyl, $C_1$-$C_6$ heteroalkyl, $C_2$-$C_6$ alkenyl, $C_2$-$C_6$ heteroalkenyl, $C_2$-$C_6$ alkynyl, $C_2$-$C_6$ heteroalkynyl, cycloalkyl, heterocycloalkyl, aryl, or heteroaryl;

L is $C_1$-$C_6$ alkylene, $C_1$-$C_6$ heteroalkylene, $C_2$-$C_6$ alkenylene, $C_2$-$C_6$ heteroalkenylene, $C_2$-$C_6$ alkynylene, $C_2$-$C_6$ heteroalkynylene, cycloalkylene, heterocycloalkylene, arylene, heteroarylene, or comprises a dipeptide; and Z is a chemical moiety formed from a coupling reaction between a reactive substituent present on L and a reactive substituent present within the antibody or antigen-binding fragment thereof, wherein the amatoxin comprises exactly one $R_C$ substituent.

2. The ADC of claim 1, wherein the amatoxin is an amanitin.

3. The ADC of claim 2, wherein the amanitin is selected from the group consisting of α-amanitin, β-amanitin, γ-amanitin, ε-amanitin, amanin, amaninamide, amanullin, amanullinic acid, and proamanullin.

4. A pharmaceutical composition comprising the ADC of claim 1, and a pharmaceutically acceptable carrier.

5. The ADC of claim 1, wherein the heavy chain variable region comprises the amino acid sequence as set forth in SEQ ID NO: 28 and the light chain variable region comprises the amino acid sequence as set forth in SEQ ID NO: 32.

6. The ADC of claim 1, wherein the antibody is an IgG1 or an IgG4 isotype.

7. The ADC of claim 1, wherein the antibody is BBK2.

8. The ADC of claim 1, wherein the amatoxin is α-amanitin.

9. The ADC of claim 1, wherein $R_5$ is $OR_C$.

10. The ADC of claim 1, wherein $R_5$ is $R_C$.

11. The ADC of claim 1, wherein $R_8$ is $OR_C$.

12. The ADC of claim 1, wherein $R_8$ is $NHR_C$.

13. The ADC of claim 1, wherein $R_8$ is $NR_CR_D$.

14. The ADC of claim 1, wherein $R_1$ and $R_2$ are each OH.

15. The ADC of claim 1, wherein L is $C_1$-$C_6$ alkylene, $C_1$-$C_6$ heteroalkylene, $C_2$-$C_6$ alkenylene, $C_2$-$C_6$ heteroalkenylene, $C_2$-$C_6$ alkynylene, $C_2$-$C_6$ heteroalkynylene, or comprises a dipeptide.

16. The ADC of claim 15, wherein L is $C_1$-$C_6$ alkylene, $C_1$-$C_6$ heteroalkylene, $C_2$-$C_6$ alkenylene, $C_2$-$C_6$ heteroalkenylene, $C_2$-$C_6$ alkynylene, or $C_2$-$C_6$ heteroalkynylene.

17. The ADC of claim 15, wherein L comprises a dipeptide.

18. The ADC of claim 1, wherein X is —S—.

19. The ADC of claim 1, wherein X is —S(O)—.

20. The ADC of claim 1, wherein X is —$SO_2$—.

21. An antibody drug conjugate (ADC) comprising an anti-CD137 antibody, or antigen binding portion thereof, said antibody comprising a heavy chain variable region comprising a CDR1, a CDR2, and a CDR3 having an amino acid sequence as set forth in SEQ ID NOs: 25, 26, and 27, respectively, and comprising a light chain variable region comprising a CDR1, a CDR2, and a CDR3 having an amino acid sequence as set forth in SEQ ID NOs: 29, 30, and 31, respectively, wherein the antibody, or antigen binding portion thereof, is conjugated at a cysteine residue to an amatoxin via a linker, and wherein the amatoxin is represented by formula (IV)

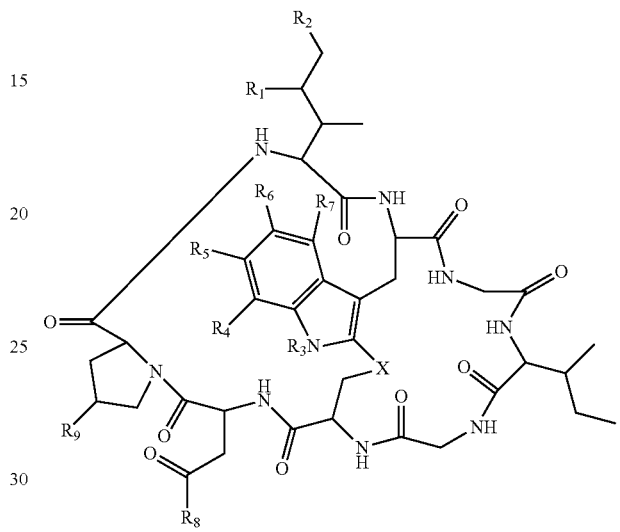

wherein $R_1$ is H, OH, or $OR_A$;

$R_2$ is H, OH, or $OR_B$;

$R_A$ and $R_B$, together with the oxygen atoms to which they are bound, combine to form a 5-membered heterocyclolalkyl group;

$R_3$ is H or $R_D$;

$R_4$, $R_6$, and $R_7$ are each independently H, OH, $OR_D$, or $R_D$;

$R_5$ is $OR_C$ or $R_C$;

$R_8$ is OH, $NH_2$, or $OR_D$;

$R_9$ is H, OH, or $OR_D$;

X is —S—, —S(O)—, or —$SO_2$—;

$R_C$ is -L-Z;

$R_D$ is $C_1$-$C_6$ alkyl, $C_1$-$C_6$ heteroalkyl, $C_2$-$C_6$ alkenyl, $C_2$-$C_6$ heteroalkenyl, $C_2$-$C_6$ alkynyl, $C_2$-$C_6$ heteroalkynyl, cycloalkyl, heterocycloalkyl, aryl, or heteroaryl;

L is $C_1$-$C_6$ alkylene, $C_1$-$C_6$ heteroalkylene, $C_2$-$C_6$ alkenylene, $C_2$-$C_6$ heteroalkenylene, $C_2$-$C_6$ alkynylene, $C_2$-$C_6$ heteroalkynylene, or comprises a dipeptide; and Z is a chemical moiety formed from a coupling reaction between a reactive substituent present on L and a reactive substituent present within the antibody or antigen-binding fragment thereof.

22. A pharmaceutical composition comprising the ADC of claim 21, and a pharmaceutically acceptable carrier.

23. An antibody drug conjugate (ADC) comprising an anti-CD137 antibody, or antigen binding portion thereof, said antibody comprising a heavy chain variable region comprising a CDR1, a CDR2, and a CDR3 having an amino acid sequence as set forth in SEQ ID NOs: 25, 26, and 27, respectively, and comprising a light chain variable region comprising a CDR1, a CDR2, and a CDR3 having an amino acid sequence as set forth in SEQ ID NOs: 29, 30, and 31, respectively, wherein the antibody, or antigen binding portion thereof, is conjugated at a cysteine residue to an amatoxin via a linker, and wherein the amatoxin is represented by formula (IV)

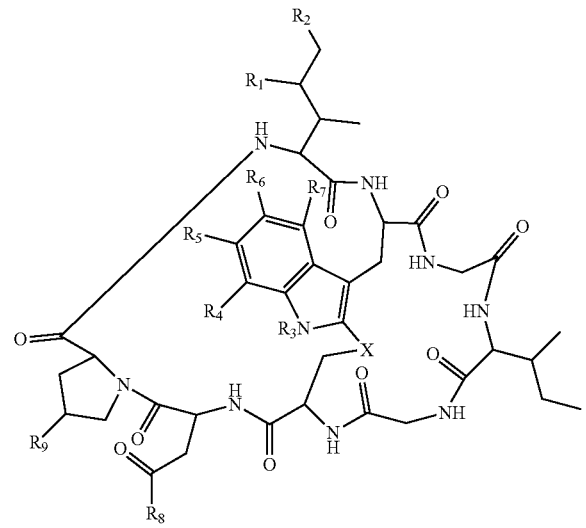

(IV)

wherein $R_1$ is H, OH, or $OR_A$;
$R_2$ is H, OH, or $OR_B$;
$R_A$ and $R_B$, together with the oxygen atoms to which they are bound, combine to form a 5-membered heterocyclolalkyl group;
$R_3$ is H or $R_D$;
$R_4$, $R_6$, and $R_7$ are each independently H, OH, $OR_D$, or $R_D$;
$R_5$ is H, OH, $OR_D$, or $R_D$;
$R_8$ is $OR_C$, $NHR_C$, or $NR_CR_D$;
$R_9$ is H, OH, or $OR_D$;
X is —S—, —S(O)—, or —SO$_2$—;
$R_C$ is -L-Z;
$R_D$ is $C_1$-$C_6$ alkyl, $C_1$-$C_6$ heteroalkyl, $C_2$-$C_6$ alkenyl, $C_2$-$C_6$ heteroalkenyl, $C_2$-$C_6$ alkynyl, $C_2$-$C_6$ heteroalkynyl, cycloalkyl, heterocycloalkyl, aryl, or heteroaryl;
L is $C_1$-$C_6$ alkylene, $C_1$-$C_6$ heteroalkylene, $C_2$-$C_6$ alkenylene, $C_2$-$C_6$ heteroalkenylene, $C_2$-$C_6$ alkynylene, $C_2$-$C_6$ heteroalkynylene, or comprises a dipeptide; and
Z is a chemical moiety formed from a coupling reaction between a reactive substituent present on L and a reactive substituent present within the antibody or antigen-binding fragment thereof.

24. A pharmaceutical composition comprising the ADC of claim 23, and a pharmaceutically acceptable carrier.

* * * * *